(12) United States Patent
Du

(10) Patent No.: US 12,171,429 B2
(45) Date of Patent: Dec. 24, 2024

(54) SURGICAL STAPLER

(71) Applicant: INTOCARE MEDICAL TECHNOLOGY (SUZHOU) CO., LTD., Jiangsu (CN)

(72) Inventor: Yunfeng Du, Jiangsu (CN)

(73) Assignee: INTOCARE MEDICAL TECHNOLOGY (SUZHOU) CO., LTD., Jiangsu (CN)

( * ) Notice: Subject to any disclaimer, the term of this patent is extended or adjusted under 35 U.S.C. 154(b) by 0 days.

(21) Appl. No.: 18/254,676

(22) PCT Filed: Nov. 30, 2020

(86) PCT No.: PCT/CN2020/132995
§ 371 (c)(1),
(2) Date: May 26, 2023

(87) PCT Pub. No.: WO2022/110250
PCT Pub. Date: Jun. 2, 2022

(65) Prior Publication Data
US 2024/0000452 A1    Jan. 4, 2024

(51) Int. Cl.
*A61B 17/072* (2006.01)

(52) U.S. Cl.
CPC .. *A61B 17/072* (2013.01); *A61B 2017/07257* (2013.01); *A61B 2017/07271* (2013.01);
(Continued)

(58) Field of Classification Search
CPC ............ A61B 17/072; A61B 17/07207; A61B 2017/00398; A61B 2017/00473; A61B 2017/07257; A61B 2017/07271
(Continued)

(56) References Cited

U.S. PATENT DOCUMENTS

2002/0047036 A1*  4/2002  Sullivan ........... A61B 17/07207
                                                                  227/19
2016/0235404 A1    8/2016  Shelton, IV
(Continued)

FOREIGN PATENT DOCUMENTS

CN         203564286 U       4/2014
CN         209136741 U       7/2019

*Primary Examiner* — Valentin Neacsu
(74) *Attorney, Agent, or Firm* — McClure, Qualey & Rodack, LLP

(57) ABSTRACT

Provided is a surgical stapler (100), said surgical stapler (100) comprising an end effector (1), a closure mechanism (2), a first drive mechanism (10), and a cutting apparatus. The end effector (1) comprises a staple compartment assembly (11) and a staple anvil (12); surgical staples are provided in the staple compartment assembly (11); the closure mechanism (2) is configured to drive the staple compartment assembly (11) and the staple anvil (12) into joining so as to hold a target tissue; a staple pushing assembly is configured to suture the target tissue by pushing the surgical staple from the staple compartment assembly (11) into the target tissue; the first drive mechanism (10) is configured such that: during the closure phase, the first drive mechanism (10) is removably connected to the closure mechanism (2) so as to drive the closure mechanism (2) to close the end effector (1); in the staple pushing phase after the closure phase, the first drive mechanism (10) separates from the closure mechanism (2) and drives the staple pushing assembly to push the surgical staple out of the staple compartment assembly (11); the cutting apparatus is configured to cut the target tissue during the cutting phase after the target tissue as a whole has been sutured under the drive of the first drive mechanism (10).

18 Claims, 26 Drawing Sheets

(52) U.S. Cl.
CPC ............... *A61B 2017/07278* (2013.01); *A61B 2017/07285* (2013.01)

(58) Field of Classification Search
USPC ...................................................... 227/178.1
See application file for complete search history.

(56) References Cited

U.S. PATENT DOCUMENTS

| | | | |
|---|---|---|---|
| 2018/0126504 A1* | 5/2018 | Shelton, IV | ........... A61B 34/70 |
| 2020/0054324 A1* | 2/2020 | Shelton, IV | ........... A61B 34/30 |
| 2020/0337699 A1* | 10/2020 | Rector | ................. A61B 17/072 |
| 2024/0000452 A1* | 1/2024 | Du | ....................... A61B 17/072 |

* cited by examiner

H-H

SURGICAL STAPLER

TECHNICAL FIELD

At least one embodiment of the present disclosure relates to a surgical stapler.

BACKGROUND

In surgical treatment, various surgical staplers are widely applied, for example, skin surgical staplers, digestive tract (esophagus, gastrointestinal, etc.) circular surgical staplers, rectal surgical staplers, round hemorrhoid surgical staplers, circumcision surgical staplers, vascular surgical stapler, hernia surgical stapler, lung cutting surgical stapler, etc. These surgical staplers are medically used to replace traditional manual suture devices; due to development of modern technologies and improvement of fabrication technologies, various surgical staplers currently used in clinical practice have advantages such as fast and accurate suture, easy operation, less blood loss and less side effects and surgical complications, and so on, sometimes allow resection of focus unresectable in tumor surgeries in the past, and thus are very popular and respected by clinical surgeons at home and abroad.

Usually, surgical staplers perform suture with surgical fasteners made of materials such as medical stainless steel, titanium, titanium alloys, biodegradable magnesium alloys, or the like.

SUMMARY

At least one embodiment of the present disclosure provides a surgical stapler, and the surgical stapler includes an end effector, a closing mechanism, a first driver mechanism, and a cutting device. The end effector includes a fastener-cartridge assembly and an anvil, a surgical fastener is provided in the fastener-cartridge assembly; the closing mechanism is configured to drive the fastener-cartridge assembly and the anvil to engage with each other to close the end effector so that a target tissue is clamped between the fastener-cartridge assembly and the anvil; the surgical fastener pushing assembly is configured to push the surgical fastener out of the fastener-cartridge assembly into the target tissue to suture the target tissue; the first driver mechanism is configured that in a closing stage, the first driver mechanism is in detachable connection with the closing mechanism to drive the closing mechanism to close the end effector; and the first driver mechanism is configured that in a surgical fastener pushing stage after the closing stage, the first driver mechanism is separated from the closing mechanism and drives the surgical fastener pushing assembly to push the surgical fastener out of the fastener-cartridge assembly; and the cutting device is configured to cut, as driven by the first driver mechanism, the target tissue, in a cutting stage after the entire target tissue is sutured.

For example, the surgical stapler provided by at least an embodiment of the present disclosure further comprises a cutting driver mechanism, the cutting driver mechanism is configured to drive, as driven by the first driver mechanism, the cutting device to cut the target tissue.

For example, in the surgical stapler provided by at least an embodiment of the present disclosure, in the closing stage during which the first driver mechanism drives the closing mechanism to close the end effector and in the surgical fastener pushing stage during which the surgical fastener pushing assembly is driven to push the surgical fastener out of the fastener-cartridge assembly, the first driver mechanism moves toward the end effector; and in the cutting stage, the first driver mechanism moves away from the end effector to drive the cutting driver mechanism to move away from the end effector.

For example, the surgical stapler provided by at least an embodiment of the present disclosure further comprises a second driver mechanism, and the second driver mechanism is connected with the first driver mechanism so as to move as driven by the first driver mechanism; the second driver mechanism is configured to be in detachable connection with the closing mechanism in the closing stage and is configured to move as driven by the first driver mechanism toward the end effector to enable the closing mechanism to be in contact with the fastener-cartridge assembly and the anvil and apply pressure to the fastener-cartridge assembly and the anvil to close the end effector in the closing stage; the second driver mechanism is further configured to be separated from the closing mechanism in the surgical fastener pushing stage, and is configured to drive, as driven by the first driver mechanism, the surgical fastener pushing assembly to push the surgical fastener out of the fastener-cartridge assembly in the surgical fastener pushing stage; and the second driver mechanism is further configured to be connected with the cutting driver mechanism in the cutting stage to drive the cutting driver mechanism to move.

For example, in the surgical stapler provided by at least an embodiment of the present disclosure, the end effector comprises a first end and a second end that are opposite to each other in an axial direction, the first end of the end effector is closer to the closing mechanism; before the surgical fastener pushing stage, the cutting device is at the first end of the end effector; in the surgical fastener pushing stage, the first driver mechanism moves along the axial direction toward the end effector to drive the cutting driver mechanism and the surgical fastener pushing assembly to move synchronously toward the end effector, the cutting driver mechanism drives the cutting device to move from the first end of the end effector to the second end of the end effector during which the cutting device does not cut the target tissue; and in the cutting stage, the first driver mechanism moves along the axial direction away from the end effector to drive the cutting driver mechanism to move away from the end effector, and the cutting driver mechanism drives the cutting device to move from the second end of the end effector to the first end of the end effector during which the cutting device cuts the target tissue.

For example, in the surgical stapler provided by at least an embodiment of the present disclosure, the end effector comprises a first end and a second end that are opposite to each other in an axial direction; before the surgical fastener pushing stage, the cutting device is at the second end of the end effector; in the surgical fastener pushing stage, the first driver mechanism moves along the axial direction toward the end effector to drive the cutting driver mechanism and the surgical fastener pushing assembly to move synchronously toward the end effector, the cutting driver mechanism moves from the first end of the end effector to the second end of the end effector to be connected with the cutting device that is at the second end of the end effector; and in the cutting stage, the first driver mechanism moves along the axial direction away from the end effector to drive the cutting driver mechanism to move away from the end effector, and the cutting driver mechanism drives the cutting device to move from the second end of the end effector to the first end of the end effector during which the cutting device cuts the target tissue.

For example, in the surgical stapler provided by at least an embodiment of the present disclosure, the cutting device comprises a blade-carrying member and a cutting blade. The cutting blade is in movable connection with the blade-carrying member, the cutting driver mechanism is configured to drive the blade-carrying member to move so as to drive the cutting blade to move; in the surgical fastener pushing stage, the cutting blade is at least partially in the blade-carrying member, and the cutting blade has a preset distance to the target tissue clamped between the fastener-cartridge assembly and the anvil, so that the cutting blade is not in contact with the target tissue; and in the cutting stage, the cutting blade is driven under action of a first driving force to be in contact with the target tissue to cut the target tissue.

For example, in the surgical stapler provided by at least an embodiment of the present disclosure, the fastener-cartridge assembly comprises a fastener-cartridge, and at least one surgical fastener is provided inside the fastener-cartridge; an outer bracket, fixed on the fastener-cartridge and has a first portion and a second portion that are opposite to each other, wherein both the first portion and the second portion are on a side of the fastener-cartridge away from the anvil and extend along the axial direction, the first portion of the outer bracket and the second portion of the outer bracket are spaced apart from each other to define a first chute extending along the axial direction, and each of the first portion of the outer bracket and the second portion of the outer bracket has an upper surface away from the fastener-cartridge and a lower surface opposite to the respective upper surface; the cutting driver mechanism comprises a main body portion and a first sliding portion; in a process that the cutting driver mechanism drives the blade-carrying member to move, the main body portion is configured to be connected with the blade-carrying member, and the first end of the main body portion away from the anvil slides in the first chute; the first sliding portion is connected with the main body portion and is supported on the upper surface of the first portion of the outer bracket and the upper surface of the second portion of the outer bracket, and is configured to be able to slide along the upper surface of the first portion of the outer bracket and the upper surface of the second portion of the outer bracket; the fastener-cartridge comprises a fastener-cartridge bracket, the fastener-cartridge bracket comprises a first portion and a second portion that both extend along the axial direction, both the first portion of the fastener-cartridge bracket and the second portion of the fastener-cartridge bracket comprises a surgical fastener slot for accommodating the surgical fastener, and the first portion of the fastener-cartridge bracket and the second portion of the fastener-cartridge bracket define a second chute extending along the axial direction, the second chute is opposite to the first chute, and in a process that the cutting driver mechanism drives the blade-carrying member to move, the second end of the main body portion of the cutting driver mechanism close to the anvil slides in the second chute.

For example, in the surgical stapler provided by at least an embodiment of the present disclosure, the fastener-cartridge has a fastener out-put surface opposite to the anvil, and a cross section of an entire body constituted by the main body portion and the first sliding portion in a direction perpendicular to the fastener out-put surface is T-shaped.

For example, in the surgical stapler provided by at least an embodiment of the present disclosure, the cutting driver mechanism further comprises a second sliding portion which is connected with the main body portion, on a side of both the first portion and the second portion away from the first sliding portion, is in contact with the lower surface of the first portion and the lower surface of the second portion, and is configured to be able to slide along the lower surface of the first portion and the lower surface of the second portion.

For example, in the surgical stapler provided by at least an embodiment of the present disclosure, the blade-carrying member comprises: an accommodating cavity, a position limit structure, and a blade ejection driver mechanism. The cutting blade is at least partially located in the accommodating cavity and comprises a cutting edge; the position limit structure is configured to movably connect the cutting blade to the blade-carrying member; and the blade ejection driver mechanism is configured to apply the first driving force to the cutting blade so that the cutting edge moves toward the target tissue to be in contact with the target tissue.

For example, in the surgical stapler provided by at least an embodiment of the present disclosure, the accommodating cavity comprises an opening toward the target tissue, the cutting blade is configured to, under the action of the first driving force, be at least partially exposed from the opening so that the cutting edge is in contact with the target tissue.

For example, in the surgical stapler provided by at least an embodiment of the present disclosure, the accommodating cavity has an inner wall, the inner wall comprises a plurality of wall faces which at least partially intersect with each other, the plurality of wall faces constitute the position limit structure, and in the surgical fastener pushing stage, the plurality of wall faces clamp the cutting blade in a fixed position; the plurality of wall faces include a first wall face and a second wall face that are opposite to each other, the first wall face and the second wall face intersect with the opening and both intersect with the axial direction; under action of the first driving force, the cutting blade slides along the first wall face and the second wall face to be exposed from the opening.

For example, in the surgical stapler provided by at least an embodiment of the present disclosure, both the first wall face and the second wall face are perpendicular to the axial direction.

For example, in the surgical stapler provided by at least an embodiment of the present disclosure, the fastener-cartridge bracket comprises a resistance face; the resistance face faces the blade ejection driver mechanism, the blade ejection driver mechanism is configured to hit the resistance face when the cutting device reaches the second end of the end effector as driven by the cutting driver mechanism, so that the resistance face applies a blade ejection driving force on the blade ejection driver mechanism, and the blade ejection driver mechanism is configured to be in contact with the cutting blade under action of the blade ejection driving force to apply the first driving force to the cutting blade to drive the cutting blade to move toward the target tissue.

For example, in the surgical stapler provided by at least an embodiment of the present disclosure, in the cutting stage, a part of the cutting blade exposed from the opening contacts with the target tissue through the second chute and slides in the second chute.

For example, in the surgical stapler provided by at least an embodiment of the present disclosure, the blade-carrying member further comprises a first connection structure, and the main body portion of the cutting driver mechanism comprises a second connection structure; in the surgical fastener pushing stage, the first connection structure is not connected with the second connection structure; after the surgical fastener pushing stage and before the cutting stage, the first connection structure is connected with the second connection structure.

For example, in the surgical stapler provided by at least an embodiment of the present disclosure, the main body portion further comprises a force applying face facing the blade-carrying member, and the blade-carrying member comprises a force bearing face facing the main body portion; in the surgical fastener pushing stage, the cutting driver mechanism moves toward the blade-carrying member so that the force applying face is in contact with the force bearing face, and the cutting driver mechanism applies a second driving force to the force bearing face through the force applying face to drive the blade-carrying member to move.

For example, in the surgical stapler provided by at least an embodiment of the present disclosure, the first connection structure also serves as the blade ejection driver mechanism, the blade ejection driver mechanism is at least partially located in the accommodating cavity and is configured to be movable along the axial direction; the blade ejection driver mechanism extends along the axial direction, and comprises a first end close to the cutting driver mechanism in the axial direction and a second end opposite to the first end; the blade-carrying member comprises a via hole passing through the force bearing face and in communication with the accommodating cavity; in the surgical fastener pushing stage, the first end of the blade ejection driver mechanism is in the accommodating cavity, the second end of the blade ejection driver mechanism extends to outside of the accommodating cavity, and the blade ejection driver mechanism does not move relative to the cutting blade along the axial direction; in a case where the fastener-cartridge bracket comprises a resistance face, the blade ejection driver mechanism is configured to hit the resistance face when the cutting device reaches the second end of the end effector, so that the resistance face applies a blade ejection driving force on the blade ejection driver mechanism, and the blade ejection driver mechanism is configured to move away from the second end of the end effector along the axial direction under action of the blade ejection driving force to be in contact with the cutting blade to apply the first driving force to the cutting blade to drive the cutting blade to move toward the target tissue, and the first end of the blade ejection driver mechanism moves to the outside of the accommodating cavity through the via hole to be connected with the second connection structure.

For example, in the surgical stapler provided by at least an embodiment of the present disclosure, in the surgical fastener pushing stage, the cutting edge of the cutting blade faces the target tissue, the cutting blade further comprises a first slope intersecting with the cutting edge, the blade ejection driver mechanism comprises a second slope, the second slope is on a side of the first slope away from the cutting edge, is on a side of the first slope that is close to the second end of the end effector in the axial direction, and is parallel to the first slope, and both the first slope and the second slope intersect with the axial direction; when the second end of the blade ejection driver mechanism hits the resistance face, the blade ejection driver mechanism is configured to move away from the second end of the end effector along the axial direction under action of the blade ejection driving force, so that the second slope is in contact with the first slope of the cutting blade to apply the first driving force to the cutting blade, and while the blade ejection driver mechanism moves away from the second end of the end effector along the axial direction, the cutting blade moves toward the target tissue and the first slope slides toward the target tissue relative to the second slope.

For example, in the surgical stapler provided by at least an embodiment of the present disclosure, an included angle between the second slope and a side of the axial direction close to the second end of the end effector is an obtuse angle.

For example, in the surgical stapler provided by at least an embodiment of the present disclosure, the main body portion of the cutting driver mechanism comprises a hollow region, the hollow region runs through the force applying face so that the force applying face has the via hole, the second connection structure is in the hollow region, and the second end of the blade ejection driver mechanism passes through the via hole and enters the hollow region to be connected with the second connection structure.

For example, in the surgical stapler provided by at least an embodiment of the present disclosure, the second connection structure comprises an elastic connection piece, the elastic connection piece protrudes from an inner wall of the hollow region that faces the second end of the blade ejection driver mechanism, wherein the second end of the blade ejection driver mechanism has a nestification hole; the elastic connection piece comprises an elastic connection rod and an end protrusion; the elastic connection rod protrudes from the inner wall of the hollow region that faces the second end of the blade ejection driver mechanism and extends along the axial direction; and the end protrusion is on an end of the elastic connection rod away from the inner wall and protruding from the elastic connection rod along a second direction perpendicular to the axial direction; and the end protrusion is nested in the nestification hole so that the second end of the blade ejection driver mechanism is connected with the elastic connection piece.

For example, in the surgical stapler provided by at least an embodiment of the present disclosure, an end face of the end protrusion that protrudes from the elastic connection rod is an arc-shaped face, and the blade ejection driver mechanism and the elastic connection piece are configured that when the blade ejection driver mechanism moves away from the second end of the end effector along the axial direction under the action of the blade ejection driver mechanism to reach the end protrusion, the second end of the blade ejection driver mechanism abuts against the arc-shaped face to make the elastic connection rod elastically deformed in the second direction, and then when the blade ejection driver mechanism continues to move away from the second end of the end effector along the axial direction under the action of the blade ejection driving force so that the nestification hole is opposite to the end protrusion, under action of an elastic restoring force of the elastic connection rod, the end protrusion moves along the second direction toward the nestification hole and is nested into the nestification hole so that the cutting driver mechanism is connected with the blade-carrying member.

For example, in the surgical stapler provided by at least an embodiment of the present disclosure, the second connection structure comprises an elastic connection piece, the elastic connection piece protrudes from an inner wall of the hollow region that faces the second end of the blade ejection driver mechanism, and the elastic connection piece has a nestification hole; the second end of the blade ejection driver mechanism has an end protrusion, the end protrusion protrudes from the second end of the blade ejection driver mechanism along a second direction perpendicular to the axial direction; and the end protrusion is nested in the nestification hole so that the second end of the blade ejection driver mechanism is connected with the elastic connection piece.

For example, in the surgical stapler provided by at least an embodiment of the present disclosure, the end face of the end protrusion that protrudes from the second end of the blade ejection driver mechanism is an arc-shaped face, and the blade ejection driver mechanism and the elastic connection piece are configured such that: when the blade ejection driver mechanism moves, under action of the blade ejection driving force, away from the second end of the end effector so that the elastic connection piece reaches the end protrusion, the elastic connection piece abuts against the arc-shaped face to make the elastic connection piece elastically deformed in the second direction, and when the blade ejection driver mechanism continues to move, under action of the blade ejection driving force, away from the second end of the end effector along the axial direction so that the nestification hole is opposite to the end protrusion, the elastic connection piece moves, under action of an elastic restoring force of the elastic connection rod, toward the nestification hole along the second direction, so that the end protrusion is nested into the nestification hole to enable the cutting driver mechanism to be connected with the blade-carrying member.

For example, in the surgical stapler provided by at least an embodiment of the present disclosure, the arc-shaped face is a spherical cap face, and the nestification hole is substantially circular.

For example, in the surgical stapler provided by at least an embodiment of the present disclosure, the blade-carrying member further comprises a first connection structure, and the main body portion of the cutting driver mechanism comprises a second connection structure; at least in the surgical fastener pushing stage, the first connection structure is connected with the second connection structure so that cutting driver mechanism is connected with the blade-carrying member.

For example, in the surgical stapler provided by at least an embodiment of the present disclosure, the first connection structure comprises a first connection end close to the cutting driver mechanism, and the second connection structure comprises a second connection end close to the first connection structure; before the surgical fastener pushing stage, the cutting driver mechanism is not connected with the blade-carrying member; and in the surgical fastener pushing stage, as driven by the first driver mechanism, the cutting driver mechanism moves toward the blade-carrying member so that the first connection end is connected with the second connection end.

For example, in the surgical stapler provided by at least an embodiment of the present disclosure, the main body portion of the cutting driver mechanism further comprises a force applying face facing the blade-carrying member, and the blade-carrying member comprises a force bearing face facing the main body portion; in the surgical fastener pushing stage, the cutting driver mechanism moves toward the blade-carrying member so that the force applying face is in contact with the force bearing face, the first connection end is connected with the second connection end, and the cutting driver mechanism applies a second driving force to the force bearing face through the force applying face, and applies a third driving force to the first connection structure through the second connection structure to drive the blade-carrying member to move.

For example, in the surgical stapler provided by at least an embodiment of the present disclosure, the main body portion of the cutting driver mechanism comprises a hollow region, the hollow region runs through the force applying face so that the force applying face has the via hole; the second connection structure is in the hollow region, and the first connection end passes through the via hole and enters the hollow region to be connected with the second connection end of the second connection structure.

For example, in the surgical stapler provided by at least an embodiment of the present disclosure, the second connection structure comprises an elastic connection piece, the elastic connection piece protrudes from the inner wall of the hollow region that faces the first connection end; an end of the elastic connection piece away from the inner wall is the second connection end, and the second connection end has a nestification hole; the elastic connection piece comprises: an elastic connection rod and an end protrusion; the elastic connection rod protrudes from the inner wall of the hollow region that faces the first connection end and extends along the axial direction; and the end protrusion is at one end of the elastic connection rod away from the inner wall and protrudes from the elastic connection rod in a second direction perpendicular to the axial direction; the end protrusion is nested in the nestification hole so that the second end of the blade ejection driver mechanism is connected with the elastic connection piece.

For example, in the surgical stapler provided by at least an embodiment of the present disclosure, the end face of the end protrusion that protrudes from the elastic connection rod is an arc-shaped face, and the cutting driver mechanism and the elastic connection piece are configured such that: when the cutting driver mechanism moves, as driven by the first driver mechanism, along the axial direction toward the second end of the end effector to reach the first connection end, the first connection end abuts against the arc-shaped face to make the elastic connection rod elastically deformed in the second direction; and when the cutting driver mechanism, as driven by the first driver mechanism, continues to move along the axial direction toward the second end of the end effector so that the nestification hole is opposite to the end protrusion, the end protrusion moves, under the action of the elastic restoring force of the elastic connection rod, toward the nestification hole along the second direction so that the elastic connection rod is nested in the nestification hole, so that the first connection end is connected with the second connection end.

For example, in the surgical stapler provided by at least an embodiment of the present disclosure, the second connection structure comprises an elastic connection piece, the elastic connection piece protrudes from the inner wall of the hollow region that faces the first connection end; an end of the elastic connection piece away from the inner wall is the second connection end, and the second connection end has a nestification hole; the elastic connection piece has an end protrusion, and the end protrusion protrudes from the second end of the blade ejection driver mechanism in a second direction perpendicular to the axial direction; and the end protrusion is nested in the nestification hole so that the second end of the blade ejection driver mechanism is connected with the elastic connection piece.

For example, in the surgical stapler provided by at least an embodiment of the present disclosure, the end face of the end protrusion that protrudes from the second end of the blade ejection driver mechanism is an arc-shaped face, and the blade ejection driver mechanism and the elastic connection piece are configured such that: when the blade ejection driver mechanism moves, under action of the blade ejection driving force, away from the second end of the end effector so that the elastic connection piece reaches the end protrusion, the elastic connection piece abuts against the arc-shaped face to make the elastic connection piece elastically deformed in the second direction, and when the blade ejection driver mechanism continues to move, under the action of the blade ejection driving force, away from the second end of the end effector along the axial direction so that the nestification hole is opposite to the end protrusion, the elastic connection piece moves, under action of an elastic restoring force of the elastic connection rod, toward the nestification hole along the second direction, so that the end protrusion is nested into the nestification hole to make the cutting driver mechanism connected with the blade-carrying member.

For example, in the surgical stapler provided by at least an embodiment of the present disclosure, the arc-shaped face is a spherical cap face, and the nestification hole is substantially circular.

For example, in the surgical stapler provided by at least an embodiment of the present disclosure, the surgical fastener pushing assembly comprises surgical fastener pushing pieces, a surgical fastener pushing slide block, and a surgical fastener pushing driver mechanism; the surgical fastener pushing pieces are arranged along the axial direction and configured to apply pressure to the surgical fastener to push the surgical fastener out of the fastener-cartridge assembly; the surgical fastener pushing slide block is configured to apply pressure to the surgical fastener pushing piece to drive the surgical fastener pushing piece to apply a surgical fastener pushing pressure to the surgical fastener; and the surgical fastener pushing driver mechanism is configured to drive the surgical fastener pushing slide block to move along the axial direction as driven by the first driver mechanism in the surgical fastener pushing stage, so that the surgical fastener pushing slide block is sequentially in contact with the surgical fastener pushing pieces to apply the surgical fastener pushing pressure to the surgical fastener pushing pieces.

For example, in the surgical stapler provided by at least an embodiment of the present disclosure, the surgical fastener pushing driver mechanism also serves as the cutting driver mechanism, and the surgical fastener pushing slide block also serves as the blade-carrying member.

For example, in the surgical stapler provided by at least an embodiment of the present disclosure, the surgical fastener pushing slide block comprises: a main body portion and a surgical fastener pushing chute; the surgical fastener pushing chute is on the main body portion and on a side of the main body portion that faces the anvil, is configured to accommodate the surgical fastener pushing piece in the surgical fastener pushing stage during which the surgical fastener pushing slide block moves along the axial direction, and comprises a bottom face facing the anvil, wherein the bottom face is configured to apply the surgical fastener pushing pressure to the surgical fastener pushing piece in the surgical fastener pushing stage.

For example, in the surgical stapler provided by at least an embodiment of the present disclosure, the surgical fastener pushing slide block comprises an accommodating cavity, and the cutting blade is at least partially located in the accommodating cavity; the surgical fastener pushing slide block comprises a first surgical fastener pushing chute and a second surgical fastener pushing chute, in a case where the fastener-cartridge comprises a fastener-cartridge bracket, the fastener-cartridge bracket comprises a first portion and a second portion that both extend along the axial direction, and both the first portion of the fastener-cartridge bracket and the second portion of the fastener-cartridge bracket comprises a surgical fastener slot for accommodating the surgical fastener, the surgical fastener pushed out by the first surgical fastener pushing chute enter into the surgical fastener slot of the first portion of the fastener-cartridge bracket, and the surgical fastener pushed out by the second surgical fastener pushing chute enter into the surgical fastener slot of the second portion of the fastener-cartridge bracket; and the accommodating cavity is between the first surgical fastener pushing chute and the second surgical fastener pushing chute.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

FIG. 12B-2 is a cross-sectionail schematic diagram taken along the line C-C in FIG. 12B-1, which shows a surgical fastener pushing slide block carrying a cutting blade;

DETAILED DESCRIPTION

Figure 1A:
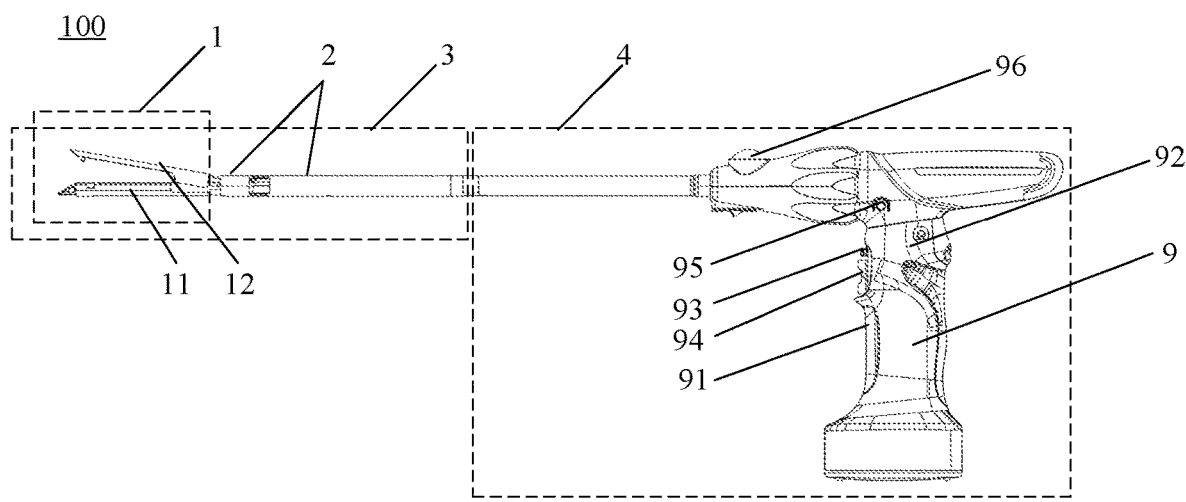
FIG. 1A is an overall structural schematic diagram of a surgical stapler provided by an embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment (s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. Also, the terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "In/inside," "out/outside," "on," "under" and the like are only used to indicate relative position relationship, and when the position of the object which is described is changed, the relative position relationship may be changed accordingly.

The figures in embodiments of the present disclosure are not drawn according to actual proportions or scales. An amount of surgical fastener slots in a fastener-cartridge for accommodating surgical fasteners are not limited to amounts illustrated in the figures, specific sizes of the structures can be determined according to actual acquirements. The figures of the embodiments of the present disclosure are only schematic views.

At least one embodiment of the present disclosure provides a surgical stapler, and the surgical stapler includes an end effector, a closing mechanism, a surgical fastener pushing assembly, and a first driver mechanism. The end effector includes a fastener-cartridge assembly and an anvil, a surgical fastener is provided in the fastener-cartridge assembly; the closing mechanism is configured to drive the fastener-cartridge assembly and the anvil to engage with each other so as to close the end effector; the surgical fastener pushing assembly is configured to push the surgical fastener out of the fastener-cartridge assembly; the first driver mechanism is configured that in a closing stage, the first driver mechanism is in detachable connection with the closing mechanism to drive the closing mechanism to close the end effector; and the first driver mechanism is configured that in a surgical fastener pushing stage after the closing stage, the first driver mechanism is separated from the closing mechanism and drives the surgical fastener pushing assembly to push the surgical fastener out of the fastener-cartridge assembly. The surgical stapler may be applied to a medical field, for example, as a surgical instrument in a surgical procedure. During operation of the surgical stapler, the closing stage and the surgical fastener pushing stage are independent of each other without interfering with each other, and the first driver mechanism is configured to drive the implementation of the two stages.

At least one embodiment of the present disclosure provides a surgical stapler, and the surgical stapler includes an end effector, a closing mechanism, a first driver mechanism, and a cutting device. The end effector includes a fastener-cartridge assembly and an anvil, a surgical fastener is provided in the fastener-cartridge assembly; the closing mechanism is configured to drive the fastener-cartridge assembly and the anvil to engage with each other to close the end effector so that a target tissue is clamped between the fastener-cartridge assembly and the anvil; the surgical fastener pushing assembly is configured to push the surgical fastener out of the fastener-cartridge assembly into the target tissue to suture the target tissue; the first driver mechanism is configured that in a closing stage, the first driver mechanism is in detachable connection with the closing mechanism to drive the closing mechanism to close the end effector; and the first driver mechanism is configured that in a surgical fastener pushing stage after the closing stage, the first driver mechanism is separated from the closing mechanism and drives the surgical fastener pushing assembly to push the surgical fastener out of the fastener-cartridge assembly; and the cutting device is configured to cut, as driven by the first driver mechanism, the target tissue, in a cutting stage after the entire target tissue is sutured.

At least one embodiment of the present disclosure provides a surgical stapler, and the surgical stapler includes an end effector, a closing mechanism, a surgical fastener pushing assembly, and a lock mechanism. The end effector includes a fastener-cartridge assembly and an anvil, a surgical fastener is provided in the fastener-cartridge assembly; in an initial state, the end effector is in an open state; in a closing stage, the closing mechanism is configured to drive the fastener-cartridge assembly and the anvil to engage with each other to close the end effector so that a clamp target tissue is clamped between the fastener-cartridge assembly and the anvil; in a surgical fastener pushing stage after the closing stage, the surgical fastener pushing assembly is configured to push the surgical fastener out of the fastener-cartridge assembly to suture the target tissue; the lock mechanism is configured to limit, in the surgical fastener pushing stage, the closing mechanism in a first position to the closing mechanism keeps the end effector in the closed state, and is configured to limit, in the initial state, the closing mechanism in a second position to keep the end effector in the open state.

At least one embodiment of the present disclosure provides a surgical stapler, and the surgical stapler includes an end effector, a closing mechanism, a surgical fastener pushing assembly, a first driver mechanism and an articulation mechanism. The end effector includes a fastener-cartridge assembly and an anvil, and at least one surgical fastener is provided in the fastener-cartridge assembly; the closing mechanism is configured to drive the fastener-cartridge assembly and the anvil to engage with each other to close the end effector so that a target tissue is clamped between the fastener-cartridge assembly and the anvil; the surgical fastener pushing assembly is configured to push the surgical fastener out of the fastener-cartridge assembly; the first driver mechanism is configured that in a closing stage, the first driver mechanism is in detachable connection with the closing mechanism to drive the closing mechanism to close the end effector; and the first driver mechanism is configured that in a surgical fastener pushing stage after the closing stage, the first driver mechanism is separated from the closing mechanism and drives the surgical fastener pushing assembly to push the surgical fastener out of the fastener-cartridge assembly to suture the target tissue; the articulation mechanism includes a front articulation driver assembly and a rear articulation driver assembly, and the front articulation driver assembly and the rear articulation driver assembly are configured to drive the end effector to pivot; the surgical stapler comprises a main body portion and a detachable portion, the detachable portion is in detachable connection with the main body portion; the end effector and the front articulation driver assembly are comprised in the detachable portion, the first driver mechanism and the rear articulation driver assembly are comprised in the main body portion; the detachable portion is in detachable connection with the main body portion to enable the front articulation driver assembly to be in detachable connection with the rear articulation driver assembly.

At least one embodiment of the present disclosure provides a surgical stapler, and the surgical stapler includes an end effector, a closing mechanism, and a surgical fastener pushing assembly. The end effector includes a fastener-cartridge assembly and an anvil, and a least one surgical fastener is provided in the fastener-cartridge assembly; the closing mechanism is configured to drive, in a closing stage, the fastener-cartridge assembly and the anvil to engage with each other so that the end effector clamps the target tissue, the end effector has a first end close to the closing mechanism and a second end away from the closing mechanism; the surgical fastener pushing assembly is configured to push, in a surgical fastener pushing stage after the closing stage, the surgical fastener from the fastener-cartridge assembly into the target tissue along a direction from the second end to the first end, to suture the target tissue along a direction from the second end to the first end.

At least one embodiment of the present disclosure provides a handle, and the handle is configured to be in detachable connection with a detachable portion, the detachable portion includes an end effector, the end effector includes a fastener-cartridge assembly and an anvil; the handle includes a dial switch, the dial switch includes a dial provided on a first surface of the handle, and the dial is configured to be toggled to rotate to control a pivoting direction of the end effector and a pivoting angle of the end effector. The handle may be used in a surgical stapler, and the surgical stapler may be used as a medical instrument, for example, a surgical instrument, configured to clamp target tissue, suture and cut the target tissue.

At least one embodiment of the present disclosure provides a surgical stapler main body, and the surgical stapler main body includes any one of the handles provided by the embodiments of the present disclosure, and a driver portion connected with the handle; an extension direction of the driver portion is an axial direction, the axial direction intersects with the extension direction of the handle; an end of the driver portion away from the handle is in detachable connection with the detachable portion, and includes an electric motor and a rear articulation driver member; the electric motor is in signal connection with the dial switch, and the dial switch controls operation of the electric motor; the rear articulation driver member is connected with the electric motor and extends along the axial direction, and the electric motor is configured to rotate, under control of the dial switch, to drive the rear articulation driver member to move along the axial direction so as to drive the end effector to pivot.

At least one embodiment of the present disclosure provides a surgical stapler, and the surgical stapler includes any one of the surgical stapler main bodies provided by the embodiments of the present disclosure, and the detachable portion. The detachable portion is in detachable connection with the surgical stapler main body, the detachable portion further includes a front articulation driver assembly; the front articulation driver assembly is connected with the end effector, and the detachable portion is in detachable connection with the surgical stapler main body to enable the front articulation driver assembly to be in detachable connection with the rear articulation driver member, and the front articulation driver assembly drives, as driven by the rear articulation driver member, the end effector to pivot.

Figure 1B:
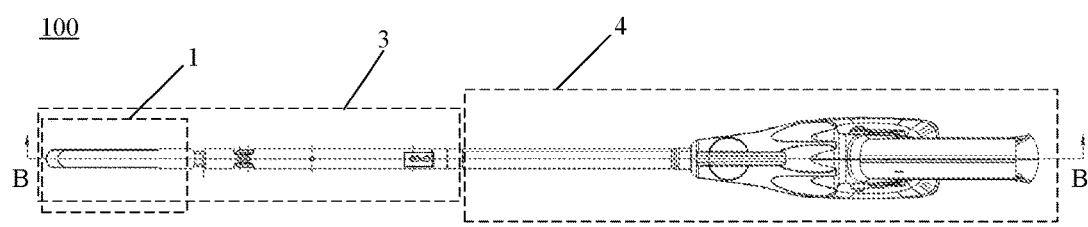
FIG. 1B is a top view of the surgical stapler shown in FIG. TA.
Figure 2:
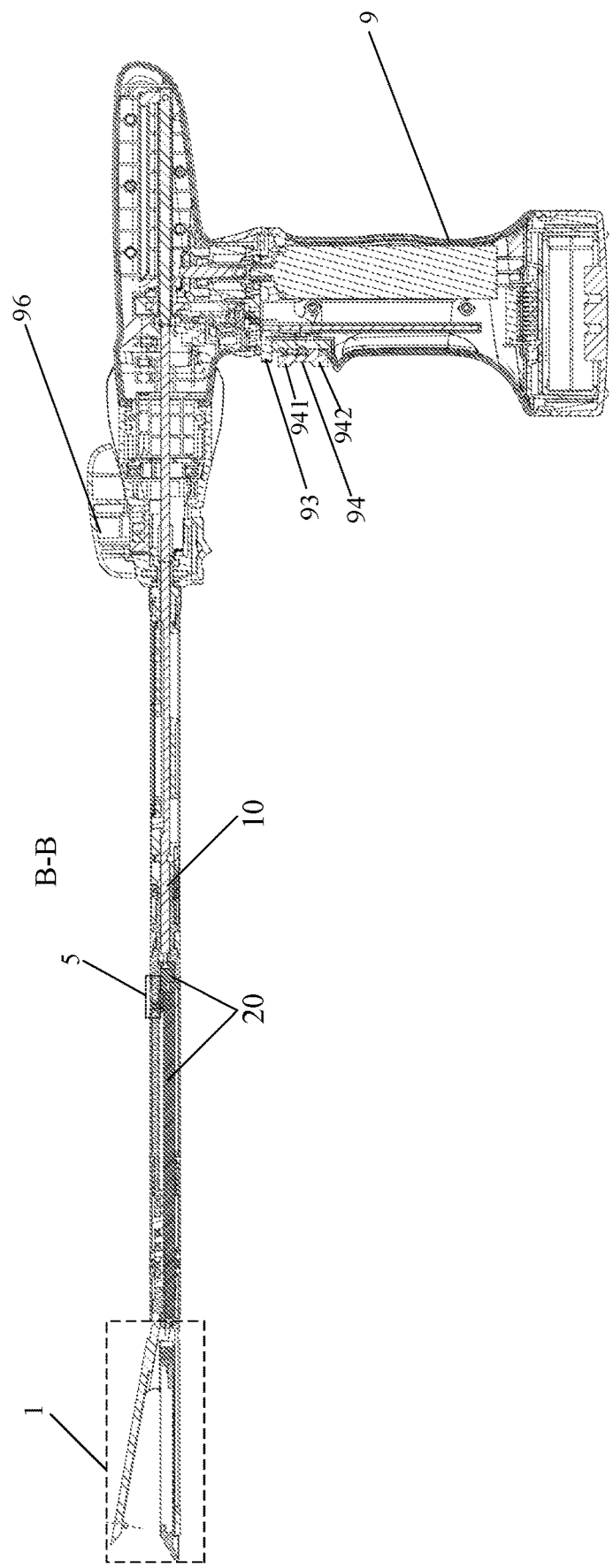
FIG. 2 is an overall cross-sectional schematic diagram along a line B-B in FIG. 1B.
Figure 3:
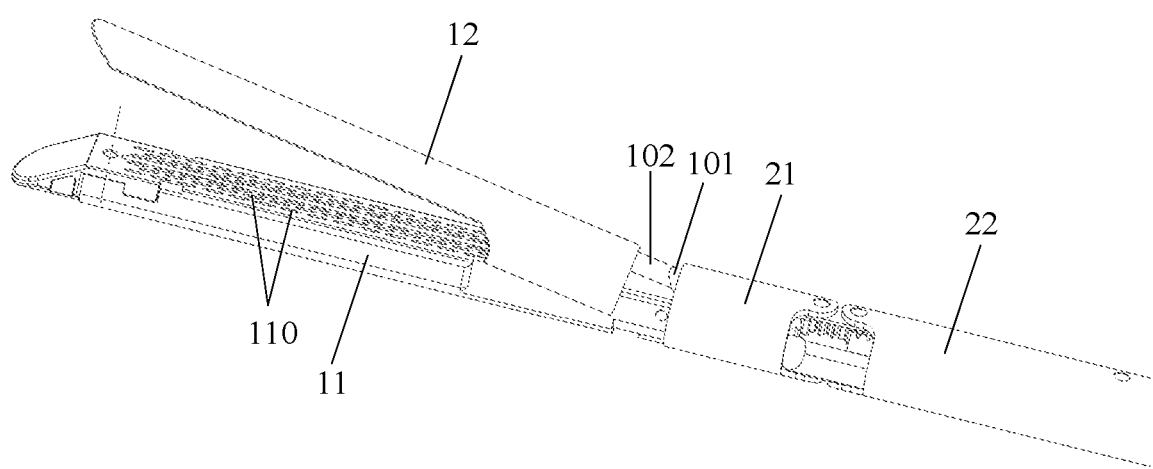
FIG. 3 is a partial schematic diagram including an end effector and a closing mechanism of a surgical stapler provided by an embodiment of the present disclosure.
Figure 4:
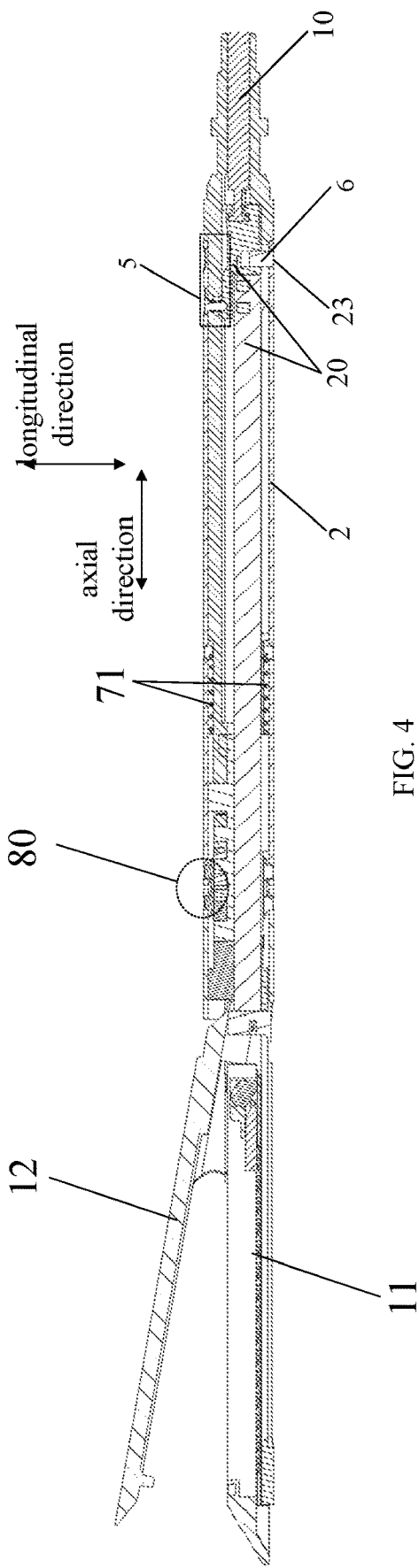
FIG. 4 is a partial schematic diagram including a first driver mechanism, a second driver mechanism, a closing mechanism and an end effector of a surgical stapler provided by an embodiment of the present disclosure.

Exemplarily, FIG. TA is a schematic diagram of an overall structure of a surgical stapler 100 provided by an embodiment of the present disclosure, FIG. 1B is a top view of the surgical stapler shown in FIG. TA, FIG. 2 is an overall cross-sectional schematic diagram along a line B-B in FIG. 1B; FIG. 3 is a partial schematic diagram including an end effector and a closing mechanism of a surgical stapler provided by an embodiment of the present disclosure, and FIG. 4 is a partial schematic diagram including a first driver mechanism, a second driver mechanism, a closing mechanism and an end effector of a surgical stapler provided by an embodiment of the present disclosure. The surgical stapler 100 may be applied to a medical field, and the embodiment of the present disclosure is described by taking the surgical stapler 100 as a surgical instrument in a surgical procedure.

In conjunction with FIG. 1A to FIG. 4, the surgical stapler 100 includes an end effector 1, a closing mechanism 2, a surgical fastener pushing assembly 11 and a first driver mechanism 10. The end effector 1 includes a fastener-cartridge assembly 11 and an anvil 12. At least one surgical fastener is provided in the fastener-cartridge assembly 11. The closing mechanism 2 is configured to drive the fastener-cartridge assembly 11 and the anvil 12 to engage with each other so as to close the end effector 1; the surgical fastener pushing assembly 11 is configured to push the surgical fastener out of the fastener-cartridge assembly 11; the first driver mechanism 10 is configured that in a closing stage, the first driver mechanism 10 is in detachable connection with the closing mechanism 2 to drive the closing mechanism 2 to close the end effector 1 so that a target tissue is clamped by the end effector 1; in a surgical fastener pushing stage after the closing stage, the first driver mechanism 10 is separated from the closing mechanism 2 and drive the surgical fastener pushing assembly to push the surgical fastener out of the fastener-cartridge assembly to drive the surgical fastener to nail into the target tissue and suture the target tissue. The above-described target tissue is, for example, target tissue to be sutured and cut during surgery, for example, human body tissue or animal body tissue. During operation of the surgical stapler 100, the closing stage and the surgical fastener pushing stage are independent of each other without interfering with each other, and the first driver mechanism 10 is configured to drive the implementation of the two stages, which greatly simplifies a driver mechanism and thus effectively simplifies the overall structure of the surgical stapler 100, saves space and is favorable for reducing a radial size of the surgical stapler 100, so that it is easy for the surgical stapler 100 to enter a surgical object, for example, a human body, in a surgical procedure, to reduce injuries to the surgical object; in addition, simplification of the driver mechanism makes the operation process of the surgical stapler 100 easier and smoother to be implemented, which makes an outstanding contribution to improving reliability of the operation of the surgical stapler, and also reduces difficulty in designing a control system for controlling the operation process of the surgical stapler 100.

For example, the fastener-cartridge assembly 11 includes a first end close to the closing mechanism 2, the anvil 12 includes a first end close to the closing mechanism 2, and the first end of the fastener-cartridge assembly 11 is in movable connection with the first end of the anvil 12; the closing mechanism 2 is configured to apply pressure to the first end of the fastener-cartridge assembly 11 and the first end of the anvil 12 to enable the two to get close to each other and engage with each other. The anvil 12 includes an operation surface facing the fastener-cartridge assembly 11, the fastener-cartridge assembly 11 includes a fastener out-put surface opposite to the operation surface, and the closing mechanism 2 is configured to drive the operation surface and the fastener out-put surface to get close to each other and engage with each other.

In the embodiment shown in FIG. 1A to FIG. 4, at least one surgical fastener slot 110 is provided on the fastener-cartridge of the fastener-cartridge assembly, and each surgical fastener slot has an opening facing the anvil 12. In some examples, an opening of each surgical fastener slot may independently be in a square shape, a circular shape, a triangular shape, etc., and is independently configured to allow, in the surgical fastener pushing stage, the surgical fastener accommodated in the surgical fastener slot to be ejected through the opening of the surgical fastener slot. The number of the surgical fastener slot and the shape of each surgical fastener slot are not limited to above cases in the embodiments of the present disclosure.

In some examples, openings of a plurality of surgical fastener slots may be arranged uniformly on a fastener out-put surface of the fastener-cartridge or arranged in a pattern. For example, the openings of the plurality of surgical fastener slots may be arranged to form a shape of at least one straight line, rectangle, triangle, rhombus, circle, etc. on the fastener out-put surface of the fastener-cartridge, and the arrangement form is not limited by the embodiment of the present disclosure.

In some examples, the surgical fastener may be made of a material that is compatible with, or at least harmless to, the human body. For example, the material of the surgical fastener may include at least one selected from a group consisting of medical stainless steel, titanium, titanium alloy, biodegradable magnesium alloy and the like. Further, for example, at least a part of a surface of the surgical fastener may be provided with a passivation layer, a plating layer or a coating layer, etc. that are compatible with the human body or at least harmless to the human body, and the material of the surgical fastener is not limited by the embodiments of the present disclosure.

In some examples, the anvil 12 may be made of, for example, a rigid material that is compatible with the human body or at least harmless to the human body. The material of the anvil 12 may include, for example, a metal material such as medical stainless steel, titanium, titanium alloy, cobalt alloy, and the like, or a non-metallic material such as medical ceramics, hard plastics, and the like. For example, at least a part of an inner surface and/or an outer surface of the anvil 12 may further be provided with a passivation layer, a plating layer or a coating layer, etc. that are compatible with the human body or at least harmless to the human body, and the material of the anvil is not by the embodiment of the present disclosure.

For example, as shown in FIG. 2 and FIG. 4, the surgical stapler 100 further includes a second driver mechanism 20; the second driver mechanism 20 is connected with the first driver mechanism 10, in the closing stage, the second driver mechanism 20 is in detachable connection with the closing mechanism 2, and is configured to move, as driven by the first driver mechanism 10, toward the end effector 1 to enable the closing mechanism to be in contact with the fastener-cartridge assembly 11 and the anvil 12 and apply pressure to the fastener-cartridge assembly 11 and the anvil 12 to close the end effector 1; the second driver mechanism 20 is further configured to be separated from the closing mechanism 2 in the surgical fastener pushing stage, and to drive, as driven by the first driver mechanism 10, the surgical fastener pushing assembly to push the surgical fastener out of the fastener-cartridge assembly 11.

Figure 5A:
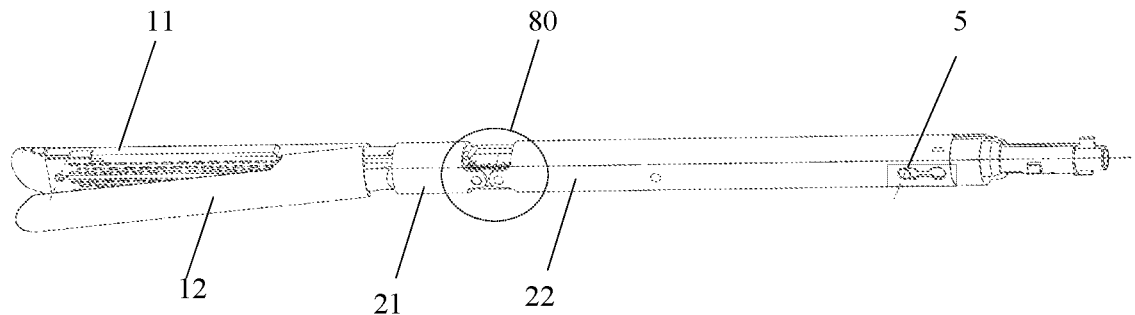
FIG. 5A is an overall schematic diagram of a detachable portion of a surgical stapler provided by an embodiment of the present disclosure.

FIG. 5A is an overall schematic diagram of a detachable portion 3 of the surgical stapler 100 provided by an embodiment of the present disclosure; as shown in FIG. 5A, FIG. 1A and FIG. 2, the surgical stapler 100 includes a main body portion 4 and a detachable portion 3, the detachable portion 3 is in detachable connection with the main body portion 4; the first driver mechanism 10 is located in the main body portion 4; the second driver mechanism 20, the closing mechanism 2, the surgical fastener pushing assembly and the end effector 1 are located in the detachable portion 3, and the detachable portion 3 is connected with the main body portion 4 to enable the second driver mechanism 20 to be in detachable connection with the first driver mechanism 10. The detachable portion 3 is designed to enter a surgical object, for example, a portion of the human body in a surgical procedure, the main body portion 4 does not need to enter the surgical object; the detachable portion 3 may be replaced, for example, one detachable portion 3 is replaced for each surgical operation which means that the detachable portion 3 is a single use loading part, without replacing the main body portion 4 including the first driver mechanism, which greatly saves costs. As compared with a detachable structure that may be detached from the handle, the detachable portion 3 simplifies a structure of the detachable portion and reduces a volume of the detachable portion, and further reduces the number of single use loading parts, thereby further reducing costs and improving a reuse rate of the main body portion.

Figure 5B:
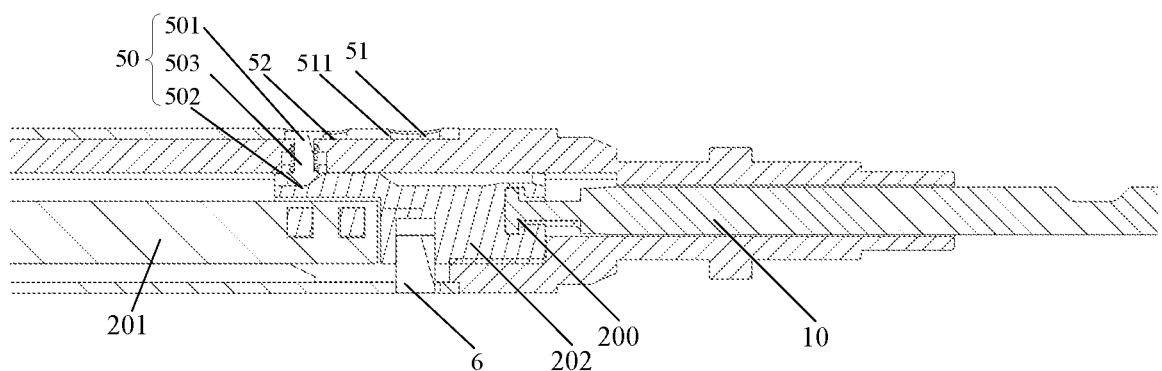
FIG. 5B is a cross-sectional schematic diagram of connection of a main body portion with a detachable portion of a surgical stapler provided by an embodiment of the present disclosure.
Figure 5C:
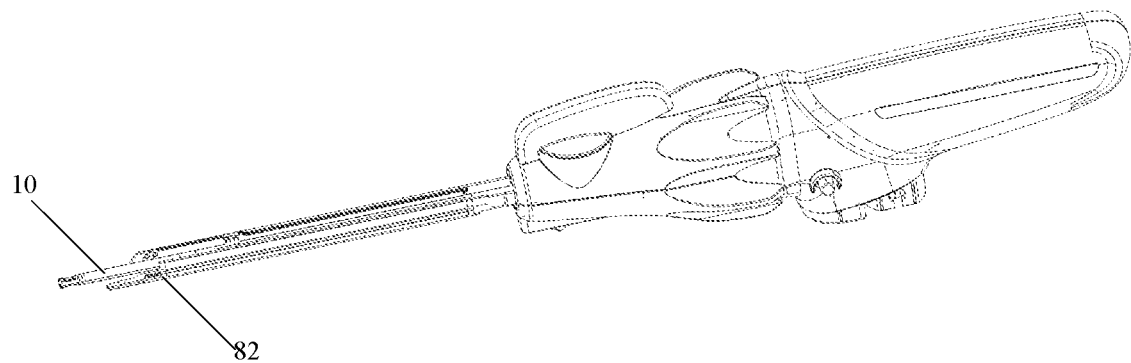
FIG. 5C is a schematic diagram of an end portion of a main body portion of a surgical stapler connected with a detachable portion provided by an embodiment of the present disclosure.

For example, as shown in FIG. 2 and FIG. 4, the extension direction of the first driver mechanism 10 and the second driver mechanism 20 is an axial direction, and the first driver mechanism 10 includes a first end away from the end effector 1 in the axial direction and a second end opposite to the first end of the first driver mechanism 10; the second driver mechanism 20 includes a first end close to the first driver mechanism 10 and a second end away from the first driver mechanism 10 in the axial direction. FIG. 5B is a cross-sectional schematic diagram of connection of the detachable portion 3 with the main body portion 4 of the surgical stapler 100 provided by an embodiment of the present disclosure; FIG. 5C is a schematic diagram of an end portion of the main body portion 4 that is connected with the detachable portion 3 in a surgical stapler 100 provided by an embodiment of the present disclosure. For example, as shown in FIG. 5B to FIG. 5C, the main body portion 4 and the detachable portion 3 may be in plug connection with each other. In the process of connecting the main body portion 44 and the detachable portion 3, the first end of the second driver mechanism 20 has a groove 200, and the second end of the first driver mechanism 10 has a protrusion structure, the protrusion structure is configured to be inserted into the groove, then, after rotating the detachable portion 3 in a positive direction relative to the main body portion 4, for example, by 90°, the protrusion structure of the second end of the first driver mechanism 10 is blocked by a groove wall of the groove of the first end of the second driver mechanism 20, and thus is unable to move relative to the second driver mechanism 20 along the axial direction, so as to lock the protrusion structure of the second end of the first driver mechanism 10 at the position, and thus realize the connection of the second end of the first driver mechanism 10 and the first end of the second driver mechanism 20 with the first driver mechanism 10; in the case that the detachable portion 3 needs to be detached from the main body portion 4, the detachable portion 3 is rotated in an direction opposite to the positive direction relative to the main body portion 4, for example, by 90°, so as to unlock the protrusion structure of the second end of the first driver mechanism 10, to detach the first driver mechanism 10 from the second driver mechanism 20, that is, detach the detachable portion 3 from the main body portion 4. This detachable connection mode is simple to operate, easy to control, and is favorable for stability of the surgical stapler during use and installation of the surgical stapler. Of course, the main body portion 4 and the detachable portion 3 may also be connected in a variety of connection modes such as screw connection or clamping connection, and the second end of the first driver mechanism 10 and the first end of the second driver mechanism 20 may also be connected in other detachable connection modes such as clamping connection, hook connection, magnetic connection, which is not limited by the present disclosure.

For example, in the closing stage during which the first driver mechanism 10 drives the closing mechanism 2 to close the end effector 1 and in the surgical fastener pushing stage during which the surgical fastener pushing assembly is driven to push the surgical fastener out of the fastener-cartridge assembly 11, the first driver mechanism 10 moves toward the end effector 1. For example, the second driver mechanism 20 is further configured to be separated from the closing mechanism 2 in the surgical fastener pushing stage, and to drive, as driven by the first driver mechanism 10, the surgical fastener pushing assembly to push the surgical fastener out of the fastener-cartridge assembly 11. For example, in the closing stage and the surgical fastener pushing stage, the second driver mechanism 20 also moves toward the end effector 1 along the axial direction as driven by the first driver mechanism 10. For example, in the closing stage and the surgical fastener pushing stage, both the first driver mechanism 10 and the second driver mechanism 20 make substantially linear movement along the axial direction. For example, the first driver mechanism 10 is a single driver rod; in this way, the single driver rod moves in the axial direction to drive the completion of the closing stage and the surgical fastener pushing stage, which greatly simplifies the driver mechanism and thus effectively simplifies the overall structure of the surgical stapler 100, saves space and is favorable for reducing a size of the surgical stapler 100, so that it is easy for the surgical stapler 100 to enter the surgical object, for example, the human body in a surgical procedure, thereby reducing injuries to the surgical object; in addition, simplification of the driver mechanism makes the operation process of the surgical stapler 100 easier and smoother to be implemented, which makes an outstanding contribution to improving reliability of the operation of the surgical stapler 100, and also reduces difficulty in designing a control system for controlling the operation process of the surgical stapler 100.

For example, as shown in FIG. 4 and FIG. 5B, the surgical stapler 100 further includes a separable connection structure 6; the separable connection structure 6 is configured to be connected with the closing mechanism 2 and the second driver mechanism 20 in the closing stage so as to move toward the end effector 1 with movement of the second driver mechanism 20, to drive the closing mechanism 2 to move toward the end effector 1, so as to close the end effector 1; and the separable connection structure 6 is configured to be separated from the closing mechanism 2 after the end effector 1 is closed. The extension direction of the first driver mechanism 10 and the second driver mechanism 20 is the axial direction; a direction perpendicular to the axial direction is a longitudinal direction; the separable connection structure 6 includes a first end and a second end in the longitudinal direction; the second driver mechanism 20 includes a first connection structure, and the closing mechanism 2 includes a second connection structure.

For example, in the process where the separable connection structure 6 drives the closing mechanism 2 to move toward the end effector 1, the first end of the separable connection structure 6 is connected with the second driver mechanism 20 through the first connection structure, and the second end is connected with the closing mechanism 2 through the second connection structure; the separable connection structure 6 is configured to be longitudinally movable relative to the first connection structure and the second connection structure so that the second end of the separable connection structure 6 is separated from the closing mechanism or so that the first end of the separable connection structure 6 is separated from the second driver mechanism 20.

For example, the surgical stapler 100 further includes a separation driver structure, the separation driver structure is configured to apply a driving force along the longitudinal direction to the separable connection structure 6 after the end effector 1 is closed, so that the separable connection structure 6 moves along the longitudinal direction under the action of the driving force, and thus the second end of the separable connection structure 6 is separated from the closing mechanism, or, the first end of the separable connection structure 6 is separated from the second driver mechanism 20.

Exemplarily, FIG. 6A to FIG. 6F are schematic diagrams of connection and separation of the separable connection structure and the closing mechanism of the surgical stapler 100 during the closing process provided by an embodiment of the present disclosure. In conjunction with FIG. 6A to FIG. 6E, for example, the closing mechanism is a sleeve 2 sleeved on an outer side of the second driver mechanism 20; the second connection structure is a connection hole 23 passing through a sleeve wall of the sleeve 2, and the second end of the separable connection structure 6 is detachably plugged into the connection hole 23. FIG. 7 is a schematic diagram of the separable connection structure provided by the embodiment shown in FIG. 6A to FIG. 6F; as shown in FIG. 6A to FIG. 6F and FIG. 7, in this embodiment, the separable connection structure 6 is a slide block; the first connection structure is a groove 203 provided in the second driver mechanism 20. Of course, in other embodiments, the separable connection structure 6 may be of other types, and is not limited to the slide block; the first connection structure is not limited to the groove, and the second connection structure is not limited to the above-described connection hole 23 passing through the sleeve wall of the sleeve 2, as long as the above-described functions can be implemented. The closing mechanism is also not limited to the sleeve 2, and may also be any other mechanism that can drive to close and open the end effector 1 as driven by the first driver mechanism 10.

The sleeve 2 may be made of, for example, a rigid material that is compatible with the human body or at least harmless to the human body. For example, the material of the sleeve 2 may include, for example, a metal material such as medical stainless steel, titanium, titanium alloy, and cobalt alloy, and the like; or a non-metallic material such as medical ceramics and hard plastics, and the like. Further, at least a portion of an inner surface and/or an outer surface of the sleeve 2 may also be provided with a passivation layer, a plating layer or a coating layer that is compatible with the human body or at least harmless to the human body, and the material of the sleeve is not limited by the embodiments of the present disclosure.

For example, the sleeve 2 is a hollow arc-shaped cylinder having a circular cross section, so as to reduce contusion to tissue of the surgical object when the sleeve 2 enters the surgical object, for example, the human body in a surgical procedure. The sleeve 2 has a sleeve wall and a cavity surrounded by the sleeve wall; in the closing stage, structures such as the second driver mechanism 20 are located in the cavity, to minimize the structures located outside the sleeve 2, so as to minimize contusion to the tissue of the surgical object when the sleeve 2 enters the surgical object such as the human body in a surgical procedure. The sleeve 2 has one end away from the end effector 1 partially closed and the other end open to the end effector 1 open.

Figure 6A:
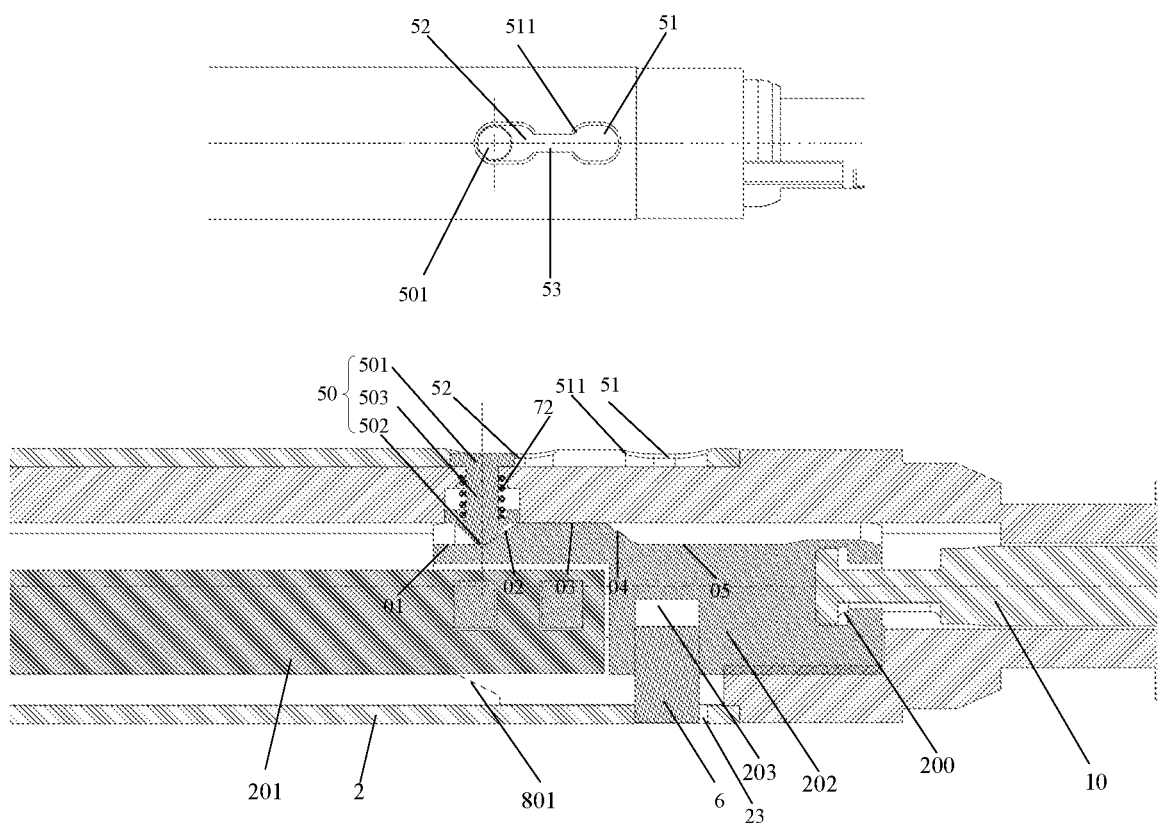
FIG. 6A to FIG. 6F are schematic diagrams of connection and separation of a separable connection structure and a closing mechanism in a close process of a surgical stapler provided by an embodiment of the present disclosure.
Figure 6B:
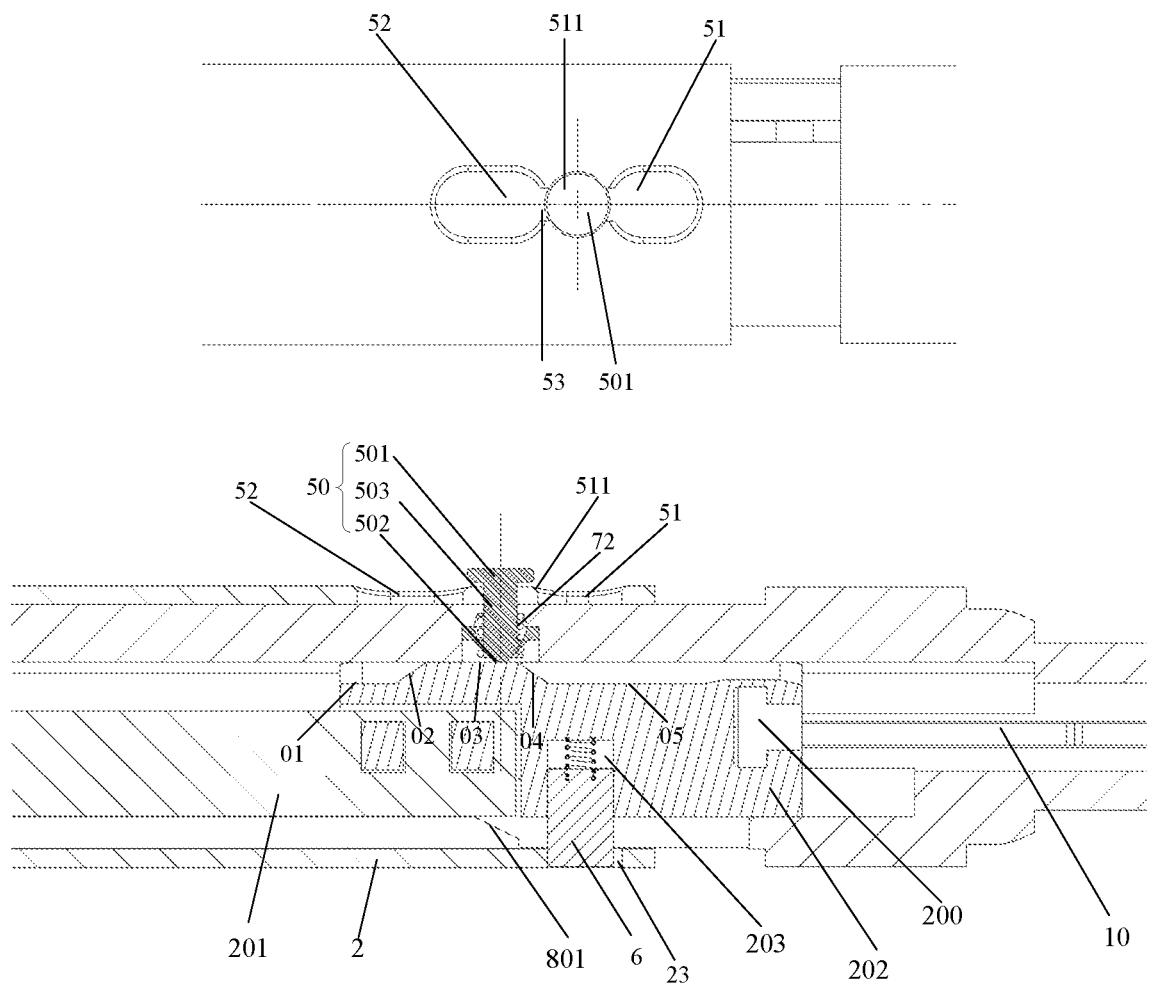
Figure 7:
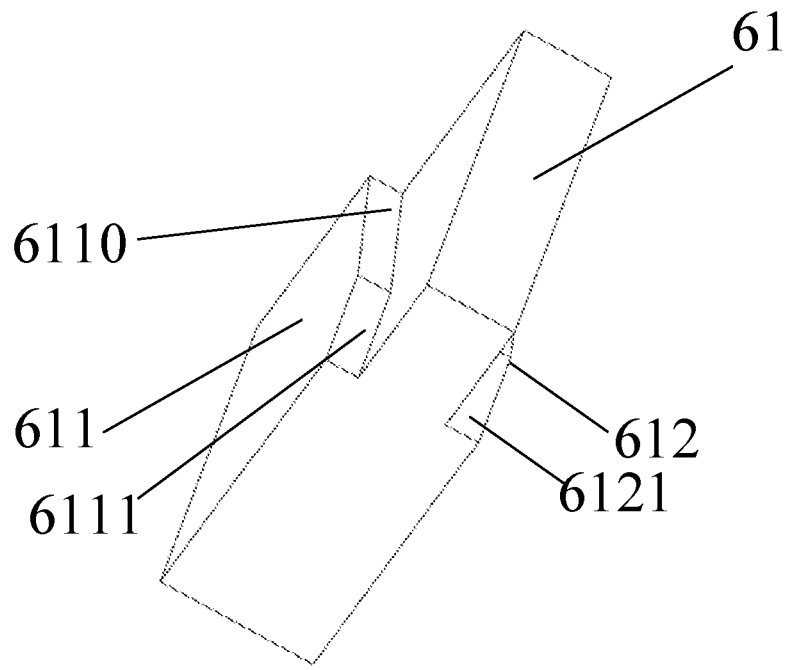
FIG. 7 is a schematic diagram of the separable connection structure provided by the embodiment shown in FIG. 6A to FIG. 6F.

As shown in FIGS. 6A-6B and FIG. 7, in the closing stage, the first end of the separable connection structure 6 is connected with the second driver mechanism 20 through the connection hole 23 on the sleeve 2, and the second end of the separable connection structure 6 is connected with the sleeve 2 through the groove 203 of the second driver mechanism 20, so that the closing mechanism is connected with the second driver mechanism 20 through the separable connection structure 6, and the sleeve 2 moves toward end effector 1 with movement of the second driver mechanism 20, to drive the sleeve 2 to move toward the end effector 1. Referring to FIG. 3, the fastener-cartridge assembly 11 includes a first end close to the sleeve 2, and the anvil 12 includes a first end close to the sleeve 2; in the closing stage, the second driver mechanism 20 moves toward the end effector 1 as driven by the first driver mechanism 10, to drive the sleeve 2 to move toward the end effector 1, so that the sleeve 2 is sleeved on the first end of the fastener-cartridge assembly 11 and the first end of the anvil 12, and applies pressure to the first end of the fastener-cartridge assembly 11 and the first end of the anvil 12 to close the end effector 1, so that the end effector 1 clamps the target tissue.

Figure 6C:
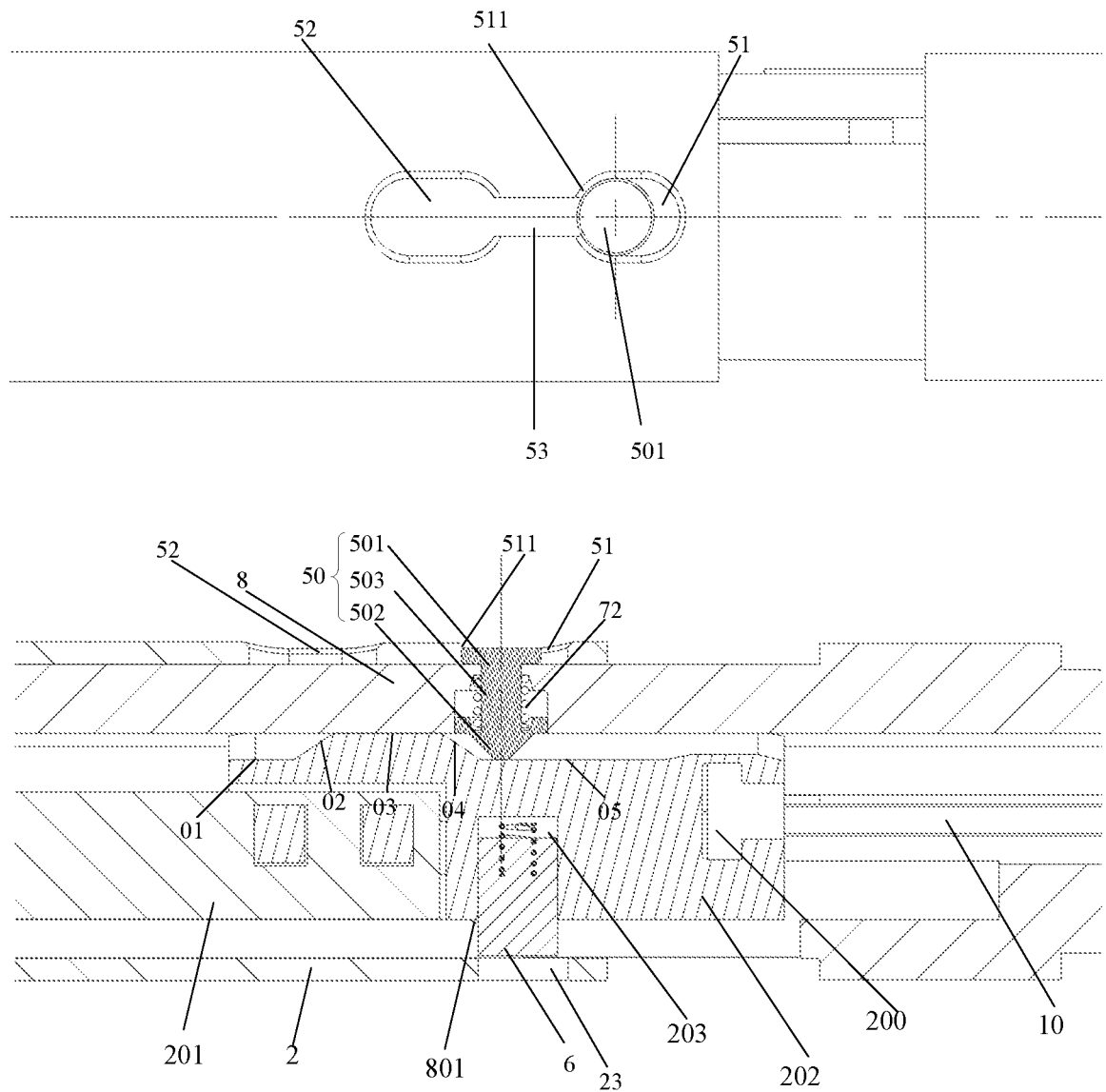
Figure 6D:
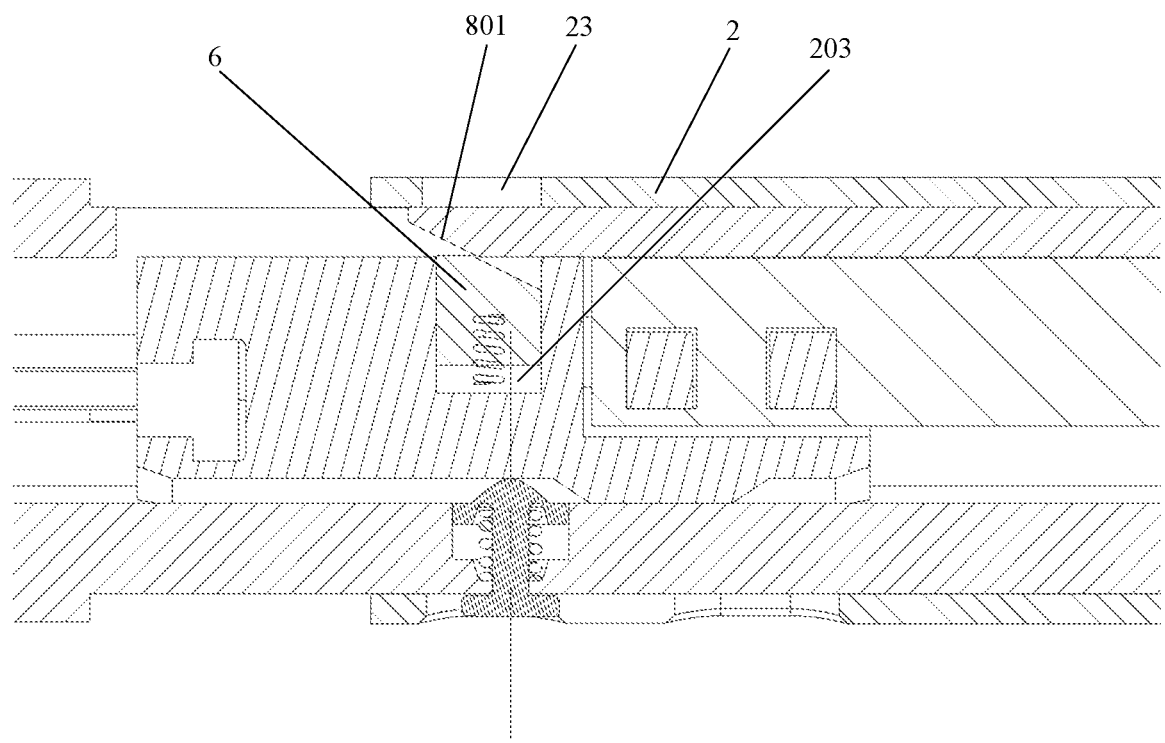
Figure 6E:
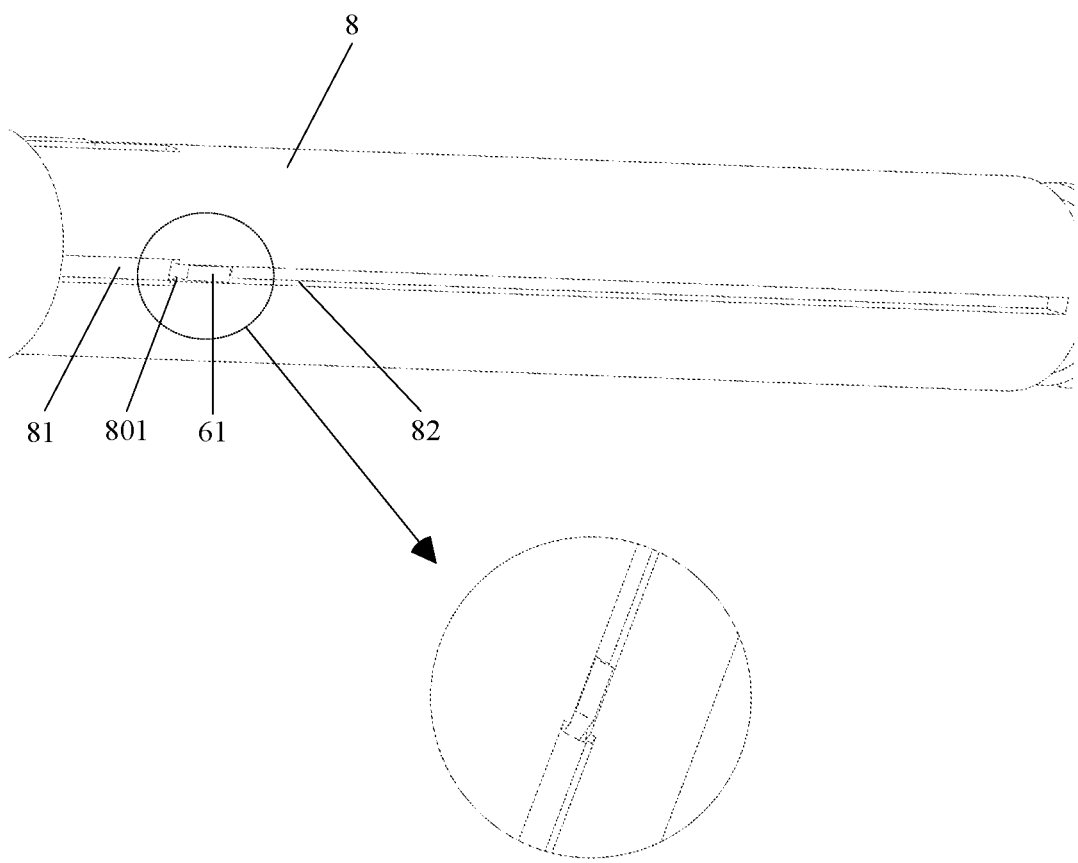

The separable connection structure 6 in FIG. 6A to FIG. 6F is in detachable connection with the second driver mechanism 20 and is in detachable connection with the closing mechanism. In conjunction with FIG. 7, the separable connection structure 6 includes a main body portion 61 and a first boss 611 protruding from a first surface of the main body portion 61, the first surface of the main body portion 61 faces the groove 203, the first boss 611 is located at the first end of the separable connection structure 6; the first boss 611 includes a first inclined plane 6111; and the first inclined plane 6111 intersects with the axial direction and the longitudinal direction. As shown in FIG. 6E, the surgical stapler 100 further includes a fixing bracket 8, the closing mechanism is arranged on the fixing bracket 8, and the fixing bracket 8 includes a first chute 81 and a second chute 82; the first chute 81 extends along the axial direction; the second chute 82 extends along the axial direction, to be in communication with the first chute 81, is located on a side of the first chute 81 close to the end effector 1, and includes a first chute wall and a second chute wall that are opposite to each other in a lateral direction; the lateral direction is perpendicular to the axial direction and the longitudinal direction, and the first groove wall is used as the separation driver structure; a surface of the first chute wall facing the separable connection structure 6 has a first barrier slope 801, and the first barrier slope 801 intersects with the axial direction and the longitudinal direction.

In the closing stage, one end of the main body portion 61 of the separable connection structure 6 is located in the connection hole 23 of the sleeve 2 to drive the sleeve 2 to move along the axial direction; and the first boss 611 is partially embedded in the groove 203 so that the separable connection structure 6 moves toward the end effector 1 with movement of the second driver mechanism 20. The separation driver structure is located on a side of the separable connection structure 6 close to the end effector 1; after the separable connection structure 6 drives the sleeve 2 to move along the axial direction toward the end effector 1 to close the end effector 1, the first barrier slope 801 is in contact with a first inclined plane 6111 of the first boss 611, so as to apply an axial resistance force and a longitudinal driving force to the first inclined plane 6111; the first barrier slope 801 is parallel to the first inclined plane 6111, and the separable connection structure 6 moves along the longitudinal direction under the action of the longitudinal driving force, so that the second end of the separable connection structure 6 is separated from the closing mechanism, as shown in FIG. 6C to FIG. 6F. In this embodiment, for example, in the closing stage, an end face of the first boss 611 of the separable connection structure 6 that is at least partially located in the groove 203 in the longitudinal direction and a bottom face of the groove 203 that faces the end face of the first boss 611 are spaced apart by a sliding distance, so that in the surgical fastener pushing stage, the separable connection structure 6 can slide along the longitudinal direction toward the bottom face of the groove 203 to be separated from the sleeve 2. That is, after the separable connection structure 6 drives the closing mechanism to move toward the end effector 1 along the axial direction to close the end effector 1, the separation driver structure is in contact with the first inclined plane 6111 to apply an axial resistance force and a longitudinal driving force to the first inclined plane 6111, and the separable connection structure 6 moves along the longitudinal direction under the action of the longitudinal driving force.

Figure 6F:
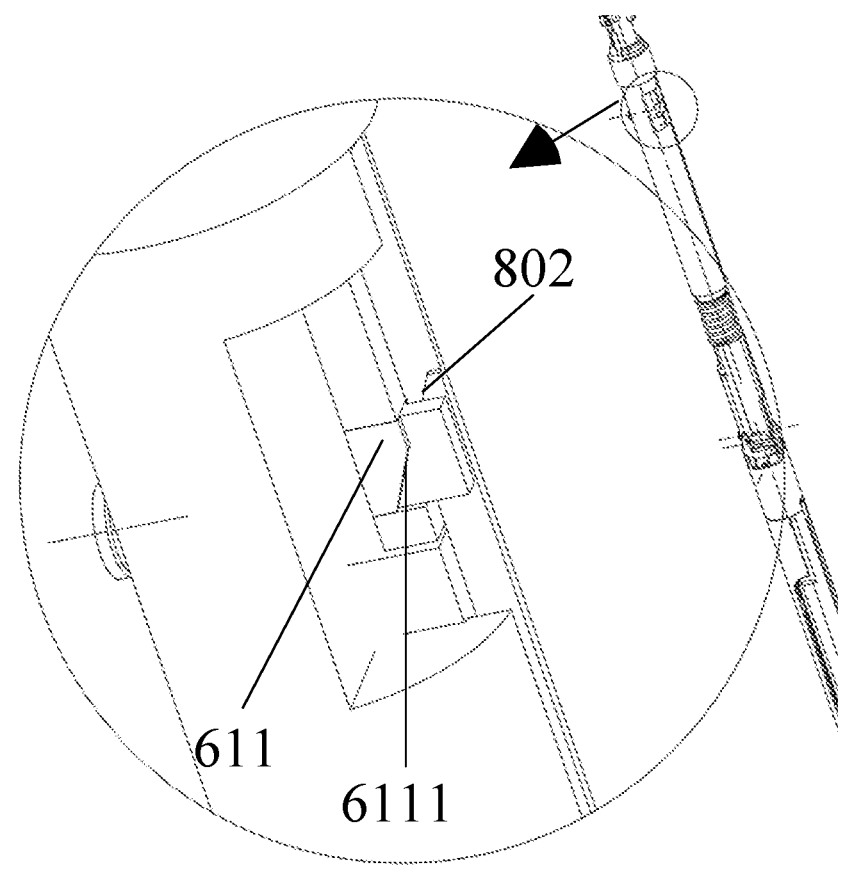

As shown in FIG. 6F, after the closing stage, at least a part of the main body portion 61 of the separable connection structure 6 in the axial direction enters the second chute 82 to enable the first barrier slope 801 to be in contact with the first inclined plane 6111. In this way, the limited space in the sleeve 2 is fully utilized to implement that the separable connection structure 6 connects the second driver mechanism 20 and the sleeve 2 in the closing stage and is separated from the sleeve 2 in the surgical fastener pushing stage after the closing stage, so that in the surgical fastener pushing stage, when the first driver mechanism 10 and the second driver mechanism 20 drive the surgical fastener pushing assembly to push the surgical fastener, the sleeve 2 no longer moves with axial movement of the second driver mechanism 20, which maintains stability of the closed end effector 1.

For example, a thickness of the first boss 611 in the lateral direction is greater than a depth of the groove 203 in the lateral direction, so that the main body portion 61 of the separable connection structure 6 is located on an outer side of the groove 203, which facilitates the main body portion of the separable connection structure 6 to enter the second chute 82.

For example, in the longitudinal direction, the first inclined plane 6111 exceeds the groove 203, that is, in the longitudinal direction, the first inclined plane 6111 is located on an outer side of the groove 203, to ensure that the main body portion of the separable connection structure 6 is in contact with the first barrier slope 801 after entering the second chute 82, and ensure reliability of normal operation of the surgical stapler 100 in the closing stage.

For example, in the embodiment shown in FIG. 6A to FIG. 6F, an included angle close to the end effector 1 among included angles between the first inclined plane 6111 and the axial direction is an obtuse angle, and this included angle is an included angle between the first inclined plane 6111 and a central axis of the sleeve 2. The separable connection structure 6 moves away from the closing mechanism along the longitudinal direction under the action of the longitudinal driving force and is separated from the closing mechanism; in this way, in the surgical fastener pushing stage, the separable connection structure 6 is located inside the cavity of the sleeve 2, avoiding an obvious protrusion structure on the outer side of the sleeve 2, so as to avoid or reduce contusion to the tissue of the surgical object caused by the protrusion structure located on the outer side of the sleeve 2 when the sleeve 2 enters the surgical object such as the human body in a surgical procedure.

Of course, in other embodiments, the included angle close to the end effector 1 among the included angles between the first inclined plane 6111 and the axial direction may be designed to be an acute angle, and the separable connection structure 6 moves close to the sleeve 2 along the longitudinal direction under the action of the longitudinal driving force and thus is separated from the second driver mechanism 20, that is, in this case, the direction of the driving force is opposite to the direction of the driving force according to the embodiment shown in FIG. 6A to FIG. 6F, and a movement direction of the separable connection structure 6 is opposite to a movement direction the separable connection structure 6 according to the embodiment shown in FIG. 6A to FIG. 6F. In this case, the separable connection structure 6 is located on the sleeve 2 without moving with movement of the second driver mechanism 20 in the surgical fastener pushing stage. That is, in some other embodiments, the first end of the separable connection structure 6 is separated from the second driver mechanism 20, and after the sleeve 2 drives to close the end effector 1, the separable connection structure 6 is separated from the second driver mechanism 20 so as to stop driving the closing mechanism to move.

In some embodiments, for example, as shown in FIG. 7, the separable connection structure 6 further includes a second boss 612. The second boss 612 protrudes from the second surface of the main body portion, is located at the first end of the separable connection structure 6, and includes a second inclined plane 6121 intersecting with the axial direction and the longitudinal direction, the second surface is opposite to the first surface; the second groove wall also serves as the separation driver structure, and includes a second barrier slope 802 facing the separable connection structure 6; the second barrier slope 802 is configured to be in contact with the second inclined plane 6121 to apply an axial resistance force and a longitudinal driving force to the second inclined plane 6121, and is parallel to the second inclined plane 6121; after the closing stage, at least a part of the main body portion of the separable connection structure 6 in the axial direction enters the second chute 82, and the first boss 611 and the second boss 612 are blocked outside the second chute 82 by the first groove wall and the second groove wall so that the first barrier slope 801 is in contact with the first inclined plane 6111, and the second barrier slope 802 is in contact with the second inclined plane 6121. The second boss 612 can not only increase symmetry of the separable connection structure 6 and improve structural stability of the separable connection structure 6, but can also increase the magnitude of the driving force, which is favorable for ensuring the reliability of driving the separable connection structure 6 to be separated from the sleeve 2. For example, after the first barrier slope 801 and the first inclined plane 6111 are in contact with each other, the first barrier slope 801 and the first inclined plane 6111 are complementary; and after the second barrier slope 802 and the second inclined plane 6121 are in contact with each other, the second barrier slope 802 and the second inclined plane 6121 are complementary.

For example, as shown in FIG. 7, the first boss 611 further includes a first platform portion; the first platform portion has a first horizontal plane 6110; the first horizontal plane 6110 intersects and is connected with the first inclined plane 6111; and the first platform portion can increase mechanical strength of the first boss 611, so that the first boss 611 has a more stable structure and a more stable position when located in the groove 203. Similarly, the second boss 612 further includes a second platform portion; the second platform portion has a second horizontal plane; the second horizontal plane intersects and is connected with the second inclined plane 6121; the second platform portion can increase mechanical strength of the second boss 612; and in a case where the first boss 611 has a first platform portion, symmetry of the separable connection structure 6 is increased to make the structure thereof more stable.

For example, a width in the lateral direction of the first chute 81 is greater than a width in the lateral direction of the second chute 82, so that only the main body portion 61 of the separable connection structure 6 can enter the second chute 82, while the first boss 611 and the second boss 612 cannot enter the second chute 82, so as to drive the separable connection structure 6 to move along the longitudinal direction to be separated from the sleeve 2 as described above.

For example, in some embodiments, a width in the lateral direction of the second chute 82 is greater than a width of the main body portion 61 in the lateral direction and less than a sum of a width in the lateral direction of the first boss 611, the width in the lateral direction of the main body portion 61 and a width of the second boss 612, so as to minimize the width of the first chute 81, and ensure sufficient space for the first boss 611 and the second boss 612 when the main body portion 61 of the separable connection structure 6 slides in the first chute 81, which is favorable for stability of the position of the main body portion of the separable connection structure 6 when the main body portion 61 of the separable connection structure 6 slides in the first chute 81, and also is favorable for improving mechanical strength and mechanism stability of the fixing bracket 8, so as to improve the stability of the entire surgical stapler 100.

For example, in other embodiments, the lateral width in the lateral direction of the first chute 81 is greater than a sum of the width in the lateral direction of the first boss 611, the width in the lateral direction of the main body portion 61, and the width in the lateral direction of the second boss 612, to ensure sufficient space for the first boss 611 and the second boss 612 when the main body portion 61 of the separable connection structure 6 slides in the first chute 81, so as to ensure that subsequently the main body portion 61 of the separable connection structure 6 enters the second chute 82 smoothly.

For example, an length in the axial direction of the second chute 82 is less than an length in the axial direction of the first chute 81, so as to minimize a size of a slot on the fixing bracket 8, which is favorable for improving mechanical strength and mechanism stability of the fixing bracket 8, so as to improve the stability of the entire surgical stapler 100.

The above embodiments are exemplary, in other embodiments, the separable connection structure 6 may be in fixed connected with one selected from a group consisting of the second driver mechanism 20 and the closing mechanism, and is in detachable connection with the other selected from the group consisting of the second driver mechanism 20 and the closing mechanism.

As shown in FIG. 3, for example, the end of the end effector 1 close to the sleeve 2 includes a guide slope 101; the guide slope 101 has non-zero included angles with both the axial direction and the longitudinal direction; the guide slope 101 includes a first end close to the sleeve 2 and a second end away from the sleeve 2 in the axial direction; and the first end is also closer to the sleeve 2 than the second end in the longitudinal direction. In the closing stage, the sleeve 2 is in contact with the guide slope 101 before being in contact with the fastener-cartridge assembly 11 and the anvil 12, and slides along the guide slope 101 toward the fastener-cartridge assembly 11 and the anvil 12, so that it is more easily to realize that the sleeve 2 is sleeved on the first end of the fastener-cartridge assembly 11 and the first end of the anvil 12 to apply pressure to the first end of the fastener-cartridge assembly 11 and the first end of the anvil 12, so as to close the end effector 1, which increases the reliability of proceeding the closing stage normally.

For example, the sleeve wall of the sleeve 2 includes a curved face, for example, the above-described arc-shaped face; as shown in FIG. 3, at least one of the first end of the fastener-cartridge assembly 11 and the first end of the anvil 12, for example, the first end of the anvil 12, includes a curved force bearing face 102; the curved force bearing face 102 is configured to be in contact with the sleeve 2 and bear pressure applied by the sleeve 2, to increase the force application area of sleeve 2 to the end effector 1 in the closing stage, which is favorable for driving the end effector 1 to close, and favorable for the stability of the operation of the surgical stapler 100 after the end effector 1 is closed, and favorable for reducing slippage of the target tissue. For example, the sleeve 2 includes an inner surface in contact with the force bearing face, the inner surface is a curved face; a curvature of the force bearing face is equal to a curvature of the inner surface of the sleeve 2, so as to further increase the force application area of sleeve 2 to the end effector 1 in the closing stage, which is favorable for driving the end effector 1 to close, favorable for the stability of the operation of the surgical stapler 100 after the end effector 1 is closed, and favorable for reducing slippage of the target tissue.

Figure 13A:
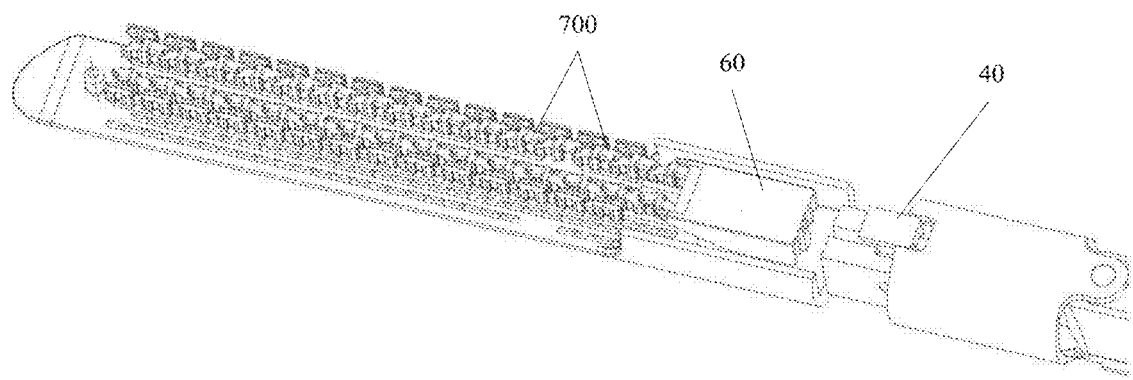
FIG. 13A is a schematic diagram of a surgical fastener pushing process.

FIG. 13A is a schematic diagram of a surgical fastener pushing process. For example, referring to FIG. 13A, the surgical fastener pushing assembly includes a surgical fastener pushing piece 700, a surgical fastener pushing slide block 60 and a surgical fastener pushing driver mechanism 40. The surgical fastener pushing piece 700 is configured to apply surgical fastener pushing pressure to the surgical fastener to push the surgical fastener out of the fastener-cartridge; the surgical fastener pushing slide block 60 is configured to apply pressure to the surgical fastener pushing piece 700 to drive the surgical fastener pushing piece 700 to apply the surgical fastener pushing pressure to the staple; the driver mechanism 40 is configured to move along the axial direction as driven by the first driver mechanism and the second driver mechanism 20, to drive the surgical fastener pushing slide block 60 to move along the axial direction, so that the surgical fastener pushing slide block 60 is in contact with the surgical fastener pushing piece 700 to apply surgical fastener pushing pressure to the surgical fastener pushing piece 700.

For example, in some embodiments, before the surgical fastener pushing stage, the surgical fastener pushing driver mechanism 40 is connected with the second driver mechanism 20, and moves with movement of the second driver mechanism 20 to be in contact with the surgical fastener pushing slide block 60, which is more favorable for reliability that the second driver mechanism 20 subsequently drives the surgical fastener pushing driver mechanism 40 to move and is more favorable for operation stability of the surgical stapler 100 in the surgical fastener pushing stage, and reduces design difficulty.

For example, in other embodiments, before the surgical fastener pushing stage, the surgical fastener pushing driver mechanism 40 is located on a side of the second driver mechanism 20 close to the surgical fastener pushing slide block 60 and has an interval with the second driver mechanism 20, that is, at this time, the surgical fastener pushing driver mechanism 40 is not connected with the second driver mechanism 20, and the second driver mechanism 20 moves toward the end effector 1 along the axial direction, and is connected with the surgical fastener pushing slide block 60 after passing through the interval between the surgical fastener pushing driver mechanism 40 and the second driver mechanism 20.

For example, after the surgical fastener pushing stage, the first driver mechanism 10 is further configured to drive the closing mechanism to move away from the end effector 1, so that the fastener-cartridge assembly 11 and the anvil 12 move away from each other to open the end effector 1. That is, the closing mechanism, for example, the sleeve 2 moves away from the end effector 1 to release the first end of anvil 12 and the first end of fastener-cartridge assembly 11 to open anvil 12 and fastener-cartridge assembly 11.

Figure 8:
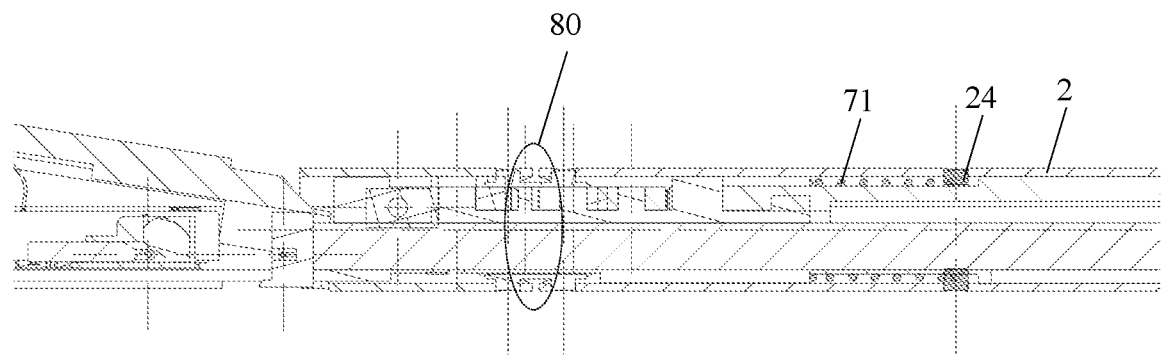
FIG. 8 is a partial schematic diagram including a first elastic member of a surgical stapler provided by an embodiment of the present disclosure.

FIG. 8 is a partial schematic diagram including a first elastic member 71 of a surgical stapler 100 provided by an embodiment of the present disclosure. For example, as shown in FIG. 8, the surgical stapler 100 further includes a first elastic member 71; the first elastic member 71 is connected with the closing mechanism. In the closing stage, the closing mechanism moves toward the end effector 1 to close the end effector 1 and elastically deform the first elastic member 71; after the surgical fastener pushing stage, the closing mechanism moves away from the end effector 1 under the action of an elastic restoring force applied by the elastically deformed first elastic member 71.

The first elastic member 71 is deformed under an external load, and has an original shape and size completely restored as deformation completely disappears after the external load is removed. For example, a material of the first elastic member 71 may include some resins or natural materials having elastic compression deformation properties, for example, including but not limited to, thermoplastic elastomer (TPE), thermoplastic polyurethane (TPU), thermoplastic polyester elastomer (TPEE), or the like. The first elastic member 71 may be made into, for example, a block-shaped elastic member or a hollow cylindrical elastic member. For another example, an elastic compression deformation structure may include certain structures having elastic compression deformation properties, for example, compression springs, zigzag elastic members, organ leaf elastic members, lantern skeleton-shaped elastic members, or the like. The elastic compression deformation structure may be made of materials, for example, including but not limited to, metal, plastic, or ceramic, which are not limited by the embodiments of the present disclosure.

For example, in the embodiment shown in FIG. 8, the sleeve 2 includes a clamp holding structure 24 protruding from the inner wall of the sleeve 2 toward an inner side of the sleeve 2; the first elastic member 71 is located on a side of the clamp holding structure 24 close to the end effector 1, so that the first elastic member 71 is configured to be compressed as the closing mechanism moves toward the end effector 1, so as to compress and limit the first elastic member 71 by fully utilizing the limited space inside the sleeve 2.

For example, in other embodiments, the first elastic member 71 is located on a side of the clamp holding structure 24 close to the end effector 1 to be configured to be stretched as the closing mechanism moves toward the end effector 1, which, in this way, can also achieve the same or similar technical effect as the embodiments illustrated in FIG. 8.

Figure 9:
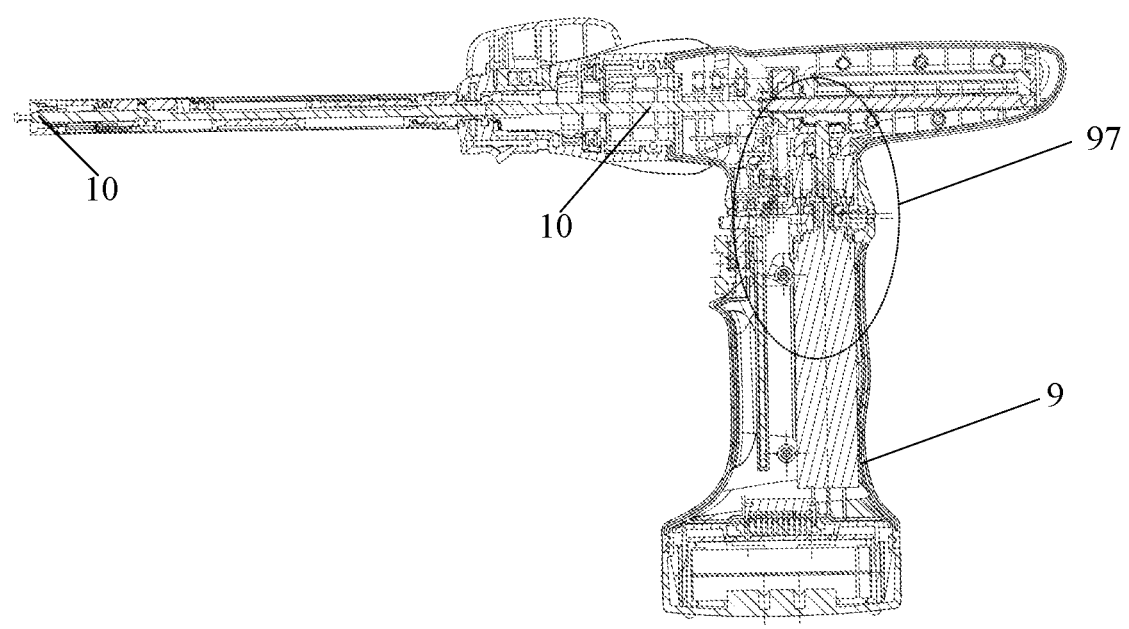
FIG. 9 is a schematic diagram of a main body portion including a first driver mechanism of a surgical stapler provided by an embodiment of the present disclosure.

FIG. 9 is a schematic diagram of a main body portion 4 including the first driver mechanism 10 of the surgical stapler 100 provided by an embodiment of the present disclosure; as shown in FIG. 9, the surgical stapler 100 further includes an electric driver mechanism, the electric driver mechanism is located in the main body portion 4, the main body portion 4 includes, for example, a handle 9 and a driver portion 99 connected with the handle 9; for example, the electric driver mechanism is located in the handle 9 or/and the driver portion 99, the first end of the first driver mechanism 10 is connected with the electric driver mechanism, and the electric driver mechanism drives the first driver mechanism 10 to move along the axial direction. For example, the electric driver mechanism includes a motor and a turbine linkage mechanism that moves as driven by the motor, which may be designed by those skilled in the art according to conventional art, and a structure of the electric driver mechanism is not limited by the present disclosure.

For example, the surgical stapler 100 further includes a cutting device 60a. The fastener-cartridge assembly 11 and the anvil 12 engage with each other to clamp the target tissue; after the surgical fastener pushing assembly pushes the surgical fastener out of the fastener-cartridge assembly 11, the surgical fastener enters the target tissue to suture the target tissue; the first driver mechanism 10 is further configured to drive the cutting device 60a to cut the target tissue. That is, the first driver mechanism 10 is further configured to drive the cutting device 60a to cut the target tissue, which further simplifies the driver mechanism, saves space, and reduces the volume of the surgical stapler 100, so that it is easy to enter the surgical object, for example, the human body, in a surgical procedure, to reduce injuries to the surgical object; in addition, simplification of the driver mechanism makes an operation process of the surgical stapler 100 easier and smoother to be implemented, makes an outstanding contribution to improving reliability of the operation of the surgical stapler 100, and also reduces difficulty in designing a control system for controlling the operation process of the surgical stapler 100. For example, the target tissue is cut after the entire target tissue is sutured. Of course, the target tissue may be cut while being sutured, that is, for each unit portion of the target tissue, the unit portion is sutured firstly, and then the unit portion is cut immediately. A specific suturing and cutting method is introduced below.

For example, the surgical stapler 100 further includes a cutting driver mechanism 40a; the cutting driver mechanism is configured to drive, as driven by the first driver mechanism 10, the cutting device 60a to cut the target tissue. For example, the surgical fastener pushing driver mechanism 40 also serves as the cutting driver mechanism 40a to simplify the structure of the surgical stapler 100 and save space. The second driver mechanism 20 is further configured to be connected with the cutting driver mechanism 40a in the cutting stage to drive the cutting driver mechanism 40a to move, that is, in the case where the surgical fastener pushing driver mechanism 40 also serves as the cutting driver mechanism 40a, the second driver mechanism 20 is further configured to be connected with surgical fastener pushing driver mechanism 40 to drive the surgical fastener pushing driver mechanism 40 to move in the cutting stage.

Figure 12A:
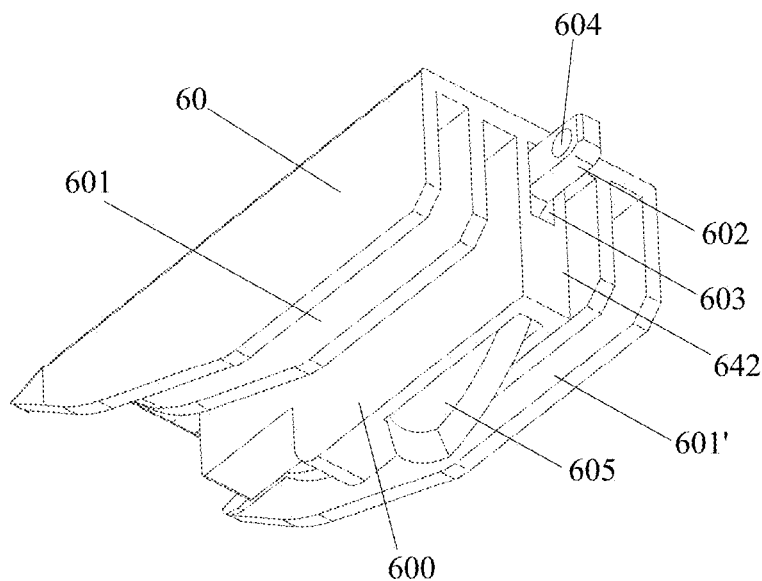
FIG. 12A is a structural schematic diagram of a surgical fastener pushing slide block carrying a cutting blade.

For example, the cutting device 60a includes a blade-carrying member 60b and a cutting blade 605; the cutting blade 605 is in movable connection with the blade-carrying member 60b; and the cutting driver mechanism 40a is configured to drive the blade-carrying member 60b to move so as to drive the cutting blade 605 to move. FIG. 12A is a structural schematic diagram of the surgical fastener pushing slide block carrying the cutting blade; for example, referring to FIG. 12A and FIG. 13A, the surgical fastener pushing slide block 60 serves as the blade-carrying member 60b to further simplify the structure of the surgical stapler 100, save space, and facilitate the driving and the controlling the surgical fastener pushing stage and the cutting stage.

The surgical fastener pushing stage and the cutting stage of the surgical stapler 100 is described below by taking the case where the surgical fastener pushing driver mechanism 40 serves as the cutting driver mechanism 40a.

In the closing stage during which the first driver mechanism 10 drives the closing mechanism to close the end effector 1 and in the surgical fastener pushing stage during which the surgical fastener pushing assembly is driven to push the surgical fastener out of the fastener-cartridge assembly 11, the first driver mechanism 10 moves toward the end effector 1; for example, in the cutting stage, the first driver mechanism 10 moves away from the end effector 1 to drive the cutting driver mechanism 40a to move away from the end effector 1.

Figure 10A:
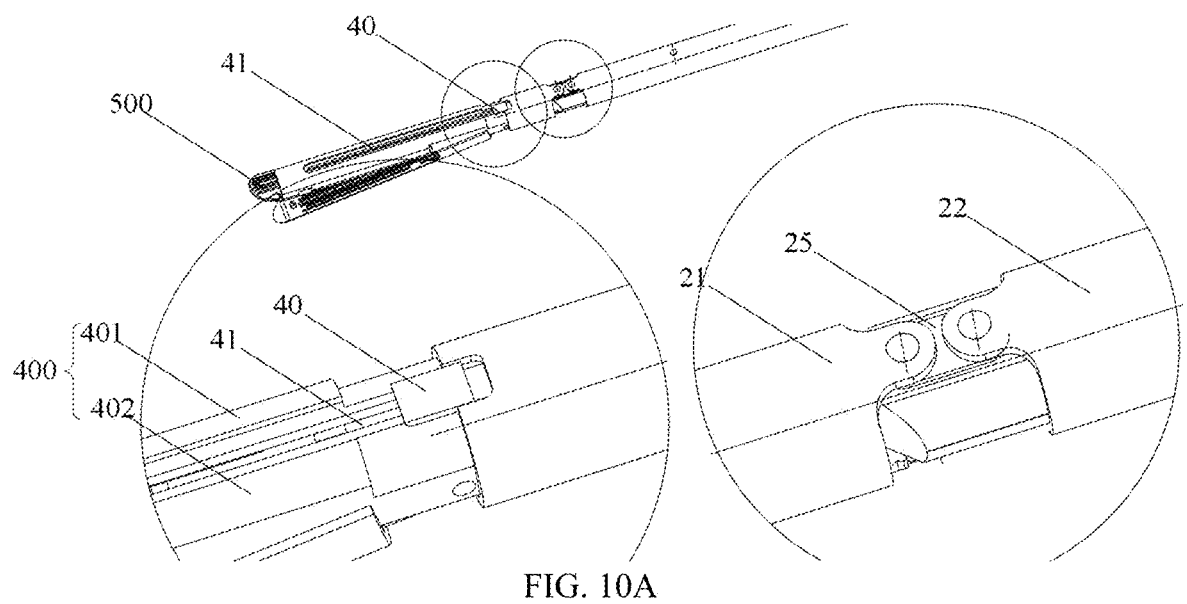
FIG. 10A is a structural relationship diagram of a fastener-cartridge assembly and a surgical fastener pushing driver mechanism.

FIG. 10A is a structural relationship diagram of the fastener-cartridge assembly 11 and the surgical fastener pushing driver mechanism. Referring to FIG. 10A and FIG. 2, the end effector 1 includes a first end and a second end that are opposite to each other in the axial direction, the first end of the end effector 1 is closer to the closing mechanism, that is, the sleeve 2, than the second end of the end effector 1. Before the surgical fastener pushing stage, the cutting device 60a is located at the first end of the end effector 1; in the surgical fastener pushing stage, the first driver mechanism 10 moves along the axial direction toward the end effector 1 to drive the cutting driver mechanism 40a and the surgical fastener pushing slide block 60 to move synchronously toward the end effector 1, the cutting driver mechanism 40a drives the cutting device 60a to move from the first end of the end effector 1 to the second end of the end effector 1, and in the surgical fastener pushing stage, the cutting blade 605 is at least partially in the surgical fastener pushing slide block 60, and the cutting blade 605 has a preset distance to the target tissue clamped between the fastener-cartridge assembly 11 and the anvil 12, so that the cutting blade 605 is not in contact with the target tissue. In the cutting stage, the first driver mechanism 10 moves along the axial direction away from the end effector 1 to drive the cutting driver mechanism 40a to move away from the end effector 1, and the cutting driver mechanism 40a drives the cutting device 60a to move from the second end of the end effector 1 to the first end of the end effector 1 to cut the target tissue.

Figure 10B:
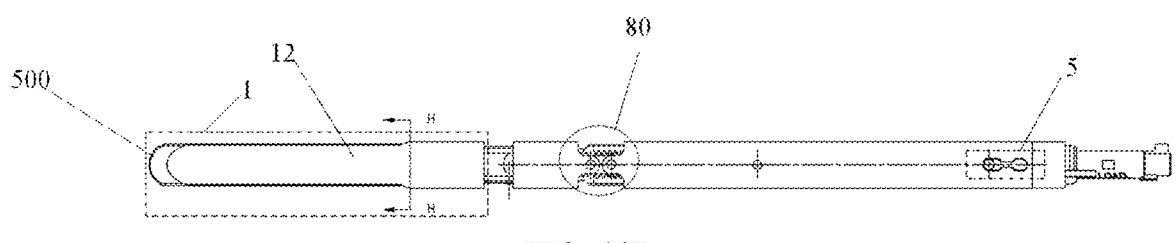
FIG. 10B is a top view of the surgical stapler shown in FIG. 10A in an anvil view direction.
Figure 10C:
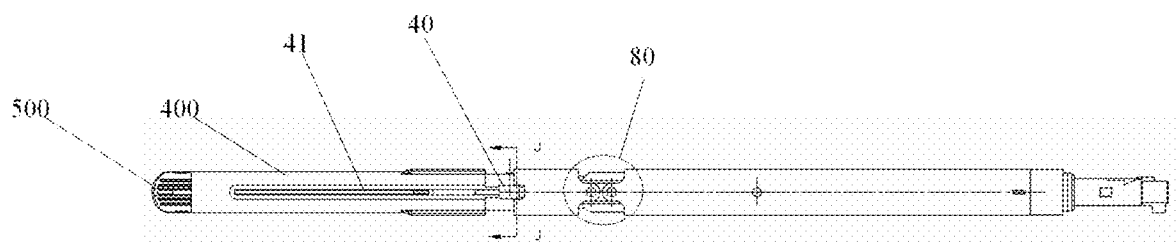
FIG. 10C is a top view of the surgical stapler shown in FIG. 10A in a fastener-cartridge view direction.
Figure 10D:
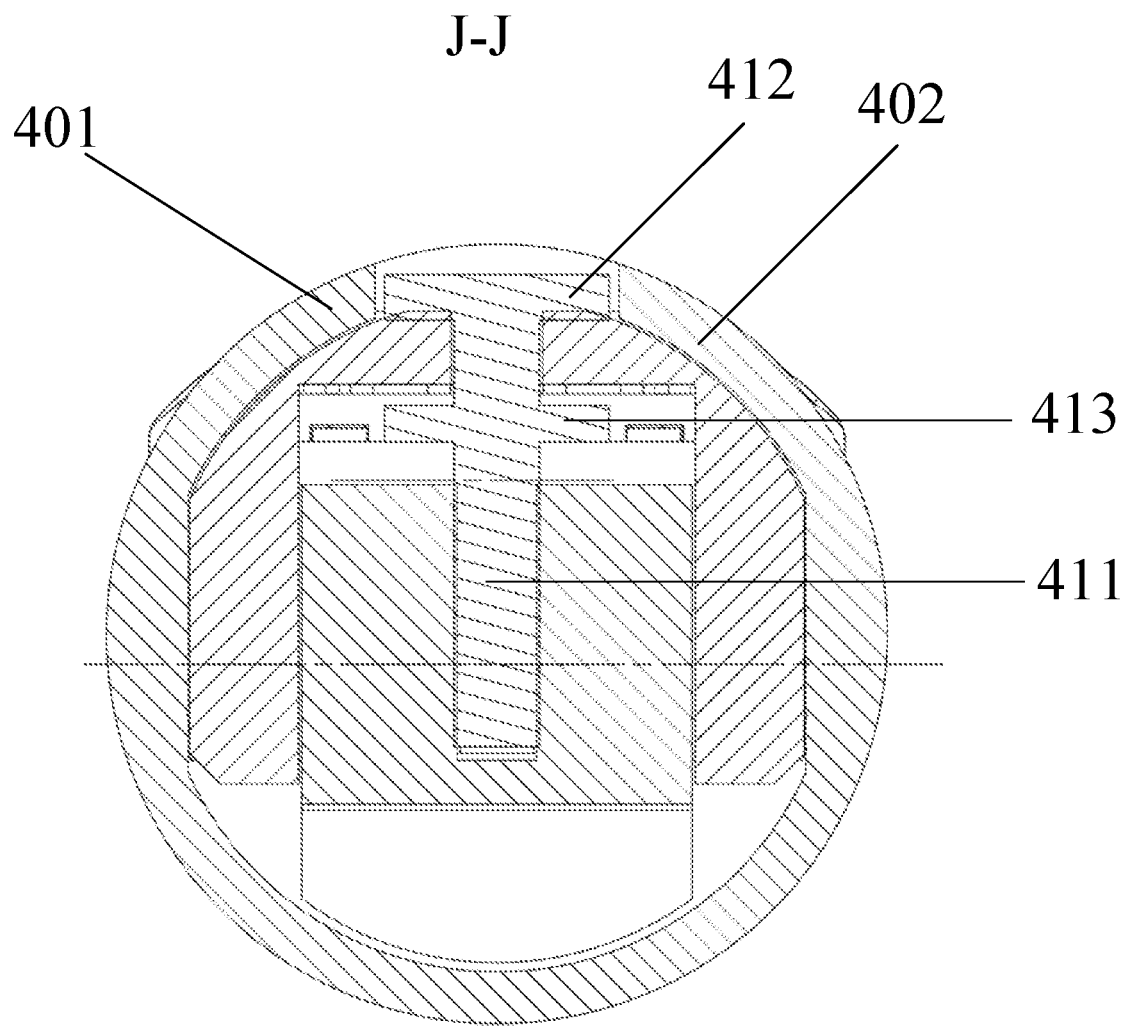
FIG. 10D is a cross-sectional schematic diagram along a line J-J in FIG. 10C.
Figure 10E:
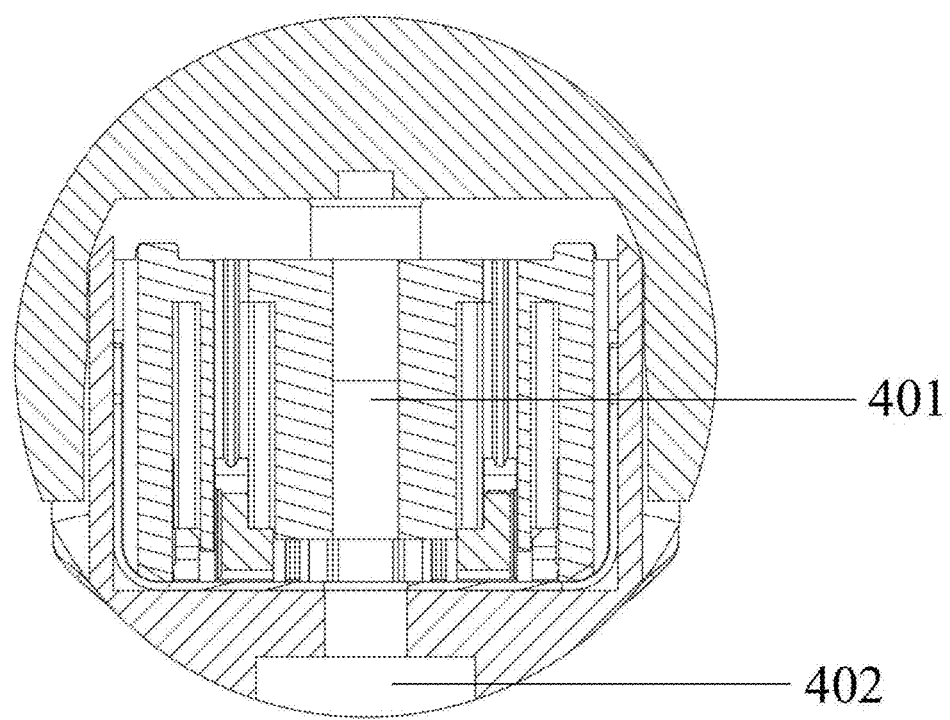
FIG. 10E is a cross-sectional schematic diagram along a line H-H in FIG. 10B.
Figure 12E:
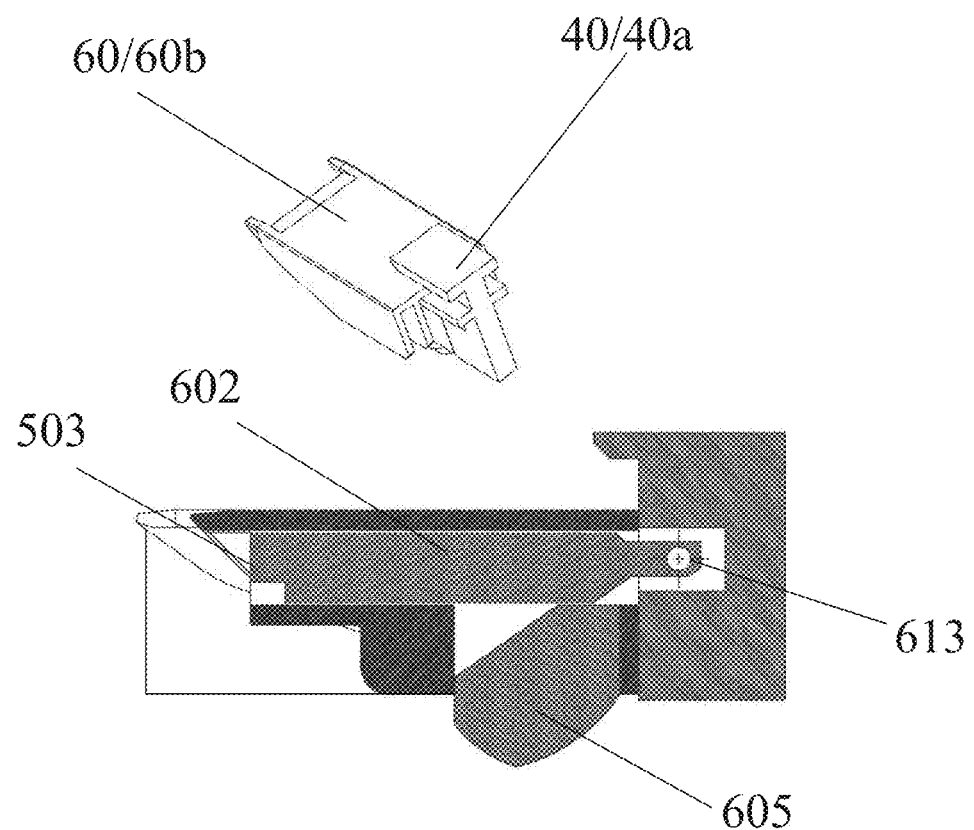
FIG. 12E is a schematic diagram of the cutting driver mechanism and the surgical fastener pushing slide block that are connected with each other.
Figure 13B:
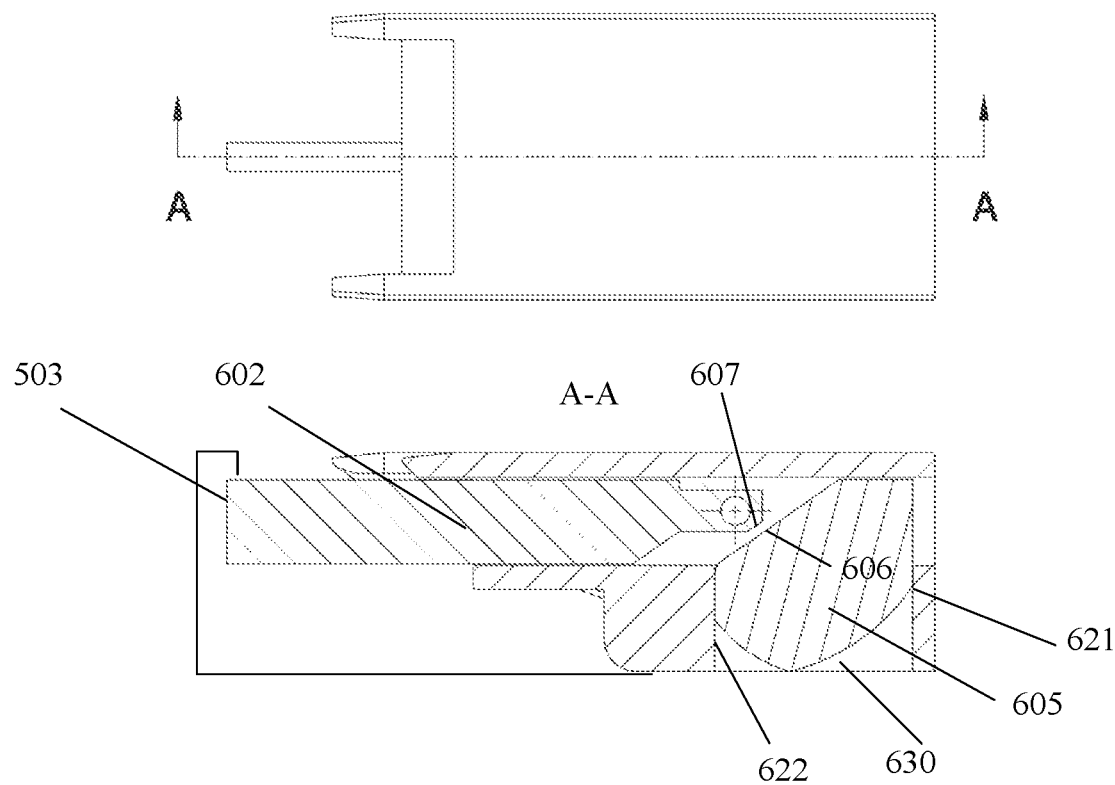
FIG. 13B is a schematic diagram of the cutting blade not in contact with target tissue in the surgical fastener pushing stage.
Figure 13C:
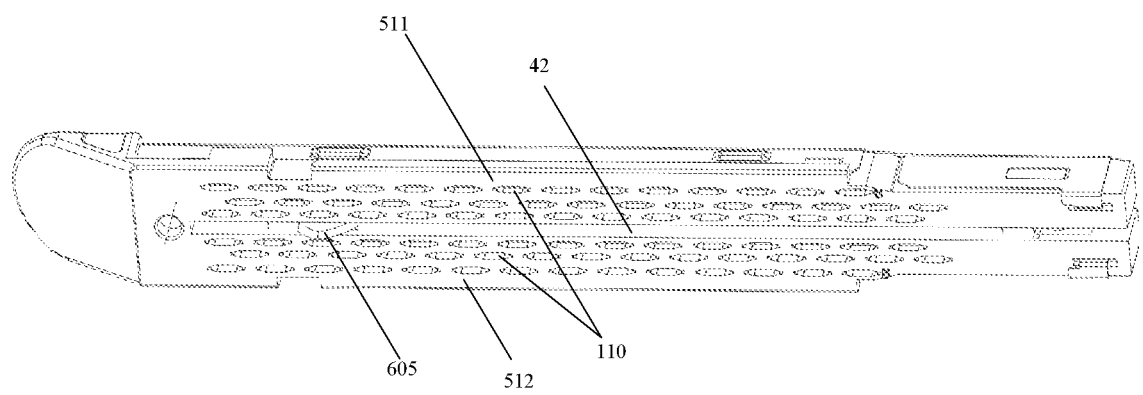
FIG. 13C is a schematic diagram of the process that the surgical fastener pushing slide block carrying the cutting blade moves from a first end of the end effector to a second end of the end effector.

FIG. 10B is a top view of the surgical stapler 100 shown in FIG. 10A in an anvil view direction; FIG. 10C is a top view of the surgical stapler 100 shown in FIG. TOA in a fastener-cartridge view direction; FIG. 10D is a cross-sectional schematic diagram along a line J-J in FIG. 10C; FIG. TOE is a cross-sectional schematic diagram along a line H-H in FIG. 10B; FIG. 12E is a schematic diagram of connection between the cutting driver mechanism 40a and the surgical fastener pushing slide block that are connected with each other; and FIG. 13C is a schematic diagram of movement of the surgical fastener pushing slide block 60 carrying the cutting blade 605 from the first end of the end effector 1 to the second end of the end effector 1. Referring to FIG. 10A, FIG. 10B-10E, FIG. 12E and FIG. 13C, the fastener-cartridge assembly 11 includes a fastener-cartridge 500 and an outer bracket 400. The surgical fasteners are provided inside the fastener-cartridge 500; the outer bracket 400 is fixed on the fastener-cartridge 500 and has a first portion and a second portion that are opposite to each other; the first portion and the second portion are located on a side of the fastener-cartridge away from the anvil 12 and both extend along the axial direction; the first portion 401 of the outer bracket 400 and the second portion 402 of the outer bracket 400 are spaced apart from each other to define a first chute 41 extending along the axial direction; and each of the first portion 401 of the outer bracket 400 and the second portion 402 of the outer bracket 400 have an upper surface away from the fastener-cartridge 500 and a lower surface opposite to the respective upper surface. The surgical fastener pushing driver mechanism 40 includes a main body portion 411 and a first sliding portion 412. In a process that the surgical fastener pushing driver mechanism 40 drives the surgical fastener pushing slide block 60 to move, the main body portion 411 is configured to be connected with the blade-carrying member 60b, that is, the surgical fastener pushing slide block 60, and the first end of the main body portion 411 away from the anvil 12 slides in the first chute 41. The first sliding portion 412 is connected with the main body portion 411, is supported on the upper surface of the first portion of the outer bracket 400 and the upper surface of the second portion of the outer bracket 400, and is configured to be able to slide along the upper surface of the first portion of the outer bracket 400 and the upper surface of the second portion of the outer bracket 400. In this way, the surgical fastener pushing driver mechanism 40 is arranged on the fastener-cartridge, and the outer bracket 400 can ensure that the surgical fastener pushing driver mechanism 40 moves stably in the surgical fastener pushing stage, so that in the surgical fastener pushing stage, the surgical fastener pushing driver mechanism 40 can be free from the force of the anvil 12, so that the surgical fastener pushing driver mechanism 40, that is, the cutting driver mechanism 40a, has a preset distance to the target tissue clamped between the fastener-cartridge 11 and the anvil 12, to make the cutting blade 605 not be in contact with the target tissue.

For example, as shown in FIG. 13C, the fastener-cartridge includes a fastener-cartridge bracket; the fastener-cartridge bracket includes a first portion 511 and a second portion 512 that extend along the axial direction; each of the first portion 511 and the second portion 512 of the fastener-cartridge bracket includes a surgical fastener slot 110 for accommodating the surgical fastener, and the first portion 511 and the second portion 512 define a second chute 42 extending along the axial direction. The second chute 42 is opposite to the first chute 41; in a process that the surgical fastener pushing driver mechanism 40 drives the surgical fastener pushing slide block 60 to move, the second end of the main body portion 411 of the surgical fastener pushing driver mechanism 40 close to the anvil 12 slides in the second chute 42.

For example, the fastener-cartridge has a fastener out-put surface opposite to the anvil 12; and a cross section of an entire body constituted by the main body portion 411 of the surgical fastener pushing driver mechanism 40 and the first sliding portion 412 in a direction perpendicular to the fastener out-put surface is T-shaped. In this way, different from a surgical fastener pushing driver mechanism 40 (the cutting driver mechanism 40a) in a shape of "T", the T-shaped surgical fastener pushing driver mechanism 40 is arranged on the fastener-cartridge, and an end of the T-shaped pushing driver mechanism close to the anvil 12, that is, the end of the T-shaped pushing driver mechanism close to the target tissue, may be separated from the target tissue by a preset distance in the surgical fastener pushing stage, so that the cutting blade 605 is not in contact with the target tissue, and the target tissue is cut after the entire target tissue is sutured, which is favorable for smoothly and accurately suturing the target tissue, as well as accurately cutting the target tissue.

For example, as shown in FIG. 10D, the surgical fastener pushing driver mechanism 40 further includes a second sliding portion 413; the second sliding portion 413 is connected with the main body portion 411, is located on a side of the first portion 401 and the second portion 402 away from the first sliding portion 412, is in contact with the lower surface of the first portion 402 and the lower surface of the second portion 402, and is configured to be able to slide along the lower surface of the first portion 402 and the lower surface of the second portion 402.

FIG. 13A is a schematic diagram of the surgical fastener pushing process. As shown in FIG. 12A and FIG. 13A, the surgical fastener pushing pieces 700 are arranged along the axial direction and are configured to apply a surgical fastener pushing pressure to the surgical fasteners to push the surgical fasteners out of the fastener-cartridge; the surgical fastener pushing slide block 60 is configured to apply pressure to the surgical fastener pushing piece 700 to drive the surgical fastener pushing piece 700 to apply the surgical fastener pushing pressure to the staple; the surgical fastener pushing driver mechanism 40 is configured to drive the surgical fastener pushing slide block 60 to move along the axial direction as driven by the first driver mechanism 10 in the surgical fastener pushing stage, so that the surgical fastener pushing slide block 60 is sequentially in contact with the surgical fastener pushing pieces 700 along the axial direction, so as to apply surgical fastener pushing pressure to the surgical fastener pushing pieces 700.

As shown in FIG. 12A, for example, the surgical fastener pushing slide block 60 includes a main body portion and a surgical fastener pushing chute 601. The surgical fastener pushing chute 601 is located on the main body portion of the surgical fastener pushing slide block 60, is on a side of the main body portion of the surgical fastener pushing slide block 60 that faces the anvil 12, is configured to accommodate the surgical fastener pushing pieces 700 in the surgical fastener pushing stage when the surgical fastener pushing slide block 60 moves along the axial direction, and includes a bottom face facing the anvil 12; the bottom face is configured to apply a surgical fastener pushing pressure to the surgical fastener pushing pieces 700 in the surgical fastener pushing stage.

As shown in FIG. 12A, for example, the surgical fastener pushing slide block 60 includes an accommodating cavity 600; and the cutting blade 605 is at least partially located in the accommodating cavity 600. The surgical fastener pushing slide block 60 includes a first surgical fastener pushing chute 601 and a second surgical fastener pushing chute 601'. The surgical fastener pushed out by the first surgical fastener pushing chute 601 enter into the surgical fastener slot of the first portion of the fastener-cartridge bracket, and the surgical fastener pushed out by the second surgical fastener pushing chute 601' enter into the surgical fastener slot of the second portion of the fastener-cartridge bracket; and the accommodating cavity 600 is located between the first surgical fastener pushing chute 601 and the second surgical fastener pushing chute 601', so that a wall of the accommodating cavity 600 may be also used to form the surgical fastener pushing chute 601, which fully utilizes the limited space of the surgical fastener pushing slide block 60, so that the surgical fastener pushing slide block 60 has functions of carrying the cutting blade 605 and having a plurality of surgical fastener pushing chutes 601 at the same time.

Figures 1, 12B:
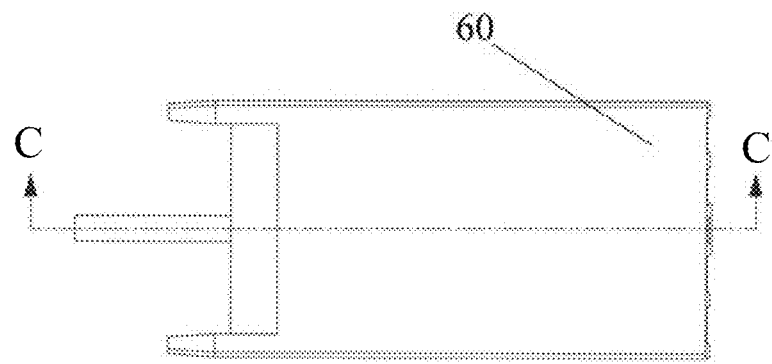
FIG. 12B includes FIG. 12B-1 and FIG. 12B-2.
Figures 2, 12B:
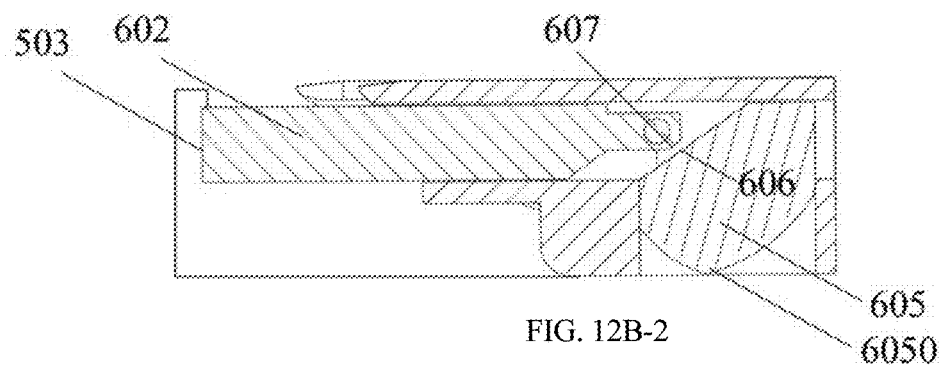

FIG. 12A is an overall structural schematic diagram of the surgical fastener pushing slide block 60 carrying the cutting blade 605; and FIG. 12B is a cross-sectional schematic diagram of the surgical fastener pushing slide block 60 carrying the cutting blade 605. As shown in FIG. 12A to FIG. 12B, for example, the surgical fastener pushing slide block 60, that is, the blade-carrying member 60b includes an accommodating cavity 600, a position limit structure and a blade ejection driver mechanism 602. The cutting blade 605 is at least partially located in the accommodating cavity 600 and includes a cutting edge 6050; the position limit structure is configured to movably connect the cutting blade 605 to the surgical fastener pushing slide block 60; FIG. 13B is a schematic diagram of the cutting blade not in contact with the target tissue in the surgical fastener pushing stage; as shown in FIG. 13B, for example, the accommodating cavity 600 has an inner wall, the inner wall includes a plurality of wall faces 621/622 which at least partially intersect with each other, and the plurality of wall faces 621/622 constitute a position limit structure; in the surgical fastener pushing stage, the plurality of wall faces clamp the cutting blade 605 in a fixed position; a static friction force applied by the plurality of wall faces on the cutting blade 605 is balanced with gravity of the cutting blade, so as to fix the cutting blade 605.

For example, the accommodating cavity 600 includes an opening 630 toward the target tissue; the plurality of wall faces include a first wall face 621 and a second wall face 622 that are opposite to each other, the first wall face 621 and the second wall face 622 intersect with the opening 630 and both intersect with the axial direction; under the action of a first driving force, the cutting blade 605 slides along the first wall face 621 and the second wall face 622 to be exposed from the opening. The blade ejection driver mechanism 602 is configured to apply the first driving force to the cutting blade 605 so that the cutting edge 6050 moves toward the target tissue to be in contact with the target tissue. And the cutting blade 605 is configured to be at least partially exposed from the opening under the action of the first driving force so that the cutting edge 6050 is in contact with the target tissue.

For example, the first wall face 621 and the second wall face 622 are perpendicular to the axial direction, so as to facilitate the cutting blade 605 to subsequently slide toward the target tissue along the first wall face and the second wall face.

Figure 11A:
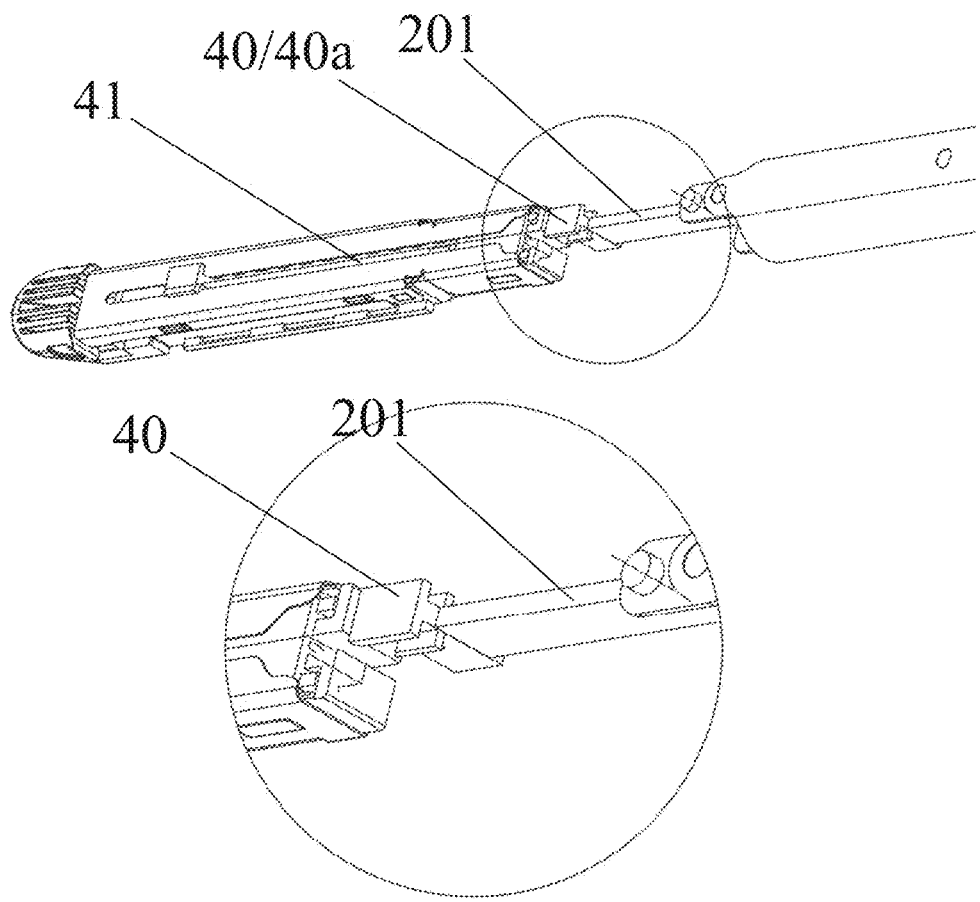
FIG. 11A to FIG. 11B are schematic diagrams of the surgical fastener pushing driver mechanism and a surgical fastener pushing slide block that are not connected with each other.
Figure 11B:
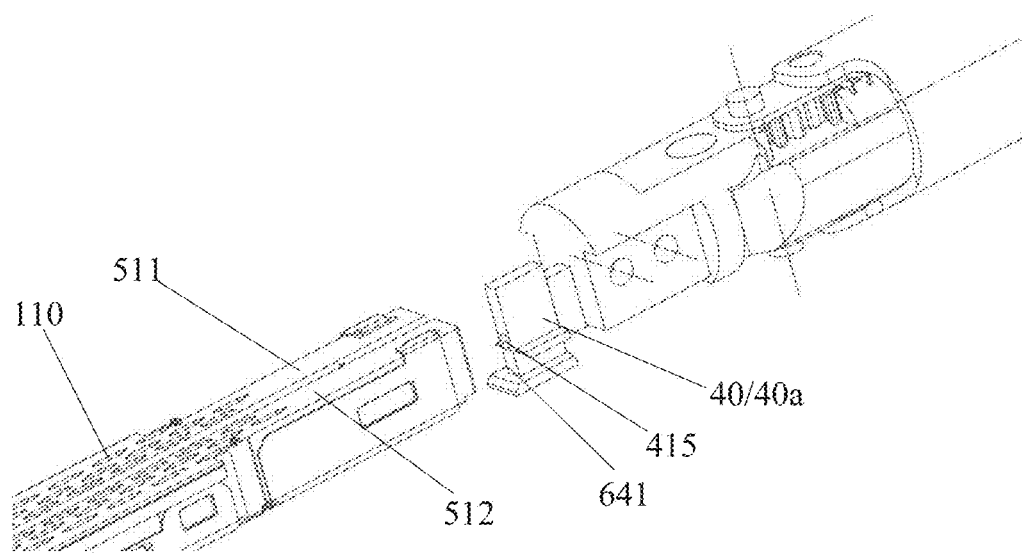
Figure 12C:
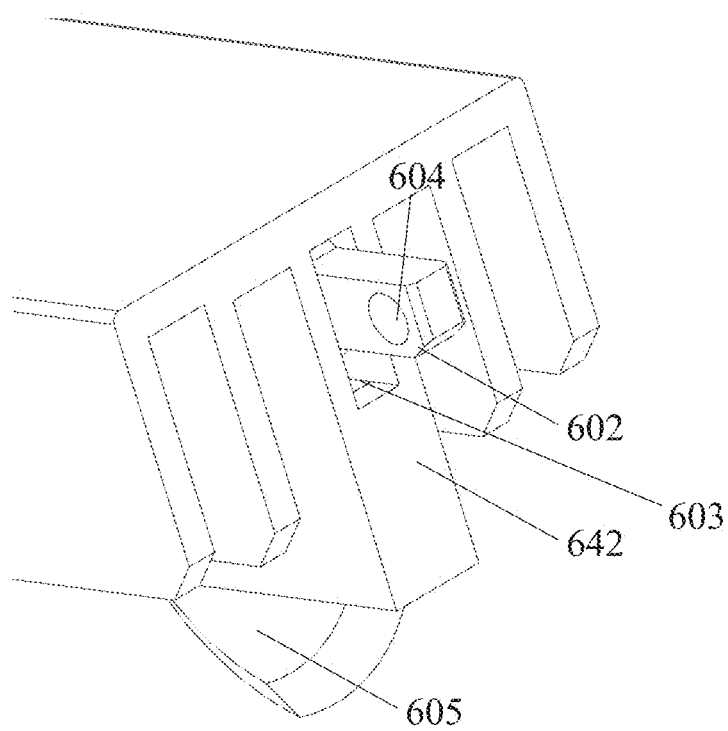
FIG. 12C is a schematic diagram of an end portion of the surgical fastener pushing slide block close to a cutting driver mechanism.
Figure 12D:
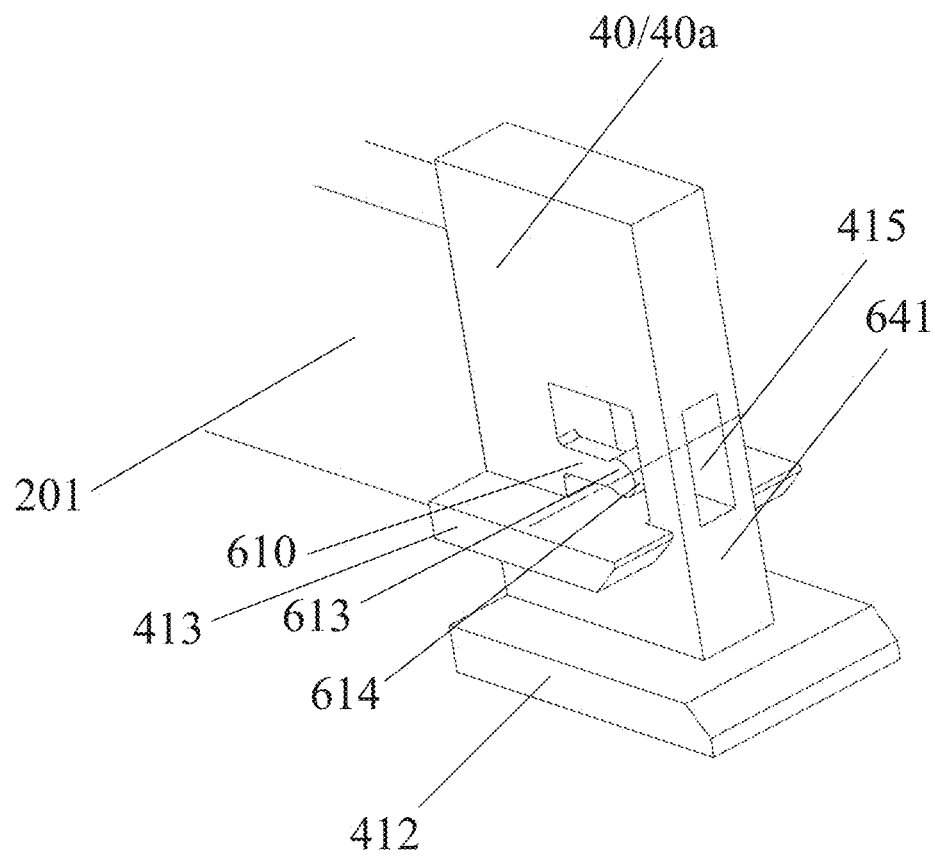
FIG. 12D is a structural schematic diagram of a cutting driver mechanism.

FIG. 11A to FIG. 11B are schematic diagrams of the surgical fastener pushing driver mechanism 40 and the surgical fastener pushing slide block that are not connected with each other. As shown in FIG. 11A to FIG. 11B, for example, before the surgical fastener pushing stage, the surgical fastener pushing driver mechanism 40 is connected with the second driver mechanism 20, and moves with movement of the second driver mechanism 20, to be in contact with the surgical fastener pushing slide block 60, and be connected with the surgical fastener pushing slide block 60. FIG. 12C is a schematic diagram of an end portion of the surgical fastener pushing slide block 60 close to the cutting driver mechanism 40a; FIG. 12E is a schematic diagram of connection between the cutting driver mechanism 40a and the surgical fastener pushing slide block 60 that are connected with each other. In conjunction with FIG. 12C to FIG. 12E, the surgical fastener pushing slide block 60, that is, the blade-carrying member 60b further includes a first connection structure; and the main body portion of the surgical fastener pushing driver mechanism 40 includes a second connection structure. In the surgical fastener pushing stage, the first connection structure is not connected with the second connection structure; after the surgical fastener pushing stage and before the cutting stage, the first connection structure is connected with the second connection structure. For example, as illustrated in FIG. 11B and FIG. 12C-12D, the main body portion of the surgical fastener pushing driver mechanism 40 further includes a force applying face 641 facing the blade-carrying member 60b; and the surgical fastener pushing slide block 60 includes a force bearing face 642 facing the main body portion. In the surgical fastener pushing stage, the cutting driver mechanism 40a moves toward the blade-carrying member 60b so that the force applying face 641 is in contact with the force bearing face 642, and the surgical fastener pushing driver mechanism 40 applies a second driving force to the force bearing face 642 through the force applying face 641 to drive the blade-carrying member 60b to move.

Figure 13D:
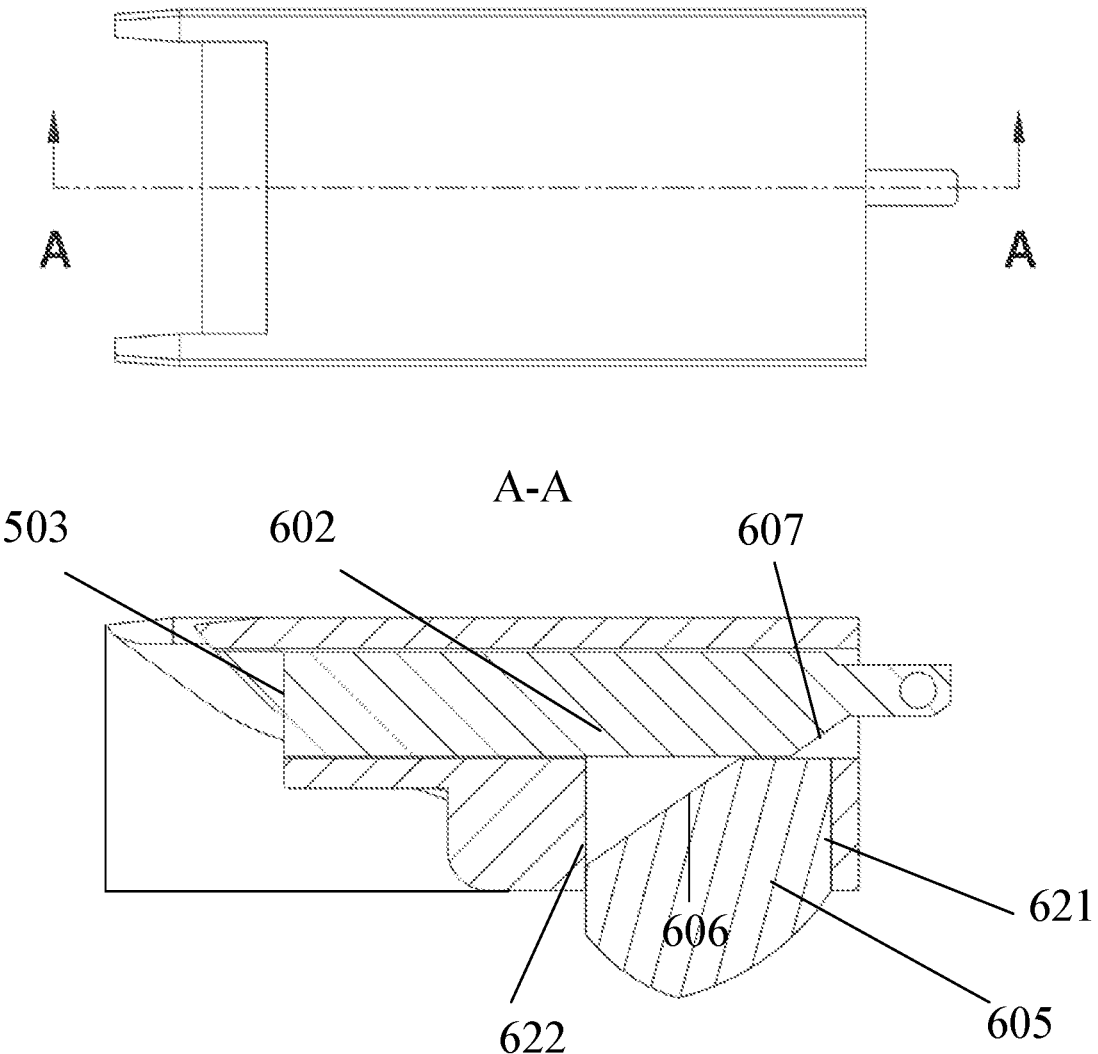
FIG. 13D is a schematic diagram of the process that the cutting blade moves to be in contact with the target tissue in the surgical fastener pushing stage.

For example, in this embodiment, the first connection structure also serves as the blade ejection driver mechanism 602; the blade ejection driver mechanism 602 is at least partially located in the accommodating cavity 600 and is configured to be movable along the axial direction; the blade ejection driver mechanism 602 extends along the axial direction, and includes a first end close to the cutting driver mechanism 40a in the axial direction and a second end opposite to the first end; as shown in FIG. 12A and FIG. 12C, the surgical fastener pushing slide block 60 includes a via hole 603 passing through the force bearing face 642 and in communication with the accommodating cavity 600; in the surgical fastener pushing stage, the first end of the blade ejection driver mechanism 602 is located in the accommodating cavity 600, the second end of the blade ejection driver mechanism 602 extends to the outside of the accommodating cavity 600, and the blade ejection driver mechanism 602 does not move relative to the cutting blade 605 along the axial direction. FIG. 13B is a schematic diagram of the cutting blade not in contact with a target tissue in the surgical fastener pushing stage; and FIG. 13D is a schematic diagram of the cutting blade moving to be in contact with the target tissue in the surgical fastener pushing stage. In conjunction with FIG. 12C to FIG. 12E, FIG. 13C and FIG. 13D, for example, the fastener-cartridge bracket includes a resistance face 503, the resistance face 503 faces the blade ejection driver mechanism 602, and the blade ejection driver mechanism 602 is configured to hit the resistance face 503 when the cutting device 60a reaches the second end of the end effector 1 as driven by the cutting driver mechanism 40a, so that the resistance face 503 applies a blade ejection driving force on the blade ejection driver mechanism 602; and the blade ejection driver mechanism 602 is configured to be in contact with the cutting blade 605 under the action of the blade ejection driving force to apply a first driving force to the cutting blade 605 to drive the cutting blade 605 to move toward the target tissue. For example, as shown in FIG. 13B, when the cutting device 60a reaches the second end of the end effector 1, the second end of the blade ejection driver mechanism 602 hits the resistance face 503, so that the resistance face 503 applies the blade ejection driving force to the blade ejection driver mechanism 602, and the blade ejection driver mechanism 602, under the action of the blade ejection driving force, moves away from the second end of the end effector 1 along the axial direction to be in contact with the cutting blade 605 to apply the first driving force to the cutting blade 605 to drive the cutting blade 605 to move toward the target tissue, and the first end of the blade ejection driver mechanism 602 moves to the outside of the accommodating cavity 600 through the via hole 603 to be connected with the second connection structure, that is, the state shown in FIG. 13B changes to the state shown in FIG. 13D.

In the surgical fastener pushing stage, as shown in FIG. 13B, the cutting edge 6050 of the cutting blade 605 faces the target tissue, the cutting blade 605 further includes a first slope 606 intersecting with the cutting edge 6050, the blade ejection driver mechanism 602 includes a second slope 607, the second slope 607 is located on a side of the first slope 606 away from the cutting edge 6050, is located on a side of the first slope 606 that is close to the second end of the end effector 1 in the axial direction, and is parallel to the first slope 606, and both the first slope 606 and the second slope 607 intersect with the axial direction; when the second end of the blade ejection driver mechanism 602 hits the resistance face 503, the blade ejection driver mechanism 602 is configured to move away from the second end of the end effector 1 along the axial direction under the action of the blade ejection driving force, so that the second slope 607 is in contact with the first slope 606 of the cutting blade 605 to apply a first driving force to the cutting blade 605; while the blade ejection driver mechanism 602 moves away from the second end of the end effector 1 along the axial direction, the cutting blade 605 moves toward the target tissue and the first slope 606 slides toward the target tissue relative to the second slope 607. In this way, it may be ensured that the blade ejection driver mechanism 602 is smoothly connected with the second connection structure, which ensures operation stability, and fully utilizes the limited space of the accommodating cavity 600, saves space, and is favorable for miniaturizing the surgical stapler 100 to minimize a radial size of the surgical stapler 100, so that it is easy for the surgical stapler 100 to enter the surgical object, for example, the human body, in a surgical procedure, thereby reducing injuries to the surgical object.

For example, an included angle between the second slope 607 and a direction which is from the second slope 607 to the second end of the end effector 1 along the axial direction, is an obtuse angle, so as to facilitate the first slope 606 to slide along the second slope 607.

As shown in FIG. 12D to FIG. 12E, the main body portion of the cutting driver mechanism 40a includes a hollow region; the hollow region runs through the force applying face 641 so that the force applying face 641 has a via hole 415; the second connection structure is located in the hollow region; and the second end of the blade ejection driver mechanism 602 passes through the via hole 415 and enters the hollow region to be connected with the second connection structure.

In conjunction with FIG. 12C to FIG. 12E, for example, the second connection structure includes an elastic connection piece, the elastic connection piece protrudes from an inner wall of the hollow region that faces the second end of the blade ejection driver mechanism 602; the second end of the blade ejection driver mechanism 602 has a nestification hole 604. The elastic connection piece includes an elastic connection rod 610 and an end protrusion 613; the elastic connection rod 610 protrudes from the inner wall of the hollow region that faces the second end of the blade ejection driver mechanism 602 and extends along the axial direction; the end protrusion 613 is located on an end of the elastic connection rod 610 away from the inner wall and protrudes from the elastic connection rod 610 along the second direction perpendicular to the axial direction; and the end protrusion 613 is nested in the nestification hole 604 so that the second end of the blade ejection driver mechanism 602 is connected with the elastic connection piece.

As shown in FIG. 12E, for example, an end face of the end protrusion 613 that protrudes from the elastic connection rod 610 is an arc-shaped face 614, and the blade ejection driver mechanism 602 and the elastic connection piece are configured that when the blade ejection driver mechanism 602 moves away from the second end of the end effector 1 along the axial direction under the action of the blade ejection driver mechanism 602 to reach the end protrusion 613, the second end of the blade ejection driver mechanism 602 abuts against the arc-shaped face to make the elastic connection rod 610 elastically deformed in the second direction; and then when the blade ejection driver mechanism 602 continues to move away from the second end of the end effector 1 along the axial direction under the action of the blade ejection driving force so that the nestification hole 604 is opposite to the end protrusion 613, under the action of an elastic restoring force of the elastic connection rod 610, the end protrusion 613 moves along the second direction toward the nestification hole 604 and is nested into the nestification hole 604 so that the surgical fastener pushing driver mechanism 40 (i.e., the cutting driver mechanism 40a) is connected with the surgical fastener pushing slide block 60 (i.e., the blade-carrying member 60b). Such design can fully utilize the part, i.e., the blade ejection driver mechanism 602, which can be used to drive the cutting blade 605 to be exposed to cut the target tissue, and meanwhile, can also be quickly connected with the surgical fastener pushing driver mechanism 40, to prepare for the subsequent cutting stage of driving the cutting blade 605 to move for cutting, in addition, the structure is simple, easy to be implemented, and saves space.

For example, the arc-shaped face 614 is a spherical cap face, and the nestification hole 604 is substantially circular, so that the end protrusion 613 can more easily enter the nestification hole 604 to realize the connection between the second end of the blade ejection driver mechanism 602 and the blade-carrying member 60b, increasing reliability of the device.

Of course, in other embodiments, the second end of the blade ejection driver mechanism 602 may be connected by other forms, such as hooking forms, clamp connection, magnetic connection, etc.; a specific connection mode is not limited by the embodiments of the present disclosure, as long as the above-described effect can be achieved.

For example, in the surgical stapler 100 provided by at least one other embodiment, the surgical fastener pushing slide block, that is, the blade-carrying member, includes a first connection structure, and the main body portion of the cutting driver mechanism includes a second connection structure; at least in the surgical fastener pushing stage and the cutting stage, the first connection structure is connected with the second connection structure so that the surgical fastener pushing driver mechanism, that is, the cutting driver mechanism, is connected with the surgical fastener pushing slide block. That is, the surgical fastener pushing driver mechanism is connected with the surgical fastener pushing slide block in the surgical fastener pushing stage. Besides, for example, the first connection structure includes a first connection end close to the cutting driver mechanism, and the second connection structure includes a second connection end close to the first connection structure. Before the surgical fastener pushing stage, the surgical fastener pushing driver mechanism (i.e., the cutting driver mechanism) is not connected with the blade-carrying member; in the surgical fastener pushing stage, as driven by the first driver mechanism and the second driver mechanism, the surgical fastener pushing driver mechanism moves toward the surgical fastener pushing slide block (i.e., the blade-carrying member) so that the first connection end is connected with the second connection end. For example, the main body portion of the surgical fastener pushing driver mechanism further includes a force applying face facing the blade-carrying member, and the blade-carrying member includes a force bearing face facing the main body portion; in the surgical fastener pushing stage, the cutting driver mechanism moves toward the blade-carrying member so that the force applying face is in contact with the force bearing face, and the first connection end is connected with the second connection end; and the cutting driver mechanism applies a second driving force to the force bearing face through the force applying face, and applies a third driving force to the first connection structure through the second connection structure to drive the blade-carrying member to move. In this embodiment, a position of the end protrusion may be interchanged with a position of the nestification hole. For example, the main body portion of the cutting driver mechanism includes a hollow region, the hollow region runs through the force applying face so that the force applying face has a via hole, the second connection structure is located in the hollow region, and the first connection end passes through the via hole and enters the hollow region to be connected with the second connection end of the second connection structure. For example, the second connection structure includes an elastic connection piece, the elastic connection piece protrudes from the inner wall of the hollow region that faces the first connection end; the end of the elastic connection piece away from the inner wall is the second connection end, and the second connection end has a nestification hole. The elastic connection piece includes: an elastic connection rod and an end protrusion; the elastic connection rod protrudes from the inner wall of the hollow region that faces the first connection end and extends along the axial direction; the end protrusion is located at one end of the elastic connection rod away from the inner wall and protrudes from the elastic connection rod in the second direction perpendicular to the axial direction, the end protrusion is nested in the nestification hole so that the second end of the blade ejection driver mechanism is connected with the elastic connection piece. For example, the end face of the end protrusion that protrudes from the elastic connection rod is an arc-shaped face, and the cutting driver mechanism and the elastic connection piece are configured such that: when the cutting driver mechanism moves, as driven by the first driver mechanism, along the axial direction toward the second end of the end effector to reach the first connection end, the first connection end abuts against the arc-shaped face to make the elastic connection rod elastically deformed in the second direction; and when the cutting driver mechanism, as driven by the first driver mechanism, continues to move along the axial direction toward the second end of the end effector so that the nestification hole is opposite to the end protrusion, the end protrusion moves, under the action of the elastic restoring force of the elastic connection rod, toward the nestification hole along the second direction so that the elastic connection rod is nested in the nestification hole, so that the first connection end is connected with the second connection end. The second connection structure includes an elastic connection piece, the elastic connection piece protrudes from the inner wall of the hollow region that faces the second end of the blade ejection driver mechanism and extends along the axial direction; an end of the elastic connection piece away from the inner wall is a second connection end, and the second connection end has a nestification hole. The second end of the blade ejection driver mechanism has an end protrusion, and the end protrusion protrudes from the second end of the blade ejection driver mechanism along the second direction perpendicular to the axial direction; the end protrusion is nested in the nestification hole so that the second end of the blade ejection driver mechanism is connected with the elastic connection piece. The end face of the end protrusion that protrudes from the second end of the blade ejection driver mechanism is an arc-shaped face, and the blade ejection driver mechanism and the elastic connection piece are configured such that: when the blade ejection driver mechanism moves, under the action of the blade ejection driving force, away from the second end of the end effector so that the elastic connection piece reaches the end protrusion, the elastic connection piece abuts against the arc-shaped face to make the elastic connection piece elastically deformed in the second direction, and when the blade ejection driver mechanism continues to move, under the action of the blade ejection driving force, away from the second end of the end effector along the axial direction so that the nestification hole is opposite to the end protrusion, the elastic connection piece moves, under the action of the elastic restoring force of the elastic connection rod, toward the nestification hole along the second direction, so that the end protrusion is nested into the nestification hole to make the cutting driver mechanism connected with the blade-carrying member. For example, the arc-shaped face is a spherical cap face, and the nestification hole is substantially circular. This embodiment can achieve similar technical effects as the embodiment shown in FIG. 12C to FIG. 12E.

In at least one embodiment of the present disclosure, in the initial state, the end effector 1 is in an open state; in the closing stage, the closing mechanism is configured to drive the fastener-cartridge assembly 11 and the anvil 12 to engage with each other to close the end effector 1 so that the target tissue is clamped between fastener-cartridge assembly 11 and the anvil 12; in the surgical fastener pushing stage following the closing stage, the surgical fastener pushing assembly is configured to push the surgical fastener out of the fastener-cartridge assembly 11 to suture the target tissue. For example, the surgical stapler 100 further includes a lock mechanism 5, the lock mechanism 5 is configured to limit, in the surgical fastener pushing stage, the closing mechanism at a first position so that the closing mechanism maintains the closed state of the end effector 1, and is configured to, in the initial state, limit the closing mechanism at a second position, to maintain the end effector 1 in an open state to achieve a technical effect of two-way locking, to prevent tissue slippage due to movement of the closing mechanism after the end effector 1 is closed; moreover, in the initial state, the lock mechanism can prevent the end effector 1 from being closed due to movement of the closing mechanism, so as to improve operation stability and reliability of the closing mechanism.

Exemplarily, FIG. 6A to FIG. 6C show a structure of a lock mechanism 5 provided by an embodiment of the present disclosure, and an operation process of the lock mechanism 5 when the closing mechanism closes the end effector 1. In conjunction with FIG. 1 and FIG. 6A to FIG. 6C, the lock mechanism 5 includes a first position limit structure and a second position limit structure. The first position limit structure is configured to limit the closing mechanism at the first position in the surgical fastener pushing stage; the second position limit structure is configured to limit the closing mechanism at the second position in the initial state. The first position limit structure and the second position limit structure may be in arbitrary forms as long as the above-described purpose can be achieved, and are not limited to the situations as described in the foregoing embodiments, which will not be limited by the present disclosure.

For example, as shown in FIG. 8, the surgical stapler 100 further includes a first elastic member 71; and the first elastic member 71 is connected with the closing mechanism. In the closing stage, the closing mechanism moves toward the end effector 1 to close the end effector 1 and make the first elastic member 71 elastically deformed; in the surgical fastener pushing stage, the elastically deformed first elastic member 71, under the action of an elastic restoring force thereof, applies a first resistance force that prevents the closing mechanism from moving toward the end effector 1 to the closing mechanism, the first position limit structure is configured to apply a second resistance force whose direction is opposite to the direction of the first resistance force applied to the closing mechanism, and the first resistance force and the second resistance force are balanced to limit the closing mechanism to the first position; in the initial stage, when the closing mechanism is subjected to a driving force that drives the closing mechanism to deviate from the second position, the second position limit structure is configured to apply a third resistance force to the closing mechanism to balance the driving force so as to limit the closing mechanism at the second position.

The first position limit structure includes a first position limit slot 51 and a first lock member. The first position limit slot 51 has a first side wall, is located on the closing mechanism and is configured to move with the movement of the closing mechanism; in the surgical fastener pushing stage, a first end portion 501 of the first lock member is at least partially limited in the first position limit slot 51 and is in contact with the first side wall of the first position limit slot 51 to apply a fourth resistance force to the first side wall of the first position limit slot 51, so as to apply the second resistance force to the closing mechanism through the first position limit slot 51; and the fourth resistance force and the second resistance force are equal in magnitude and are in a same direction. The second position limit structure includes a second position limit slot 52 and a second lock member. The second position limit slot 52 has a second side wall, is located on the closing mechanism, and is configured to move with movement of the closing mechanism. In the initial stage, a first end portion 501 of the second lock member is at least partially limited in the second position limit slot 52 and is configured to be in contact with the second side wall of the second position limit slot 52 to apply a fifth resistance force to the second side wall of the second position limit slot 52, so as to apply the third resistance force on the closing mechanism through the second position limit slot 52; and the fifth resistance force and the third resistance force are equal in magnitude and have a same direction as the first resistance force. For example, in this embodiment, the closing mechanism is a hollow sleeve 2, and both the first position limit slot 51 and the second position limit slot 52 pass through the sleeve wall of the sleeve 2. In this way, the lock mechanism 5 cannot protrude from the sleeve 2, the sleeve 2 and inner space of the sleeve 2 are used to realize the two-way locking of the sleeve 2, which fully utilizes the limited space inside the sleeve 2, so that it is easy for the surgical stapler to enter the surgical object, for example, the human body, in a surgical procedure, to reduce injuries to the surgical object.

As shown in FIG. 6A to FIG. 6C, for example, in some embodiments, the first lock member and the second lock member are a same common lock member 50. In the closing stage, the first position limit slot 51 and the second position limit slot 52 move relative to the common lock member 50 so that the common lock member 50 is configured to move from the second position limit slot 52 to the first position limit slot 51; when a first end portion 501 of the common lock member 50 is at least partially limited in the first position limit slot 51, the common lock member 50 and the first position limit slot 51 constitute the first lock member; when the first end portion 501 of the common lock member 50 is at least partially limited in the second position limit slot 52, the common lock member 50 and the second position limit slot 52 constitute the second lock member. The common lock member 50 simplifies the structure of the lock mechanism 5, saves space, and facilitates miniaturizing the surgical stapler 100.

For example, the movement direction of the sleeve 2, the first position limit slot 51 and the second position limit slot 52 is the axial direction; along the axial direction, the first position limit slot 51 is located on a side of the second position limit slot 52 away from the end effector 1, to realize the above-described function of the first position limit slot 51.

As shown in FIG. 6A to FIG. 6C, the lock mechanism 5 further includes a channel slot 53, and the channel slot 53 is located between the first position limit slot 51 and the second position limit slot 52 and is in communication with the first position limit slot 51 and the second position limit slot 52. In the closing stage, the common lock member 50 is configured to move from the second position limit slot 52 to the first position limit slot 51 via the channel slot 53. The channel slot 53 passes through the sleeve wall of the sleeve 2.

For example, the common lock member 50 further includes a second end portion 502 opposite to the first end portion 501, and a neck portion 503 connecting the first end portion 501 and the second end portion 502; the channel slot 53 is configured to allow the neck portion 503 to pass through, but not allow the first end portion 501 to pass through, so that in the initial stage, the first end portion 501 cannot pass through the channel slot 53 and is at least partially limited in the second position limit slot 52; and in the surgical fastener pushing stage, the first end portion 501 cannot pass through the channel slot 53 and is at least partially limited in the first position limit slot 51. The direction from the first end portion 501 to the second end portion 502 is the longitudinal direction, the longitudinal direction is perpendicular to the axial direction, and the direction perpendicular to the axial direction and the longitudinal direction is the lateral direction. For example, a width of the channel slot 53 in the lateral direction is less than a width of the first position limit slot 51 in the lateral direction and less than a width of the second position limit slot 52 in the lateral direction; a width of the first end portion 501 in the lateral direction is greater than a width of the neck portion 503 in the lateral direction and is greater than a width of the channel slot 53 in the lateral direction, so that the channel slot 53 allows the neck portion 503 to pass through, but does not allow the first end portion 501 to pass through, and therefore in the initial stage, the first end portion 501 cannot pass through the channel slot 53 and is at least partially limited in the second position limit slot 52, and in the surgical fastener pushing stage, the first end portion 501 cannot pass through the channel slot 53 and is at least partially limited in the first position limit slot 51.

For example, in at least one embodiment of the present disclosure, the lock mechanism further includes a lock driver structure. In the closing stage, the lock driver structure is configured to drive the common lock member to move along the longitudinal direction away from the second end portion so that the first end portion moves out of the second position limit slot, and with the movement of the first position limit slot and the second position limit slot, the neck portion is configured to move from the second position limit slot to the first position limit slot via the channel slot; after the end effector is closed, the lock driver structure is configured to drive the common lock member to move along the longitudinal direction toward the second end portion, so that at least a part of the first end portion moves into the first position limit slot to be limited in the first position limit slot, and at least a part of the first end portion is in contact with the first side wall of the first position limit slot to apply the fourth resistance force to the first side wall.

As shown in FIG. 6A to FIG. 6C, for example, the surgical stapler 100 includes a fixing bracket 8, the sleeve 2 is sleeved on the outer side of the fixing bracket 8; and the first position limit slot 51, the second position limit slot 52 and the channel slot 53 expose the outer surface of the fixing bracket 8. The fixing bracket 8 includes a via hole passing through the outer surface; when at least a part of the first end portion 501 of the common lock mechanism 5 is limited in the first position limit slot 51 or limited in the second position limit slot 52, the second end 502 and at least a part of the neck portion 503 are located in the via hole. For example, the first end portion 501 includes a lower surface facing the fixing bracket 8; when at least a part of the first end portion 501 of the common lock mechanism 5 is limited in the first position limit slot 51 or is limited in the second position limit slot 52, the outer surface of the fixing bracket 8 is in direct contact with the lower surface of the first end portion 501 to support the first end portion 501. The common lock member 50 and the via hole constitute a latch structure.

For example, a length of at least a part of the first end portion 501 in the axial direction is less than a length of the first position limit slot 51 in the axial direction to leave a certain margin, so that the first position limit slot 51 allows at least a part of the first end portion 501 to move in the first position limit slot 51 within a range allowed by the margin to adjust the position of the first end portion 501, so as to play a buffering role when clamping the tissue in the closing stage.

For example, the first side wall of the first position limit slot 51 is in a first arc shape; at least a part of the side surface of the first end portion 501 that is in contact with the first side wall is in a second arc shape; and the first arc shape and the second arc shape have a same curvature, which improves locking stability and reliability of the lock member.

For example, a planar shape of the channel slot 53 is a straight bar shape, to ensure that the common lock member 50 smoothly passes through the channel slot 53 and moves between the first position limit slot 51 and the second position limit slot 52.

Exemplarily, as shown in FIG. 6A to FIG. 6C, for example, the lock driver structure includes a bearing face facing the common lock member 50; the bearing face includes a first surface 01, a first slope face 02, a protrusion surface 03, a second slope face 04 and a second surface 05 arranged sequentially along the axial direction; the first slope face 02 connects the first surface 01 and the protrusion surface 03, the second slope 04 connects the protrusion surface 03 and the second surface 05, a first included angle is between the first slope face 02 and the protrusion surface 03, and a second included angle is between the second slope face 04 and the protrusion surface 03; in the longitudinal direction, a distance from the protrusion surface 03 to the second position limit slot 52 is less than a distance between from the first surface 01 to the second position limit slot 52, and is less than a distance from the second surface 05 to the second position limit slot 52, and a distance from the protrusion surface 03 to the channel slot 53 is less than a distance from the first surface 01 to the channel slot 53 and is less than a distance from the second surface 05 to the channel slot 53, a distance from the protrusion surface 03 to the first position limit slot 51 is less than a distance from the first surface 01 to the first position limit slot 51 and is less than a distance from the second surface 05 to the first position limit slot 51. As shown in FIG. 6A, in the initial stage, the second end portion 502 is located on a side of the first slope face 02 away from the second slope face 04; as shown in FIG. 6B, in the closing stage, the lock driver structure is configured to move along the axial direction relative to the common lock member 50, so that the second end portion 502 moves along the first slope face 02 to the protrusion surface to drive the common lock member 50 to move along the longitudinal direction away from the second end portion 502, and then the second end portion 502 moves sequentially along the protrusion surface and the second slope face 04 to a side of the second slope face 04 away from the first slope face 02, as shown in FIG. 6C, so that the common lock member 50 moves along the longitudinal direction toward the second end portion 502. In the closing stage, the movement of the lock driver structure relative to the common lock member 50 and the movement of the first position limit slot 51 and the second position limit slot 52 relative to the common lock member 50 are synchronized, so that in a process in which the second end portion 502 moves relative to the lock driver structure, the neck portion 503 moves from the second position limit slot 52 to the first position limit slot 51 via the channel slot 53, as shown in FIG. 6C; at this time, at least a part of the first end portion 501 is in contact with a first portion of the first side wall close to the channel slot 53, to apply the fourth resistance force to the first portion 511 of the first side wall, and the first portion 511 of the first side wall faces away from the end effector 1.

For example, in the embodiments shown in FIG. 6A to FIG. 6C, the fixing bracket 8 and the common lock member 50 do not move along the axial direction, and the lock driver structure moves along the axial direction to ensure the stability of the fixing bracket 8 and the common lock member 50.

The first driver mechanism 10 of the surgical stapler 100 is connected with the second driver mechanism 20 and is configured to drive the second driver mechanism to move; in the closing stage, the second driver mechanism 20 is in detachable connection with the closing mechanism and is configured to move, as driven by the first driver mechanism 10, toward the end effector 1, so that the closing mechanism is in contact with the fastener-cartridge assembly 11 and the anvil 12 and applies pressure to the fastener-cartridge assembly 11 and the anvil 12 to close the end effector 1. For example, the lock driver structure is provided on the second driver mechanism 20. For example, in the embodiment shown in FIG. 6A to FIG. 6C, a part of the second driver mechanism 20 serves as the lock driver structure, so as to fully utilize the second driver mechanism 20 and simplify the structure of the surgical stapler 100.

In the surgical fastener pushing stage, the second driver mechanism 20 is separated from the closing mechanism and continues to move toward the end effector 1 to drive the surgical fastener pushing assembly to push the surgical fastener out of the fastener-cartridge assembly 11. As shown in FIG. 6C, the first surface 01 is located at an end of the second surface 05 close to the end effector 1; in the closing stage, during movement of the second end portion 502 relative to the lock driver structure, the first end portion 501 moves from the second position limit slot 52 to the first position limit slot 51; in the surgical fastener pushing stage and the cutting stage, the second end portion 502 moves over the second surface 05 and the second surface 05 is configured not to apply the second end portion with a force that drives the common lock member to move along the longitudinal direction, that is, there is no structure on the second surface 05 such as a boss that can drive the common lock member to move upward along the longitudinal direction, so as to maintain the locking of the sleeve 2 in both the surgical fastener pushing stage and the cutting stage, to ensure a fixed position of the target tissue, so as to ensure accuracy of suturing and cutting.

For example, as shown in FIG. 6A to FIG. 6C, the lock mechanism 5 further includes a second elastic member 72; the second elastic member 72 is configured to be compressed in a process during which the common lock member 50 moves along the longitudinal direction away from the second end portion 502, and be restored under the action of an elastic restoring force thereof in a process during which the common lock member 50 moves along the longitudinal direction close to the second end portion 502, to ensure that the common lock member 50 can quickly move along the longitudinal direction toward the second end portion 502, to return to the via hole, so as to ensure reliability of operation of the lock mechanism 5.

The properties and the materials of the above-described first elastic member 71 may be referred to for properties and materials of the second elastic member 72. For example, the second elastic member 72 is a spring, for example, the second elastic member 72 may be sleeved on the neck portion 503 and be deformed when applied with a force by the fixing bracket 8, for example, be deformed by compression.

For example, as shown in FIG. 6A to FIG. 6C, the second end portion 502 of the common lock member 50 has a cone shape that tapers longitudinally toward the bearing face, in this way, when the second end portion 502 slides along the first slope face 02, a contact area between the second end portion 502 and the first slope face 02 is reduced, so that the second end portion 502 more easily moves to the protrusion surface 03; and when the second surface 05 slides along the protrusion surface 03, the second slope face 04 and the second surface 05, a contact area between the second end portion 502 and the protrusion surface 03, the second slope face 04 and the second surface 05 is reduced, which is favorable for smooth progress of sliding.

For example, the first slope face 02 and the second slope face 04 are flat faces or curved faces, preferably flat faces, which can more easily realize the above-described movement, especially the second end portion 502 can more easily slides along the first slope face 02 to the protrusion surface. Of course, the shapes of the first slope face 02 and the second slope face 04 are not limited by the embodiments of the present disclosure.

For example, with respect to the surgical stapler 100 provided by at least one embodiment of the present disclosure, in an open stage after the surgical fastener pushing stage, the lock mechanism 5 is further configured to remove the limitation on the position of the closing mechanism to open the end effector 1. For example, the limitation on the position of the closing mechanism may be removed at any time by artificial control to open the end effector 1; for example, the open stage is before suturing the tissue, for example, before suturing the tissue, it is necessary to open the end effector 1 to adjust the position of the target tissue clamped; or the open stage may also be after suturing the tissue and cutting the tissue, of course, the end effector 1 may also be opened after suturing the tissue but before cutting the tissue, for example, in some special cases, it is necessary to open the end effector 1 to make adjustments before cutting the tissue.

In the open stage after the surgical fastener pushing stage, the first position limit structure is configured to eliminate the second resistance force, and the closing mechanism moves away from the end effector 1 under the action of the first resistance force so that the fastener-cartridge assembly 11 and the anvil 12 move away from each other to open the end effector 1. In the open stage, the common lock member 50 is configured to move from the first position limit slot 51 to the second position limit slot 52 so that the end effector 1 return the initial state.

For example, in the embodiment shown in FIG. 6A to FIG. 6C, in the open stage, the common lock member 50 is configured to move from the first position limit slot 51 to the second position limit slot 52 via the channel slot 53. In the open stage, the lock driver structure is further configured to drive the common lock member 50 to move along the longitudinal direction away from the second end portion 502 so that the first end portion 501 moves out of the first position limit slot 51; with the movement of the first position limit slot 51 and the second position limit slot 52, the neck portion 503 is configured to move from the second position limit slot 52 to the first position limit slot 51 via the channel slot 53.

In the embodiment shown in FIG. 6A to FIG. 6C, in the open stage, the lock driver structure is configured to move along the axial direction relative to the common lock member 50 so that the second end portion 502 moves along the second slope face 04 to the protrusion surface 03 to drive the common lock member 50 to move along the longitudinal direction away from the second end portion 502, and further the second end portion 502 moves sequentially along the protrusion surface 03 and the first slope face 02 to a side of the first slope face 02 away from the second slope face 04, so that the common lock member 50 moves along the longitudinal direction toward the second end portion 502; in the open stage, the movement of the lock driver structure relative to the common lock member 50 and the movement of the first position limit slot 51 and the second position limit slot 52 relative to the common lock member 50 are synchronized, so that in a process during which the second end portion 502 moves relative to the lock driver structure, the neck portion 503 moves from the first position limit slot 51 to the second position limit slot 52 via the channel slot 53.

For example, as shown in FIG. 8, the first elastic member 71 is located at an end of the lock mechanism 5 close to the end effector 1 and is compressed as the closing mechanism moves toward the end effector 1; or, in other embodiments, the first elastic member 71 is located at an end of the lock mechanism 5 away from the end effector 1 and is stretched as the closing mechanism moves toward the end effector 1.

For example, as shown in FIG. 6A to FIG. 6C, the first position limit slot 51, the second position limit slot 52 and the channel slot 53 are arranged right opposite to the connection hole 23 so that the space inside the sleeve 2 is more uniformly and fully utilized.

Figure 14A:
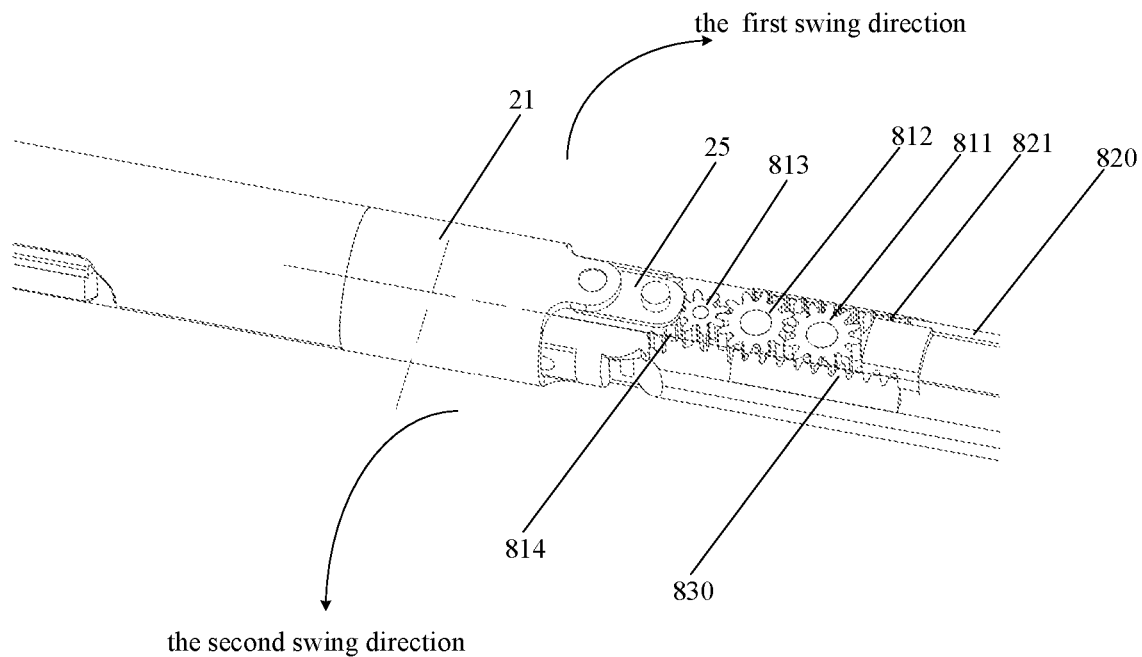
FIG. 14A is a schematic diagram I of a front articulation driver assembly of a surgical stapler provided by an embodiment of the present disclosure.
Figure 14B:
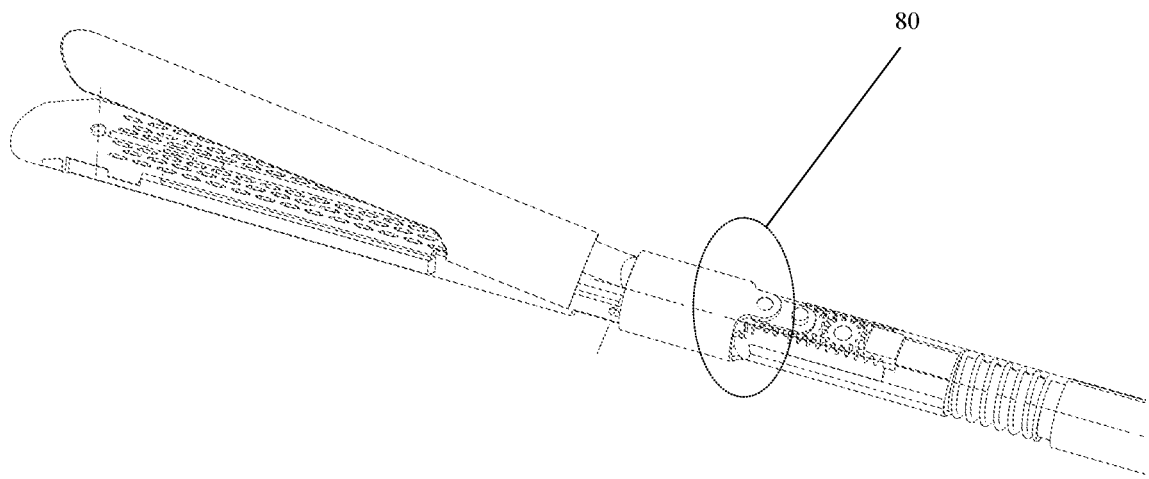
FIG. 14B is a schematic diagram II of a front articulation driver assembly of a surgical stapler provided by an embodiment of the present disclosure.

FIG. 14A is a schematic diagram I of the front articulation driver assembly of the surgical stapler 100 provided by an embodiment of the present disclosure; and FIG. 14B is a schematic diagram II of the front articulation driver assembly of the surgical stapler 100 provided by an embodiment of the present disclosure. In conjunction with FIG. 2 and FIG. 14A to FIG. 14B, for example, the surgical stapler 100 provided by at least one embodiment includes an end effector 1, a closing mechanism, a surgical fastener pushing assembly, a first driver mechanism 10 and an articulation mechanism. The end effector 1 includes a fastener-cartridge assembly 11 and an anvil 12, at least one surgical fastener is provided in the fastener-cartridge assembly 11; the closing mechanism is configured to drive the fastener-cartridge assembly 11 and the anvil 12 to engage with each other to close the end effector 1 so that the end effector 1 clamps the target tissue; the surgical fastener pushing assembly is configured to push the surgical fastener out of the fastener-cartridge assembly 11; the first driver mechanism 10 is configured that in the closing stage, the first driver mechanism 10 is in detachable connection with the closing mechanism to drive the closing mechanism to close the end effector 1; and in the surgical fastener pushing stage following the closing stage, the first driver mechanism 10 is separated from the closing mechanism and drives the surgical fastener pushing assembly to push the surgical fastener out of the fastener-cartridge assembly 11 to suture the target tissue. The articulation mechanism includes a front articulation driver assembly and a rear articulation driver assembly. The front articulation driver assembly and the rear articulation driver assembly are configured to drive the end effector 1 to pivot. As shown in FIG. TA, the surgical stapler 100 includes a main body portion 4 and a detachable portion 3, the detachable portion 3 is in detachable connection with the main body portion 4; the end effector 1 and the front articulation driver assembly are located in the detachable portion 3, the first driver mechanism 10 and the rear articulation driver assembly are located in the main body portion 4; as shown in FIG. TA and FIG. 15A, the detachable portion 3 is in detachable connection with the main body portion 4 to enable the front articulation driver assembly to be in detachable connection with the rear articulation driver assembly. In this way, space of the main body portion 4 is fully utilized to provide the articulation mechanism, and in a case where the detachable portion 3 and the main body portion 4 are detachable, detachable connection of the articulation mechanism is implemented.

Figure 15A:
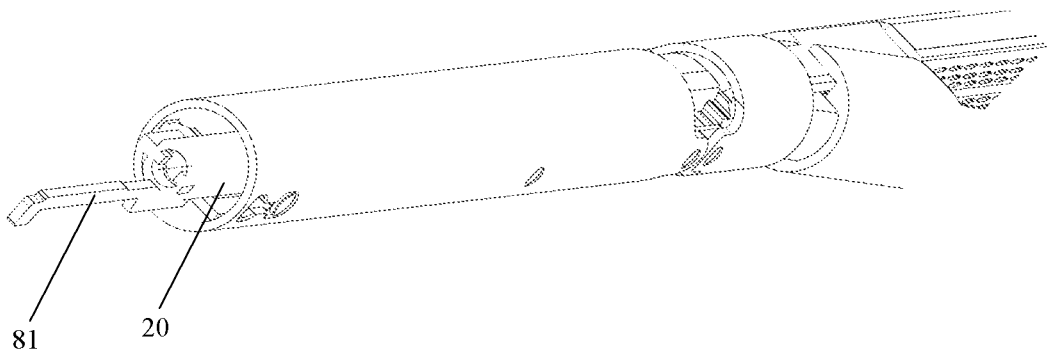
FIG. 15A to FIG. 15B are schematic diagrams of a front articulation driver member of a surgical stapler provided by an embodiment of the present disclosure.
Figure 15B:
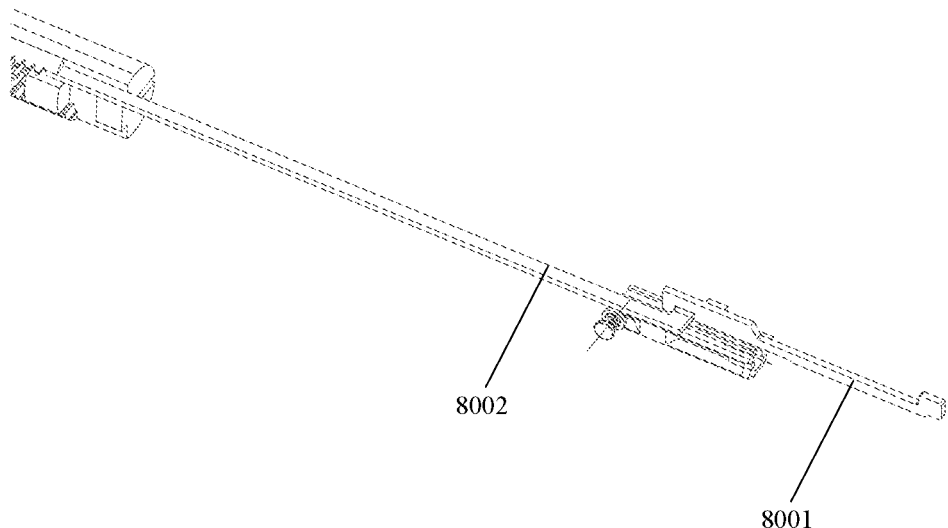

FIG. 15A to FIG. 15B are schematic diagrams of the front articulation driver member of the surgical stapler 100 provided by an embodiment of the present disclosure. In conjunction with FIG. 5C and FIG. 15A to FIG. 15B, the front articulation driver assembly includes a front articulation driver member 81, the front articulation driver member 81 is connected with the end effector 1; the rear articulation driver assembly includes a rear articulation driver member 82, the rear articulation driver member 82 and the first driver mechanism 10 have a same extension direction and are arranged side by side, the detachable portion 3 is in detachable connection with the main body portion 4 to enable the front articulation driver member 81 to be in detachable connection with the rear articulation driver member 82, for example, the two are in hook connection or plug connection, etc. The extension direction of the rear articulation driver member 82 and the first driver mechanism 10 is the axial direction; in a process during which the articulation mechanism drives the end effector 1 to pivot, the front articulation driver member 81 and the rear articulation driver member 82 move toward the end effector 1 along the axial direction to drive the end effector 1 to pivot in a first pivoting direction; for example, the front articulation driver member 81 and the rear articulation driver member 82 may further move along the axial direction away from the end effector 1 to drive the end effector 1 to pivot in a second pivoting direction opposite to the first pivoting direction.

For example, as shown in FIG. 15B, the front articulation driver member 81 includes a first portion 8001 and a second portion 8002 that are connected with each other, for ease of fabrication of the two; when a length of the front articulation driver member 81 along the axial direction is too long, the front articulation driver member 81 is divided into two portions connected with each other, which is favorable for buffering stress of the front articulation driver member 81, and also facilitates fabrication and mounting of the front articulation driver member 81.

For example, in conjunction with FIG. 2, FIG. 5A and FIG. 14A to FIG. 14B, the front articulation driver assembly includes a bendable portion 80, the bendable portion 80 is configured to bend toward the first pivoting direction or the second pivoting direction so that the end effector 1 pivots around the bendable portion 80; the end effector 1 includes a first end close to the front articulation driver assembly and a second end opposite to the first end of the end effector 1, the first end of the end effector 1 is connected with the front articulation driver assembly, and the bendable portion 80 is located in the axial direction between, the position where the front articulation driver assembly is connected with the first end of the end effector 1, and, the position where the front articulation driver assembly is connected with the rear articulation driver assembly, so that the end effector 1 may pivot around the bendable portion 80. In conjunction with FIG. 11A and FIG. 14B, the second driver mechanism 20 includes a transmission belt 201 extending along the axial direction; in the surgical fastener pushing stage, the transmission belt 201 enters the end effector 1 via the bendable portion 80 to drive the surgical fastener pushing assembly to push the surgical fastener out of the fastener-cartridge assembly 11, and a belt surface of the transmission belt 201 is substantially perpendicular to the pivoting direction of the end effector 1, so as to increase flexibility of the second driver mechanism 20; because in the surgical fastener pushing stage and the cutting stage, the transmission belt 201 passes through the bendable portion 80, this technical scheme is favorable for reducing the resistance force of the pivoting of the end effector 1 at the position where the bendable portion 80 is located, and can avoid injuries to the second driver mechanism 20.

Referring to FIG. 5B, for example, the second driver mechanism 20 further includes a connection portion 202, the connection portion 202 is in detachable connection with the closing mechanism 2 and is located on a side of the transmission belt 201 away from the end effector 1, an end of the connection portion 202 close to the end effector 1 is connected with an end of the transmission belt 201 away from the end effector 1, and the detachable portion 3 is connected with the main body portion 4 so that the end of the connection portion 202 away from the end effector 1 is connected with the first driver mechanism 10, which, thus, can not only utilize the transmission belt 201 to reduce breakage of the second driver mechanism 20 when the end effector 1 pivots, but also can utilize the connection portion 202 to implement various functions. For example, a part of the connection portion 202 also serves as the above-described lock driver structure, for example, the connection portion 202 is also in detachable connection with the separable connection structure 6. Therefore, the same member is fully utilized to implement the above-described various functions, which saves space and has great significance for reducing the size of the surgical stapler 100.

For example, the second driver mechanism 20 includes a plurality of transmission belts 201, the plurality of transmission belts 201 are stacked in a direction perpendicular to the belt surface, and there is no gap between adjacent transmission belts 201, so as to enhance strength of the second driver mechanism 20 and ensure the reliability of driving the surgical fastener pushing driver mechanism 40 to move along the axial direction by the second driver mechanism 20.

For example, the transmission belt 201 is made of steel, a thickness of each transmission belt 201 in the direction perpendicular to the belt surface ranges from 100 μm to 1,000 μm, and a length of each transmission belt 201 in the axial direction ranges from 10 cm to 30 cm, so as to ensure the strength of the transmission belts required for driving the surgical fastener pushing driver mechanism 40 to move along the axial direction. Of course, the size may be designed according to actual needs, which is not limited by the embodiments of the present disclosure. The material of the transmission belt 201 is also not limited to steel, or may also be other metal materials or organic materials.

For example, referring to FIG. 5B, in a state where the second driver mechanism 20 is connected with the first driver mechanism 10, an end of the transmission belt 201 away from the first driver mechanism 10 is connected with the surgical fastener pushing driver mechanism 40, for example, welded with the surgical fastener pushing driver mechanism 40, of course, other connection modes are also possible.

The direction from the first end of the end effector 1 to the second end of the end effector 1 is a first direction. As shown in FIG. 11B and FIG. 13C, the fastener-cartridge bracket of the fastener-cartridge includes the first portion 511 and the second portion 512 extending along the first direction, and both the first portion 511 of the fastener-cartridge bracket and the second portion 512 of the fastener-cartridge bracket include a surgical fastener slot 110 for accommodating the surgical fastener and limit a chute extending along the first direction; in a process during which the surgical fastener pushing driver mechanism 40 drives the surgical fastener pushing slide block 60 to move, the cutting driver mechanism 40*a* and the transmission belt enter the chute 42 via the bendable portion 80 and slide in the chute 42, so as to drive the cutting driver mechanism 40*a* (i.e., the surgical fastener pushing driver mechanism 40) to move between the first end of the end effector 1 and the second end of the end effector 1.

For example, as shown in FIG. 14A to FIG. 14B and FIG. 15A, the front articulation driver assembly includes a transmission mechanism, the transmission mechanism is connected with the front articulation driver member 81 and is configured to drive, as driven by the front articulation driver member 81, the end effector 1 to pivot around the bendable portion 80. For example, the transmission mechanism includes a driver rack 820 and gears 811/812/813. The driver rack 820 includes driver teeth 821, and extends along the axial direction and is connected with the front articulation driver member 81 to move along the axial direction as driven by the front articulation driver member 81; for example, the driver rack 820 and the front articulation driver member 81 are formed integrally. The driver rack 820 includes driver teeth 821, and extends along the axial direction and is connected with the front articulation driver member 81 to move along the axial direction as driven by the front articulation driver member 81. The gears 811/812/813 are meshed with the driver teeth 821, and the driver rack 820 moves along the axial direction to drive the gears to rotate. The front articulation driver assembly further includes an articulation connection portion; a first end of the articulation connection portion close to the end effector 1 is connected with the first end of the end effector 1; a second end of the articulation connection portion away from the end effector 1 includes a terminal tooth 814; the terminal tooth 814 are meshed with the gears 811/812/813 to make the articulation connection portion and the end effector 1 pivot as driven by the gears 811/812/813; a position where the terminal tooth 814 are meshed with the gears 811/812/813 is at the bendable portion 80; the plate surfaces of the gear plates of the gears 811/812/813 are substantially perpendicular to the belt surface of the transmission belt 201, so that the belt surface of the transmission belt 201 is substantially perpendicular to the direction in which the end effector 1 pivots.

For example, as shown in FIG. 14A to FIG. 14B, the transmission mechanism includes a plurality of gears arranged in the axial direction, adjacent gears among the plurality of gears 3 are meshed with each other; a gear among the plurality of gears 811/812/813 that is closest to the end effector 1 is meshed with the terminal tooth 814 at the second end of the articulation connection portion, and at least the gear 811 among the plurality of gears 811/812/813 that is farthest away from the end effector 1 is meshed with the driver teeth 821 of the driver rack 820, so as to avoid dependence of a single gear and increase stability of the transmission mechanism.

For example, as shown in FIG. 14A to FIG. 14B, a diameter of the gear plate of the gear 813 among the plurality of gears 811/812/813 that is closest to the end effector 1 is less than a diameter of the gear plate of the other gears 812/813 among the plurality of gears 811/812/813, so that the front articulation driver member connected with a gear with a larger diameter only needs to move a tiny distance along the axial direction, so that the terminal tooth 814 of the articulation connection portion may rotate by a great angle, that is, the end effector 1 connected with the articulation connection portion rotates by a great angle, so as to facilitate implementing a greater pivoting range of the end effector 1 with a limited axial length of the front articulation driver member.

For example, as shown in FIG. 14A to FIG. 14B, the surgical stapler 100 further includes a stabilization rack 830; the stabilization rack 830 is meshed with the gears 811/812/813; the driver rack 820 is located on a first side of the gears 811/812/813; the stabilization rack 830 is located on a second side of the gears 811/812/813 that is opposite to the first side of the gears 811/812/813; and the stabilization rack 830 is not connected with the front articulation driver member 81. The stabilization rack 830 can bear the gears 811/812/813, so that structures and operation of the gears 811/812/813 are more stable.

For example, as shown in FIG. 5A, FIG. 14A to FIG. 14B, in the case where the closing mechanism is the sleeve 2 sleeved on the outer side of the second driver mechanism 20 and the transmission mechanism, the fastener-cartridge assembly 11 includes a first end close to the sleeve 2, and the anvil 12 includes a first end close to the sleeve 2. In the closing stage, the second driver mechanism 20 moves, as driven by the first driver mechanism 10, toward the end effector 1 so as to drive the sleeve 2 to move toward the end effector 1, so that the sleeve 2 is sleeved on the first end of the fastener-cartridge assembly 11 and the first end of the anvil 12 to apply pressure to the first end of the fastener-cartridge assembly 11 and the first end of the anvil 12, so as to close the end effector 1; the sleeve 2 includes a first portion 21 close to the end effector 1 and a second portion 22 away from the end effector 1; the surgical stapler 100 further includes a rotatable sleeve connection part 25; the first portion 21 of the sleeve 2 is connected with the second portion 22 of the sleeve 2 through the rotatable sleeve connection part 25; the rotatable sleeve connection part 25 is located in the bendable portion 80 so that the first portion 21 of the sleeve 2 can pivot as the end effector 1 pivots, and thus the closing mechanism can be adapted to the design of pivoting of the end effector 1.

For example, as shown in FIG. 14A to FIG. 14B, rotatable sleeve connection part 25 includes a first hinge structure and a second hinge structure connected with each other; the first hinge structure is connected with the first portion of the sleeve 2, and the second hinge structure is connected with the second portion of the sleeve 2.

Figure 16A:
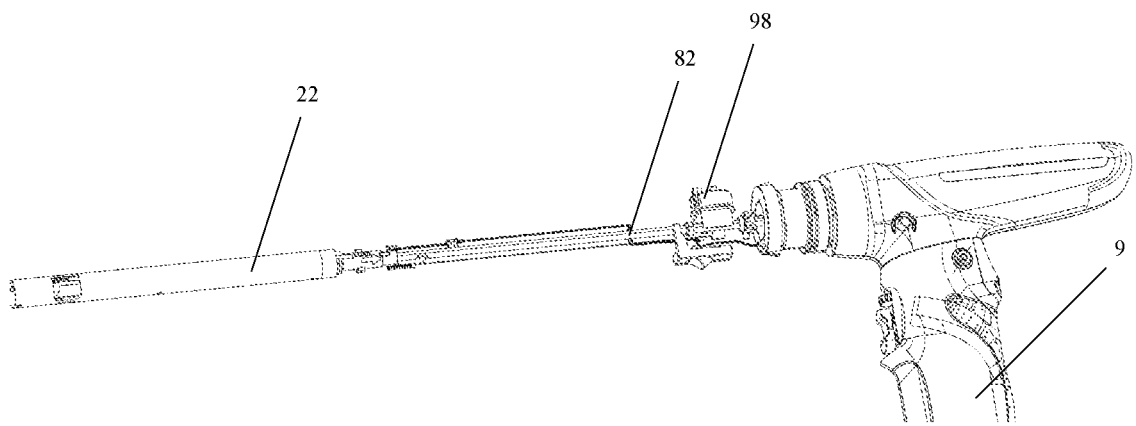
FIG. 16A is a partial schematic diagram of a rear articulation driver assembly of a surgical stapler provided by an embodiment of the present disclosure.
Figure 16B:
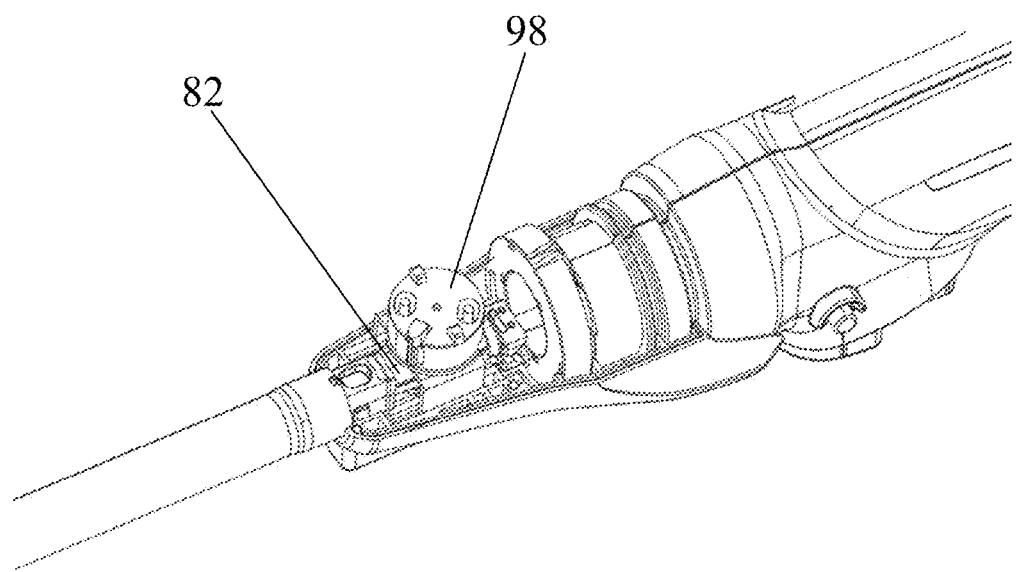
FIG. 16B is a partial schematic diagram of a manual adjustment driver mechanism of a surgical stapler provided by an embodiment of the present disclosure.

FIG. 16A is a partial schematic diagram of the rear articulation driver assembly of the surgical stapler 100 provided by an embodiment of the present disclosure; FIG. 16B is a partial schematic diagram of a manual adjustment driver mechanism of the surgical stapler 100 provided by an embodiment of the present disclosure; in conjunction with FIG. 9 and FIG. 16A to FIG. 16B, the rear articulation driver assembly further includes a third articulation driver mechanism; the third articulation driver mechanism is configured to drive, in a process during which the articulation mechanism drives the end effector 1 to pivot, the front articulation driver member 81 and the rear articulation driver member 82 to move along the axial direction toward or away from the end effector 1; and the third articulation driver mechanism is configured to be able to adjust a distance by which the front articulation driver member 81 and the rear articulation driver member 82 moves along the axial direction toward the end effector 1 or away from the end effector 1, so as to adjust a pivoting range of the end effector 1.

Figure 18A:
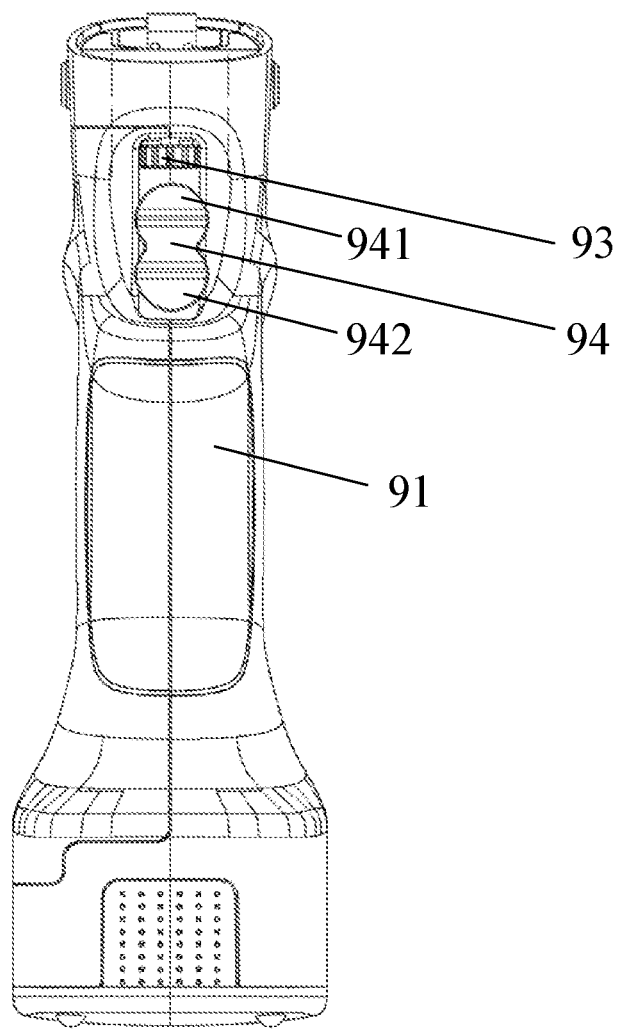
FIG. 18A to FIG. 18B are schematic diagrams of a handle provided by an embodiment of the present disclosure.
Figure 18B:
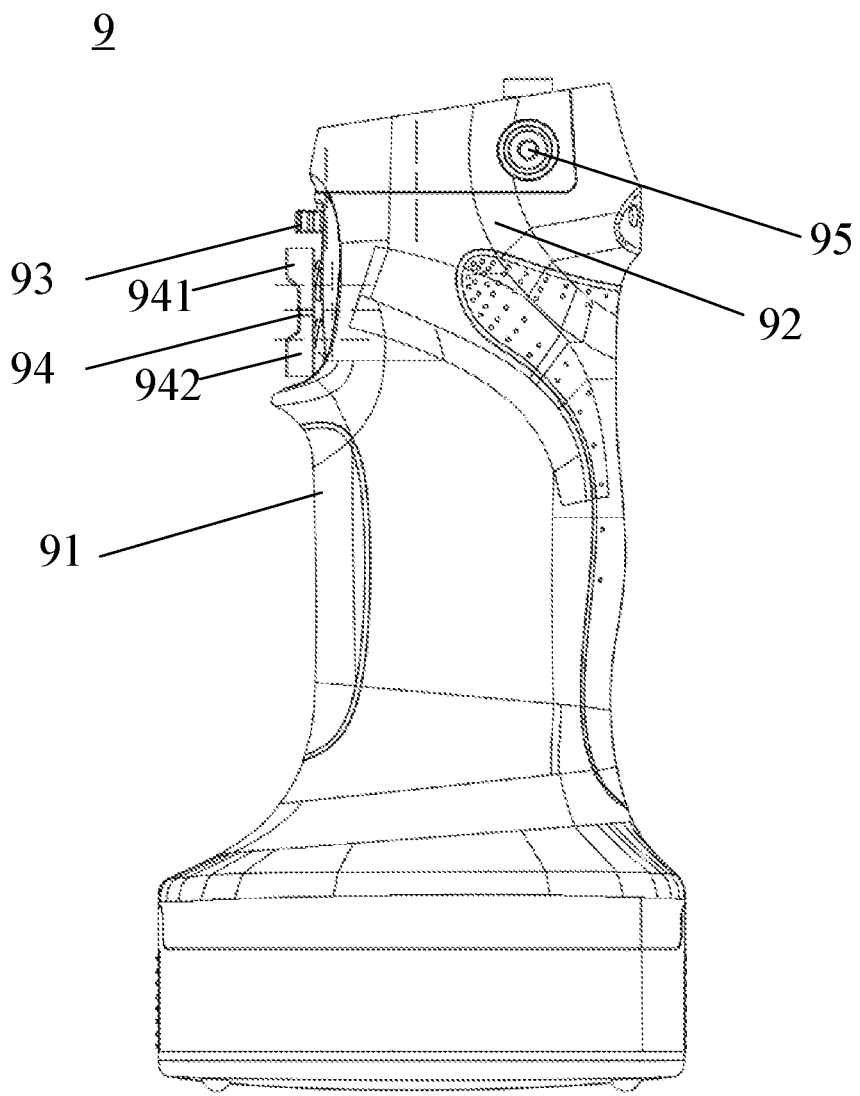

FIG. 18A to FIG. 18B are schematic diagrams of a handle provided by an embodiment of the present disclosure; as shown in FIG. 16A to FIG. 16B and FIG. 18A to FIG. 18B, the third articulation driver mechanism includes a grade adjustment switch 98, and the grade adjustment switch 98 is configured to adjust, grade by grade, the distance by which the front articulation driver member 81 and the rear articulation driver member 82 moves along the axial direction toward the end effector 1, or adjust, grade by grade, the distance by which the front articulation driver member 81 and the rear articulation driver member 82 moves along the axial direction away from the end effector 1, so as to adjust, grade by grade, the pivoting range of the end effector 1.

For example, the front articulation driver member 81 and the rear articulation driver member 82 are both single rods extending along the axial direction; the front articulation driver member 81 extends along the axial direction and is arranged side by side with the second driver mechanism 20 to fully utilize the space inside the long and narrow sleeve 2; and the rear articulation driver member 82 extends along the axial direction and is arranged side by side with the first driver mechanism 10, to fully utilize space inside the long and narrow sleeve 2.

As shown in FIG. 15A to FIG. 15B, the detachable portion 3 is in detachable connection with the main body portion 4 so that the front articulation driver member 81 and the rear articulation driver member 82 are in detachable connection with each other, so as to realize detachable connection between the front articulation driver assembly and the rear articulation driver assembly.

For example, the front articulation driver member 81 includes a first portion 8001 in FIG. 15A to FIG. 15B and a second portion 8002 in detachable connection with the first portion 8001; and when the detachable portion 3 of the surgical stapler 100 is not connected with the main body portion 4, both the first portion 8001 and the second portion 8002 of the front articulation driver member 81 are located in the detachable portion 3.

As shown in FIG. 16A to FIG. 16B, the third articulation driver mechanism is a manual adjustment driver mechanism; by manually adjusting the grade level, each time one grade range is toggled toward a first toggle direction, the front articulation driver member 81 and the rear articulation driver member 82 move along the axial direction toward the end effector 1 by one grade of distance so that the end effector 1 rotates toward the first pivoting direction by one grade of angle; and each time one grade range is toggled toward a second toggle direction, the front articulation driver member 81 and the rear articulation driver member 82 move along the axial direction away from the end effector 1 by one grade of distance so that the end effector 1 rotates toward the second pivoting direction by one grade of angle. For example, as shown in FIG. 1, the manual adjustment driver mechanism includes a manual knob 96 that is manually operated to control the grade range in which the front articulation driver member 81 and the rear articulation driver member 82 move along the axial direction toward the end effector 1.

Alternatively, the third articulation driver mechanism is an electric driver mechanism. For example, the electric driver mechanism includes an electric motor and an articulation control switch; the electric motor is configured to rotate to drive the front articulation driver member 81 and the rear articulation driver member 82 to move along the axial direction toward the end effector 1 or move along the axial direction away from the end effector 1; and the articulation control switch is configured to control sending an electrical signal to the electric motor to control operation of the electric motor.

As shown in FIG. 16A to FIG. 16B and FIG. 18A to FIG. 18B, the main body portion 4 includes a handle 9; the articulation control switch is a dial switch; the dial switch includes a dial 93 arranged on a surface of the handle 9; the dial 93 is configured to be toggled toward the first toggle direction to drive the end effector 1 to pivot toward the first pivoting direction, and is configured to be toggled toward the second toggle direction to drive the end effector 1 to pivot toward the second pivoting direction; and the first toggle direction is different from the second toggle direction.

For example, the dial 93 has grade marks thereon. For each grade range toggled toward the first toggle direction, the front articulation driver member 81 and the rear articulation driver member 82 move along the axial direction toward the end effector 1 by one grade of distance such that the end effector 1 rotates toward the first pivoting direction by one grade of angle; or/and, for each grade range toggled toward the second toggle direction, the front articulation driver member 81 and the rear articulation driver member 82 move along the axial direction away from the end effector 1 by one grade of distance such that the end effector 1 rotates toward the second pivoting direction by one grade of angle.

Figure 17:
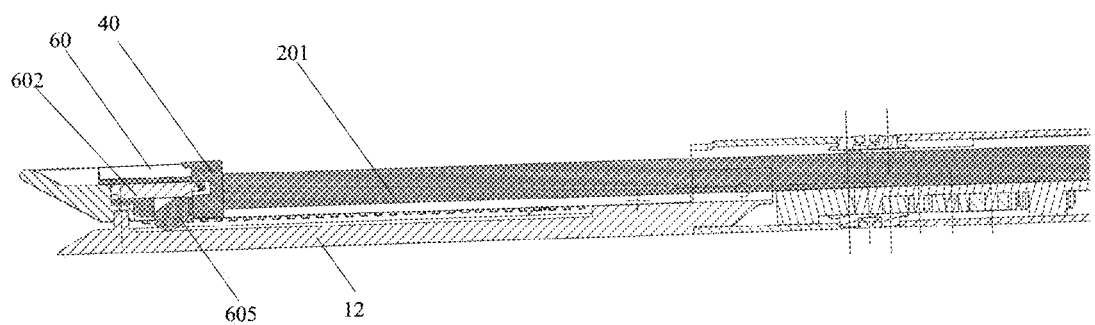
FIG. 17 is a schematic diagram of the case that the surgical fastener pushing slide block is located at the second end of the end effector before the surgical fastener pushing stage provided by an embodiment of the present disclosure.

Exemplarily, FIG. 17 is a schematic diagram of the surgical fastener pushing slide block 60 being located at the second end of the end effector 1 before the surgical fastener pushing stage provided by an embodiment of the present disclosure; as shown in FIG. 17, the surgical stapler 100 includes an end effector 1, a closing mechanism and a surgical fastener pushing assembly. The end effector 1 includes a fastener-cartridge assembly 11 and an anvil 12, at least one surgical fastener is provided in fastener-cartridge assembly 11; the closing mechanism is configured to drive, in the closing stage, the fastener-cartridge assembly 11 and the anvil 12 to engage with each other so that the target tissue is clamped between the fastener-cartridge assembly 11 and the anvil 12, the end effector 1 has a first end close to the closing mechanism and a second end away from the closing mechanism; the surgical fastener pushing assembly is configured to push, sequentially from the second end to the first end, the surgical fastener out of the fastener-cartridge assembly 11 into the target tissue in the surgical fastener pushing stage following the closing stage, so as to suture the target tissue along the direction from the second end of the end effector 1 to the first end of the end effector 1. As compared with the process of suturing the target tissue along the direction from the first end of the end effector 1 to the second end of the end effector 1, the process of suturing the target tissue from the second end of the end effector 1 to the first end of the end effector 1 can reduce tissue slippage, suture the target tissue with higher precision, and avoid deformation of the transmission belt 201 due to an excessively great resistance force when the transmission belt 201 moves in a direction from the first end of the end effector 1 to the second end of the end effector 1 while suturing the target tissue from the first end of the end effector 1 to the second end of the end effector 1, thus failing to achieve a preset surgical fastener push distance as driven by the transmission belt 201.

The surgical fastener pushing assembly includes surgical fastener pushing piece 700, a surgical fastener pushing slide block 60 and a surgical fastener pushing driver mechanism 40. The surgical fastener pushing piece 700 are arranged in a direction from the second end to the first end, and are configured to apply a surgical fastener pushing pressure to the surgical fastener to push the surgical fastener out of the fastener-cartridge assembly 11; the surgical fastener pushing slide block 60 is configured to apply a pressure to the surgical fastener pushing piece 700 to drive the surgical fastener pushing piece 700 to apply the surgical fastener pushing pressure to the staple; the surgical fastener pushing driver mechanism 40 is configured to drive, in the surgical fastener pushing stage, the surgical fastener pushing slide block 60 to move along the direction from the second end of the end effector 1 to the first end of the end effector 1, so that the surgical fastener pushing slide block 60 is sequentially in contact with the surgical fastener pushing pieces 700 along the direction from the second end of the end effector 1 to the first end of the end effector 1 to apply the surgical fastener pushing pressure to the surgical fastener pushing pieces 700.

For example, as shown in FIG. 17, before the surgical fastener pushing stage, the surgical fastener pushing slide block 60 is located at the second end of the end effector 1; in the surgical fastener pushing stage, the surgical fastener pushing slide block 60 moves from the second end of the end effector 1 to the first end of the end effector 1 and sequentially pushes the surgical fasteners in the fastener-cartridge assembly 11 in the direction from the second end to the first end to suture the target tissue.

For example, as shown in FIG. 17, the surgical stapler 100 further includes a cutting device 60*a* and a cutting driver mechanism 40*a*. The cutting device 60*a* is configured to cut the target tissue in the cutting stage after the entire target tissue is sutured; the cutting driver mechanism 40*a* is configured to drive, in the cutting stage, the cutting device 60*a* to cut the target tissue; and in the cutting stage, the cutting device 60*a* moves from the first end of the end effector 1 to the second end of the end effector 1 to cut the target tissue along the direction from the first end of the end effector 1 to the second end of the end effector 1.

For example, the cutting device 60*a* includes a blade-carrying member 60*b* and a cutting blade 605. The surgical fastener pushing slide block 60 serves as the blade-carrying member 60*b*, that is, in the closing stage and the surgical fastener pushing stage, the cutting device 60*a* is located at the second end of the end effector 1. The surgical fastener pushing driver mechanism 40 serves as the cutting driver mechanism 40*a*; the cutting blade 605 is in movable connection with the surgical fastener pushing slide block 60, and the surgical fastener pushing slide block 60 moves to drive the cutting blade 605 to move; in the surgical fastener pushing stage, the cutting blade 605 is at least partially located in the surgical fastener pushing slide block 60, the cutting blade 605 moves with the surgical fastener pushing slide block 60 along the direction from the second end of the end effector 1 to the first end of the end effector 1, and the cutting blade 605 has a preset distance to the target tissue clamped between the fastener-cartridge assembly 11 and the anvil 12 so that the cutting blade 605 is not in contact with the target tissue. The surgical fastener pushing slide block 60 is located at the first end of the end effector 1 at the end of the surgical fastener pushing stage in the surgical stapler 100. When the surgical fastener pushing stage ends, the surgical fastener pushing slide block 60 reaches the first end of the end effector 1; in the cutting stage, the surgical fastener pushing driver mechanism 40 pushes the surgical fastener pushing slide block 60 so that the cutting blade 605 moves with the surgical fastener pushing slide block 60 along the direction from the first end of the end effector 1 to the second end of the end effector 1; and the cutting blade 605, under the action of the blade ejection driving force, is in contact with the target tissue and cuts the target tissue along the direction from the first end of the end effector 1 to the second end of the end effector 1. Cutting the target tissue after the entire target tissue is sutured is favorable for improving the accuracy of suturing and cutting the target tissue, and multiplexing the surgical fastener pushing slide block 60 as the blade-carrying member 60*b* can simplify the structure of the surgical stapler 100 and save space. For example, the surgical stapler 100 includes a blade ejection driver mechanism 602; the fastener-cartridge bracket includes a resistance face 503; the resistance face 503 faces the blade ejection driver mechanism 602; the blade ejection driver mechanism 602 is configured to hit the resistance face 503 when the cutting device 60*a* reaches the first end of the end effector 1 as driven by the cutting driver mechanism 40*a*, so that the resistance face 503 applies a blade ejection driving force to the blade ejection driver mechanism 602; and the blade ejection driver mechanism 602 is configured to be in contact with the cutting blade 605 under the action of the blade ejection driving force, so as to apply a first driving force to drive the cutting blade 605 to move toward the target tissue. Then, the surgical fastener pushing driver mechanism 40 pushes the surgical fastener pushing slide block 60 to make the cutting blade 605 move with the surgical fastener pushing slide block 60 along the direction from the first end to the second end; and the cutting blade 605 is in contact with the target tissue under the action of the blade ejection driving force, and cuts the target tissue along the direction from the first end to the second end, which, thus, can simplify the structure of the surgical stapler, reduce reciprocating movement of the cutting blade 605 between the first end of the end effector 1 and the second end of the end effector 1, and improve operation efficiency of the surgical stapler 100.

Of course, in other embodiments, the process of surgical fastener pushing and the process of cutting may be independent of each other, that is, the surgical fastener pushing slide block 60 does not serve as the blade-carrying member 60*b*. That is, the cutting device 60*a* includes the blade-carrying member 60*b* and the cutting blade 605; the cutting blade 605 is in movable connection with the blade-carrying member 60*b*; the blade-carrying member 60*b* moves to drive the cutting blade 605 to move; in the surgical fastener pushing stage, the cutting device 60*a* and the cutting driver mechanism 40*a* are located at the first end of the end effector 1; in the cutting stage, the cutting driver mechanism 40*a* drives the cutting device 60*a* to move from the first end of the end effector 1 to the second end of the end effector 1 to cut the target tissue along the direction from the first end to the second end; the blade-carrying member 60*b* and the surgical fastener pushing slide block 60 are independent of each other; and the cutting driver mechanism 40*a* and the surgical fastener pushing driver mechanism 40 are independent of each other.

In one example, as shown in FIG. 17, for example, the surgical fastener pushing driver mechanism 40 is configured to be disconnected with the surgical fastener pushing slide block 60 in the closing stage, and is configured to move, before the surgical fastener pushing stage, toward the second end of the end effector 1 to be connected with the surgical fastener pushing slide block 60, and is configured to move, in the surgical fastener pushing stage, along the direction from the second end of the end effector 1 to the first end of the end effector 1 to drive the surgical fastener pushing slide block 60 to move along the direction from the second end of the end effector 1 to the first end of the end effector 1.

In another example, for example, the surgical fastener pushing driver mechanism 40 is configured to be located at the second end of the end effector 1 and connected with the surgical fastener pushing slide block 60 in the closing stage, and is configured to move, in the surgical fastener pushing stage, along the direction from the second end of the end effector 1 to the first end of the end effector 1 to drive the surgical fastener pushing slide block to move along the direction from the second end of the end effector to the first end of the end effector.

For example, in another embodiment, in the cutting stage, the cutting device moves from the second end of the end effector to the first end of the end effector to cut the target tissue along the direction from the second end to the first end. For example, the surgical fastener pushing slide block serves as the blade-carrying member.

Alternatively, in some embodiments, in the surgical fastener pushing stage, the cutting device and the cutting driver mechanism are located at the second end of the end effector; the cutting device cuts the target tissue after the entire target tissue is sutured; and in the cutting stage, the cutting driver mechanism drives the cutting device to move from the second end of the end effector to the first end of the end effector to cut the target tissue along the direction from the second end of the end effector to the first end of the end effector; the blade-carrying member and the surgical fastener pushing slide block are independent of each other; and the cutting driver mechanism and the surgical fastener pushing driver mechanism are independent of each other. After the surgical fastener pushing driver mechanism moves from the second end of the end effector to the first end of the end effector to suture the target tissue, the surgical fastener pushing driver mechanism then drives the surgical fastener pushing slide block to move from the first end of the end effector to the second end of the end effector, to enable the surgical fastener pushing slide block to be connected with the cutting device, then, the surgical fastener pushing driver mechanism drives the cutting device to move from the second end of the end effector to the first end of the end effector; the cutting blade in the cutting device is in contact with the target tissue, so as to move along the direction from the second end of the end effector to the first end of the end effector, to cut the target tissue, that is, in this embodiment, the cutting blade in the cutting device is always in contact with the target tissue; when moving along the direction from the second end of the end effector to the first end of the end effector, the cutting blade may cut the target tissue. For example, an end of the blade-carrying member close to the surgical fastener pushing slide block has a third connection structure; an end of the surgical fastener pushing slide block close to the blade-carrying member has a fourth connection structure; and the third connection structure is connected with the fourth connection structure, so that the surgical fastener pushing slide block is connected with the cutting device. The above-described first connection structure, for example, including the via hole, may be referred to for the third connection structure; the above-described second connection structure, for example, including the elastic connection piece, may be referred to for the third connection structure; and the foregoing connection mode between the first connection structure and the second connection structure may be referred to for specific contents.

For example, in other embodiments, the cutting device includes a blade-carrying member and a cutting blade; the surgical fastener pushing slide block serves as the blade-carrying member; the surgical fastener pushing driver mechanism serves as the cutting driver mechanism; the cutting blade is in movable connection with the surgical fastener pushing slide block, and the surgical fastener pushing slide block moves to drive the cutting blade to move. The surgical fastener pushing stage and the cutting stage are performed simultaneously; the surgical fastener pushing slide block moves along the direction from the second end of the end effector to the first end of the end effector to sequentially push the surgical fastener out to suture target tissue; the cutting blade is in contact with the target tissue and the cutting blade moves with the surgical fastener pushing slide block in order to cut the target tissue along the direction from the second end of the end effector to the first end of the end effector; and the cutting blade and the surgical fastener pushing slide block are configured such that the unit portions of the target tissue is sequentially sutured by the surgical fastener along the direction from the second end of the end effector to the first end of the end effector, and each unit portion of the target tissue is cut by the cutting blade immediately after being sutured, that is, the process of cutting the target tissue is performed while the process of suturing the target tissue is performed; and with respect to each unit portion to be sutured and cut of the target tissue, the process of cutting lags a bit behind the process of suturing.

For example, in the above-mentioned case of cutting immediately while suturing, for example, in the process during which the cutting blade 605 moves with the surgical fastener pushing slide block 60 along the direction from the second end of the end effector 1 to the first end of the end effector 1, an end portion of the surgical fastener pushing slide block 60 close to the first end of the end effector 1 firstly drives the surgical fastener pushing piece 700 to push out the staple; and the cutting blade 605 is located on a side of the end of the end portion of the surgical fastener pushing slide block 60 close to the second end of the end effector 1 and is spaced apart from the end portion of the surgical fastener pushing slide block 60 by a preset distance. For example, the preset distance is a sum of widths, along the direction from the second end of the end effector 1 to the first end of the end effector 1, of 2~4 surgical fasteners continuously arranged along the direction from the second end of the end effector 1 to the first end of the end effector 1, in this way, with respect to each unit portion to be sutured and cut of the target tissue, the degree that the cutting lags behind the suturing is more suitable, which can ensure a better effect of the suturing and the cutting.

For example, with respect to the above-described various embodiments in which suturing the target tissue is performed along the direction from the second end of the end effector 1 to the first end of the end effector 1, the surgical stapler 100 further includes a first driver mechanism 10; the first driver mechanism 10 is configured that, in the closing stage, the first driver mechanism 10 is in detachable connection with the closing mechanism to drive the closing mechanism to close the end effector 1; and the first driver mechanism 10 is configured that, in the surgical fastener pushing stage, the first driver mechanism 10 is separated from the closing mechanism and drives the surgical fastener pushing assembly to push the surgical fasteners out of the fastener-cartridge assembly 11. The surgical stapler 100 further includes a second driver mechanism 20; the second driver mechanism 20 is in detachable connection with the first driver mechanism 10; the second driver mechanism 20 is configured to be in detachable connection with the closing mechanism in the closing stage and is configured to move, as driven by the first driver mechanism 10, toward the second end of the end effector 1 so that the closing mechanism is in contact with the fastener-cartridge assembly 11 and the anvil 12 and applies pressure to the fastener-cartridge assembly 11 and the anvil 12 so as to close the end effector 1; the second driver mechanism 20 is further configured to be separated from the closing mechanism after the end effector 1 is closed, continue to move, as driven by the first driver mechanism 10, toward the second end of the end effector 1 to be connected with the surgical fastener pushing driver mechanism 40, and continue to move toward the second end of the end effector 1 to drive the surgical fastener pushing driver mechanism 40 to reach the second end of the end effector 1 and to be connected with the surgical fastener pushing slide block 60; and the second driver mechanism 20 is further configured to drive, in the surgical fastener pushing stage, as driven by the first driver mechanism 10, to move along the direction from the second end of the end effector 1 to the first end of the end effector 1 to suture the target tissue. The descriptions in the foregoing embodiments may be referred to for specific structures such as the first driver mechanism 10 and the second driver mechanism 20, and no details are repeated here.

For example, with respect to the above-described various embodiments in which suturing the target tissue is performed along the direction from the second end of the end effector 1 to the first end of the end effector 1, the cutting driver mechanism 40a is configured to drive, as driven by the first driver mechanism 10, the cutting device to cut the target tissue.

For example, with respect to the above-described various embodiments in which suturing the target tissue is performed along the direction from the second end of the end effector 1 to the first end of the end effector 1, the closing mechanism is the sleeve 2 sleeved on the outer side of the second driver mechanism 20, the fastener-cartridge assembly 11 includes a first end close to the sleeve 2, the anvil 12 includes a first end close to the sleeve 2; in the closing stage, the second driver mechanism 20 moves, as driven by the first driver mechanism 10, toward the end effector 1 to drive the sleeve 2 to move toward the end effector 1 so that the sleeve 2 is sleeved on the first end of the fastener-cartridge assembly 11 and the first end of the anvil 12, so as to apply pressure to the first end of the fastener-cartridge assembly 11 and the first end of the anvil 12 to close the end effector 1. The foregoing description about the sleeve 2 making the end effector 1 close may be referred to for the specific structure. The features of the respective embodiments of the present disclosure may be combined without conflict.

At least one embodiment of the present disclosure provides a handle 9; the handle 9 may be used in a surgical stapler 100; and the surgical stapler 100 may be used as a medical apparatus, for example, as a surgical apparatus, for holding target tissue, and suturing and cutting the target tissue. The handle 9 is configured to be in detachable connection with the detachable portion 3 of the surgical stapler 100; the detachable portion 3 includes the end effector 1; and the end effector 1 includes the fastener-cartridge assembly 11 and the anvil 12.

Figure 19:
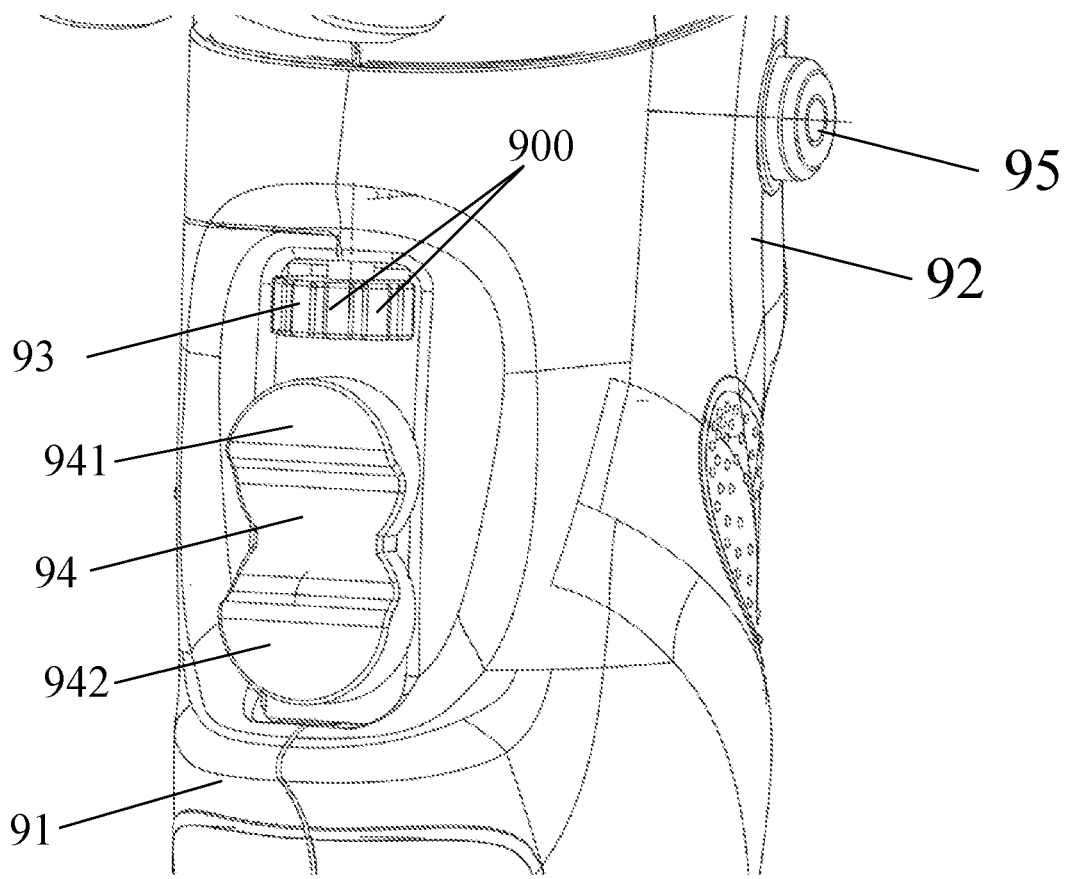
FIG. 19 is an enlarged schematic diagram of a dial and a two-direction control button.

Exemplarily, FIG. 18A to FIG. 18B are schematic diagrams of a handle provided by an embodiment of the present disclosure; and FIG. 19 is an enlarged schematic diagram of a dial and a two-way control button. As shown in FIG. 18A to FIG. 18B and FIG. 19, the handle 9 includes a dial switch; the dial switch includes a dial 93 provided on a first surface 91 of the handle 9; and the dial 93 is configured to be toggled to rotate to control the pivoting direction and the pivoting angle of the end effector 1, so that controlling the pivoting direction and the pivoting angle of the end effector 1 by operating the dial 93 is realized, which is convenient to operate and control in a surgical procedure.

For example, the dial 93 is configured to be toggled toward a first rotation direction to rotate toward the first rotation direction, so as to drive the end effector 1 to pivot toward the first pivoting direction, and is configured to be toggled toward a second rotation direction to rotate toward the second rotation direction, so as to drive the end effector 1 to pivot toward the second pivoting direction, and the first rotation direction is opposite to the second rotation direction, so as to control the end effector 1 to pivot toward different directions by operating the dial 93, which is convenient to operate and control in a surgical procedure.

For example, grade marks are provided on the dial 93; according to the grade mark, each time a user operates the dial 93 to rotate toward the first rotation direction by one grade, the end effector 1 rotates toward the first pivoting direction by an angle corresponding to one grade; and according to the grade mark, each time the user operates the dial 93 to rotate one grade toward the second rotation direction, the end effector 1 rotates toward the second pivoting direction by an angle corresponding to one grade, to adjust the pivoting range of the end effector 1 toward different directions by operating the dial 93, which is convenient to operate and easy to control in a surgical procedure.

For example, as shown in FIG. 18A to FIG. 18B and FIG. 19, the grade marks includes a plurality of grades slots 900 arranged along the first rotation direction and the second rotation direction; and the plurality of grade slots 900 are configured that, each time the dial 93 rotates by one grade slot 900 toward the first rotation direction, the end effector 1 rotates toward the first pivoting direction by an angle corresponding to one grade; each time the dial 93 rotates by one grade slot 900 toward the second rotation direction, the end effector 1 rotates toward the second pivoting direction by an angle corresponding to one grade. In this way, the operator may adjust the number of grade slots 900 for rotation through tactile sensation, so as to facilitate controlling the grade for the pivoting end effector 1.

For example, as shown in FIG. 18A to FIG. 18B and FIG. 19, the extension direction of the grade slot 900 is consistent with the extension direction of the handle 9; and the first rotation direction and the second rotation direction are substantially perpendicular to the extension direction of the handle 9.

The detachable portion 3 further includes a closing mechanism, a surgical fastener pushing assembly, and a cutting device; and the descriptions in the foregoing embodiments may be specifically referred to for these structures. As shown in FIG. 18A to FIG. 18B, the handle 9 further includes a two-way control button 94; the two-way control button 94 includes a first end 941 and a second end 942; and the two-way control button 94 is configured that the first end is pressed to control the closing stage, the surgical fastener pushing stage and the cutting stage to be sequentially executed; in the closing stage, the closing mechanism makes the fastener-cartridge assembly 11 and the anvil 12 engage with each other to close the end effector 1, so that the end effector 1 clamps the target tissue; in the surgical fastener pushing stage, the surgical fastener pushing assembly pushes the surgical fastener out of the fastener-cartridge assembly 11 to suture the target tissue; in the cutting stage, the cutting device cuts the target tissue; and the two-way control button 94 is further configured that the second end is pressed to control the closing mechanism not to make the fastener-cartridge assembly 11 and the anvil 12 engage with other, and the fastener-cartridge assembly 11 and the anvil 12 get away from each other to open the end effector 1.

For example, as shown in FIG. 18A to FIG. 18B and FIG. 19, the two-way control button 94 is located on the first surface 91 of the handle 9, is adjacent to the dial switch, and is arranged, together with the dial switch, along the extension direction of the handle 9, so as to facilitate the operator to operate the dial 93 and the two-way control button 94. For example, the first end of the two-way control button 94 is opposite to the second end of the two-way control button 94 in the extension direction of the handle 9 to further facilitate operation of the first end 941 and the second end and 942 of the two-way control button 94.

For example, as shown in FIG. 18A to FIG. 18B and FIG. 19, the handle 9 further includes a safety prompt button 95; the safety prompt button 95 is configured to be in a normal close prompt state after the first end 941 of the two-way control button 94 is pressed and after the closing stage is normally performed, to prompt the operator that the first end 941 of the two-way control button 94 can continue to be pressed to perform the surgical fastener pushing stage, and the safety prompt button 95 is configured to be in a normal suture prompt state, after the surgical fastener pushing stage is normally performed, to prompt the operator that the first end 941 of the two-way control button 94 can continue to be pressed to perform the cutting stage, and the safety prompt button 95 is configured to be in a normal cut prompt state, after the cutting stage is normally performed, to prompt the operator that the second end 942 of the two-way control button 94 can be pressed to open the end effector 1.

For example, in the normal close prompt state, the normal suture prompt state and the normal cut prompt state, the safety prompt button 95 protrudes from the surface of the handle 9, otherwise, the safety prompt button 95 is recessed below the surface of the handle 9 or is substantially flush with the surface of the handle 9, so that the operator may know whether each stage is proceeding normally by observing or touching the safety prompt button 95 in each stage, so as to decide operation of a next step.

For example, as shown in FIG. 18A to FIG. 18B and FIG. 19, the handle 9 further has a second surface 92; the second surface 92 is adjacent to and intersects with the first surface 92; and the safety prompt button 95 is located on the second surface 92 of the handle 9.

Figure 20:
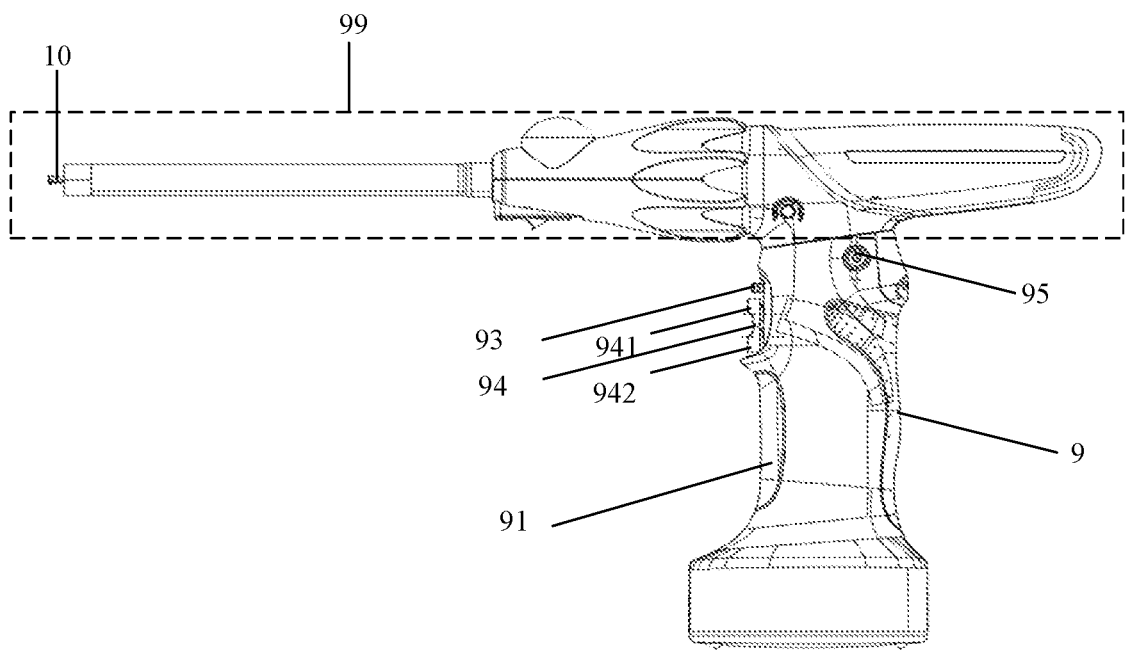
FIG. 20 is a schematic diagram of a surgical stapler main body provided by an embodiment of the present disclosure.

At least one embodiment of the present disclosure provides a surgical stapler main body, exemplarily, FIG. 20 is a schematic diagram of the surgical stapler main body provided by an embodiment of the present disclosure. As shown in FIG. 20, the surgical stapler main body includes any one of the handle 9 provided by the embodiments of the present disclosure, and a driver portion 99 connected with the handle 9. An overall extension direction of the driver portion 99 is the axial direction; the axial direction intersects with the extension direction of the handle 9; an end of the driver portion 99 away from the handle 9 is in detachable connection with the detachable portion 3, and includes an electric motor and a rear articulation driver member 82; the electric motor is in signal connection with the dial switch; the dial switch controls operation of the electric motor; the rear articulation driver member 82 is connected with the electric motor, and extends along the axial direction; and the electric motor is configured to rotate under control of the dial 93 switch to drive the rear articulation driver member 82 to move along the axial direction so as to drive the end effector 1 to pivot, so that operation of the electric motor may be controlled by operating the dial 93 on the handle 9, to control movement of the rear articulation driver member 82, so as to control a pivoting angle of the end effector 1, which is convenient for operation.

For example, the driver portion 99 is in detachable connection with the handle 9. With respect to the surgical stapler main body, the driver portion 99 may be replaceable, and the handle may also be replaceable, which is favorable for cost saving.

For example, in the case where the dial 93 is configured to be rotatable by grades toward the first rotation direction and/or the second rotation direction, each time the dial 93 rotates toward the first toggle direction by one grade, the electric motor rotates in a positive direction by one grade to drive the rear articulation driver member 82 to move away from the handle 9 along the axial direction by one grade of distance, so as to make the end effector 1 rotate by one grade toward the first pivoting direction; each time the dial 93 rotates toward the second pivoting direction by one grade, the electric motor rotates in a opposite direction by one grade to drive the rear articulation driver member 82 to move along the axial direction close to the handle 9 by one grade, so as to make the end effector 1 rotate toward the second pivoting direction by one grade, so that the dial 93 on the handle 9 may be operated to conveniently control the rotation direction and the grade of the electric motor, so as to control movement of the rear articulation driver member 82, to control the pivoting angle of the end effector 1, which is convenient for operation.

For example, the driver portion 99 further includes a first driver mechanism 10; the first driver mechanism 10 and the rear articulation driver member 82 extend in a same direction and are arranged side by side; and the first driver mechanism 10 is configured that in the closing stage, the first driver mechanism 10 is in detachable connection with the closing mechanism to drive the closing mechanism to close the end effector 1; in the surgical fastener pushing stage after the closing stage, the first driver mechanism 10 is separated from the closing mechanism and drives the surgical fastener pushing assembly to push the surgical fastener out of the fastener-cartridge assembly 11 to suture the target tissue; and in the cutting stage, the first driver mechanism 10 drives the cutting device to cut the target tissue. The description of the foregoing embodiments may be referred to for specific features of the first driver mechanism 10; and no details will be repeated here.

For example, as shown in FIG. 20, the driver portion 99 is located on the first surface 91 of the handle 9, and the axial direction intersects with the first surface 91; the driver portion 99 includes a first end 941 connected with the handle 9 and a second end 942 away from the of the handle 9 in the axial direction; the first surface 91 faces the second end 942 of the driver portion 99, so that it is convenient for the operator to toggle the dial 93 on the first surface 91, and the second surface 92 is adjacent to and intersects with the first surface 91, which is convenient for the operator to identify the safety prompt switch on the second surface 92.

At least one embodiment of the present disclosure provides a surgical stapler 100, and the surgical stapler 100 includes any surgical stapler main body provided by the embodiments of the present disclosure and the detachable portion 3. The detachable portion 3 of the surgical stapler 100 is in detachable connection with the main body portion 4 of the surgical stapler 100; the detachable portion 3 further includes a front articulation driver assembly; the front articulation driver assembly is connected with the end effector 1; the detachable portion 3 is in detachable connection with the main body of the surgical stapler 100 so that the front articulation driver assembly is in detachable connection with the rear articulation driver member 82; and the front articulation driver assembly drives, as driven by the rear articulation driver member 82, the end effector 1 to pivot. The description in the foregoing embodiments may be referred to for specific structures of the front articulation driver assembly and the rear articulation driver member, and no details will be repeated here.

For example, with respect to the surgical stapler 100 including any surgical stapler main body provided by the embodiment of the present disclosure, the detachable portion 3 further includes a second driver mechanism 20 extending along the axial direction; the detachable portion 3 is connected with the surgical stapler 100 main body so that the second driver mechanism 20 is in detachable connection with the first driver mechanism 10; the second driver mechanism 20 is configured to be in detachable connection with the closing mechanism in the closing stage and to move toward the end effector 1 as driven by the first driver mechanism 10, so that the closing mechanism closes the end effector 1; the second driver mechanism 20 is further configured to be separated from the closing mechanism in the surgical fastener pushing stage and continue to move toward the second end 942 of the end effector 1 as driven by the first driver mechanism 10 to drive the surgical fastener pushing assembly to push the surgical fastener out of the fastener-cartridge assembly 11; the second driver mechanism 20 is further configured such that: in the cutting stage, the second driver mechanism 20 drives, as driven by the first driver mechanism 10, the cutting device to cut the target tissue. The description in the foregoing embodiments may be referred to for specific structures of the second driver mechanism 20 and the first driver mechanism 10, and no details are repeated here.

What have been described above are only specific implementations of the present disclosure, the protection scope of the present disclosure is not limited thereto, and the protection scope of the present disclosure should be based on the protection scope of the claims.

The invention claimed is:

1. A surgical stapler, comprising:
   an end effector, comprising a fastener-cartridge assembly and an anvil, wherein at least one surgical fastener is provided in the fastener-cartridge assembly;
   a closing mechanism, configured to drive the fastener-cartridge assembly and the anvil to engage with each other to close the end effector so that a target tissue is clamped between the fastener-cartridge assembly and the anvil;
   a surgical fastener pushing assembly, configured to push the surgical fastener out of the fastener-cartridge assembly into the target tissue to suture a part of the target tissue;
   a first driver mechanism, wherein the first driver mechanism is configured that in a closing stage, the first driver mechanism is in detachable connection with the closing mechanism to drive the closing mechanism to close the end effector; and the first driver mechanism is configured that in a surgical fastener pushing stage after the closing stage, the first driver mechanism is separated from the closing mechanism and drives the surgical fastener pushing assembly to push the surgical fastener out of the fastener-cartridge assembly to suture an entirety of a part of the target tissue that is required to be sutured; and
   a cutting device, configured to cut, as driven by the first driver mechanism, the target tissue, in a cutting stage which is after the surgical fastener pushing stage;
   the surgical stapler further comprises:
   a cutting driver mechanism, configured to drive, as driven by the first driver mechanism, the cutting device to cut the target tissue;
   in the closing stage during which the first driver mechanism drives the closing mechanism to close the end effector and in the surgical fastener pushing stage during which the surgical fastener pushing assembly is driven to push the surgical fastener out of the fastener-cartridge assembly, the first driver mechanism moves toward the end effector; and
   in the cutting stage, the first driver mechanism moves away from the end effector to drive the cutting driver mechanism to move away from the end effector.

2. The surgical stapler according to claim 1, further comprising:
   a second driver mechanism, connected with the first driver mechanism so as to move as driven by the first driver mechanism, wherein
   the second driver mechanism is configured to be in detachable connection with the closing mechanism in the closing stage and is configured to move as driven by the first driver mechanism toward the end effector to enable the closing mechanism to be in contact with the fastener-cartridge assembly and the anvil and apply pressure to the fastener-cartridge assembly and the anvil to close the end effector in the closing stage;
   the second driver mechanism is further configured to be separated from the closing mechanism in the surgical fastener pushing stage, and is configured to drive, as driven by the first driver mechanism, the surgical fastener pushing assembly to push the surgical fastener out of the fastener-cartridge assembly in the surgical fastener pushing stage; and
   the second driver mechanism is further configured to be connected with the cutting driver mechanism in the cutting stage to drive the cutting driver mechanism to move.

3. The surgical stapler according to claim 1, wherein
   the end effector comprises a first end and a second end that are opposite to each other in an axial direction, the first end of the end effector is closer to the closing mechanism;
   before the surgical fastener pushing stage, the cutting device is at the first end of the end effector;
   in the surgical fastener pushing stage, the first driver mechanism moves along the axial direction toward the end effector to drive the cutting driver mechanism and the surgical fastener pushing assembly to move synchronously toward the end effector, the cutting driver mechanism drives the cutting device to move from the first end of the end effector to the second end of the end effector during which the cutting device does not cut the target tissue; and
   in the cutting stage, the first driver mechanism moves along the axial direction away from the end effector to drive the cutting driver mechanism to move away from the end effector, and the cutting driver mechanism drives the cutting device to move from the second end of the end effector to the first end of the end effector during which the cutting device cuts the target tissue.

4. The surgical stapler according to claim 1, wherein
   the end effector comprises a first end and a second end that are opposite to each other in an axial direction;
   before the surgical fastener pushing stage, the cutting device is at the second end of the end effector;
   in the surgical fastener pushing stage, the first driver mechanism moves along the axial direction toward the end effector to drive the cutting driver mechanism and the surgical fastener pushing assembly to move synchronously toward the end effector, the cutting driver mechanism moves from the first end of the end effector to the second end of the end effector to be connected with the cutting device that is at the second end of the end effector; and
   in the cutting stage, the first driver mechanism moves along the axial direction away from the end effector to drive the cutting driver mechanism to move away from the end effector, and the cutting driver mechanism drives the cutting device to move from the second end of the end effector to the first end of the end effector during which the cutting device cuts the target tissue.

5. The surgical stapler according to claim 3, wherein the cutting device comprises a blade-carrying member; and
   a cutting blade, in movable connection with the blade-carrying member, wherein the cutting driver mechanism is configured to drive the blade-carrying member to move so as to drive the cutting blade to move;
   in the surgical fastener pushing stage, the cutting blade is at least partially in the blade-carrying member, and the cutting blade has a preset distance to the target tissue clamped between the fastener-cartridge assembly and the anvil, so that the cutting blade is not in contact with the target tissue; and in the cutting stage, the cutting blade is driven under action of a first driving force to be in contact with the target tissue to cut the target tissue.

6. The surgical stapler according to claim 5, wherein the fastener-cartridge assembly comprises:

a fastener-cartridge, wherein at least one surgical fastener is provided inside the fastener-cartridge;

an outer bracket, fixed on the fastener-cartridge and has a first portion and a second portion that are opposite to each other, wherein both the first portion and the second portion are on a side of the fastener-cartridge away from the anvil and extend along the axial direction, the first portion of the outer bracket and the second portion of the outer bracket are spaced apart from each other to define a first chute extending along the axial direction, and each of the first portion of the outer bracket and the second portion of the outer bracket has an upper surface away from the fastener-cartridge and a lower surface opposite to the respective upper surface;

the cutting driver mechanism comprises:

a main body portion, wherein in a process that the cutting driver mechanism drives the blade-carrying member to move, the main body portion is configured to be connected with the blade-carrying member, and the first end of the main body portion away from the anvil slides in the first chute; and a first sliding portion which is connected with the main body portion and is supported on the upper surface of the first portion of the outer bracket and the upper surface of the second portion of the outer bracket, and is configured to be able to slide along the upper surface of the first portion of the outer bracket and the upper surface of the second portion of the outer bracket;

the fastener-cartridge comprises a fastener-cartridge bracket, the fastener-cartridge bracket comprises a first portion and a second portion that both extend along the axial direction, both the first portion of the fastener-cartridge bracket and the second portion of the fastener-cartridge bracket comprises a surgical fastener slot for accommodating the surgical fastener, and the first portion of the fastener-cartridge bracket and the second portion of the fastener-cartridge bracket define a second chute extending along the axial direction, the second chute is opposite to the first chute, and in a process that the cutting driver mechanism drives the blade-carrying member to move, the second end of the main body portion of the cutting driver mechanism close to the anvil slides in the second chute.

7. The surgical stapler according to claim 6, wherein the fastener-cartridge has a fastener out-put surface opposite to the anvil, and a cross section of an entire body constituted by the main body portion and the first sliding portion in a direction perpendicular to the fastener out-put surface is T-shaped.

8. The surgical stapler according to claim 6, wherein the cutting driver mechanism further comprising:

a second sliding portion which is connected with the main body portion, on a side of both the first portion and the second portion away from the first sliding portion, is in contact with the lower surface of the first portion and the lower surface of the second portion, and is configured to be able to slide along the lower surface of the first portion and the lower surface of the second portion.

9. The surgical stapler according to claim 6, wherein the blade-carrying member comprises:

an accommodating cavity, wherein the cutting blade is at least partially located in the accommodating cavity and comprises a cutting edge;

a position limit structure, configured to movably connect the cutting blade to the blade-carrying member; and a blade ejection driver mechanism, configured to apply the first driving force to the cutting blade so that the cutting edge moves toward the target tissue to be in contact with the target tissue; the accommodating cavity comprises an opening toward the target tissue, the cutting blade is configured to, under the action of the first driving force, be at least partially exposed from the opening so that the cutting edge is in contact with the target tissue; and a part of the cutting blade exposed from the opening contacts with the target tissue through the second chute and slides in the second chute.

10. The surgical stapler according to claim 9, wherein the accommodating cavity has an inner wall, the inner wall comprises a plurality of wall faces which at least partially intersect with each other, the plurality of wall faces constitute the position limit structure, and in the surgical fastener pushing stage, the plurality of wall faces clamp the cutting blade in a fixed position;

the plurality of wall faces include a first wall face and a second wall face that are opposite to each other, the first wall face and the second wall face intersect with the opening and both intersect with the axial direction; under action of the first driving force, the cutting blade slides along the first wall face and the second wall face to be exposed from the opening;

both the first wall face and the second wall face are perpendicular to the axial direction;

the fastener-cartridge bracket comprises:

a resistance face, facing the blade ejection driver mechanism, wherein the blade ejection driver mechanism is configured to hit the resistance face when the cutting device reaches the second end of the end effector as driven by the cutting driver mechanism, so that the resistance face applies a blade ejection driving force on the blade ejection driver mechanism, and the blade ejection driver mechanism is configured to be in contact with the cutting blade under action of the blade ejection driving force to apply the first driving force to the cutting blade to drive the cutting blade to move toward the target tissue.

11. The surgical stapler according to claim 9, wherein the blade-carrying member further comprises a first connection structure, and the main body portion of the cutting driver mechanism comprises a second connection structure;

in the surgical fastener pushing stage, the first connection structure is not connected with the second connection structure;

after the surgical fastener pushing stage and before the cutting stage, the first connection structure is connected with the second connection structure; the main body portion further comprises a force applying face facing the blade-carrying member, and the blade-carrying member comprises a force bearing face facing the main body portion;

in the surgical fastener pushing stage, the cutting driver mechanism moves toward the blade-carrying member so that the force applying face is in contact with the force bearing face, and the cutting driver mechanism applies a second driving force to the force bearing face through the force applying face to drive the blade-carrying member to move;

the first connection structure also serves as the blade ejection driver mechanism, the blade ejection driver mechanism is at least partially located in the accommodating cavity and is configured to be movable along the axial direction;

the blade ejection driver mechanism extends along the axial direction, and comprises a first end close to the cutting driver mechanism in the axial direction and a second end opposite to the first end; the blade-carrying member comprises a via hole passing through the force bearing face and in communication with the accommodating cavity;

in the surgical fastener pushing stage, the first end of the blade ejection driver mechanism is in the accommodating cavity, the second end of the blade ejection driver mechanism extends to outside of the accommodating cavity, and the blade ejection driver mechanism does not move relative to the cutting blade along the axial direction;

in a case where the fastener-cartridge bracket comprises a resistance face, the blade ejection driver mechanism is configured to hit the resistance face when the cutting device reaches the second end of the end effector, so that the resistance face applies a blade ejection driving force on the blade ejection driver mechanism, and the blade ejection driver mechanism is configured to move away from the second end of the end effector along the axial direction under action of the blade ejection driving force to be in contact with the cutting blade to apply the first driving force to the cutting blade to drive the cutting blade to move toward the target tissue, and the first end of the blade ejection driver mechanism moves to the outside of the accommodating cavity through the via hole to be connected with the second connection structure;

in the surgical fastener pushing stage, the cutting edge of the cutting blade faces the target tissue, the cutting blade further comprises a first slope intersecting with the cutting edge, the blade ejection driver mechanism comprises a second slope, the second slope is on a side of the first slope away from the cutting edge, is on a side of the first slope that is close to the second end of the end effector in the axial direction, and is parallel to the first slope, and both the first slope and the second slope intersect with the axial direction;

when the second end of the blade ejection driver mechanism hits the resistance face, the blade ejection driver mechanism is configured to move away from the second end of the end effector along the axial direction under action of the blade ejection driving force, so that the second slope is in contact with the first slope of the cutting blade to apply the first driving force to the cutting blade, and while the blade ejection driver mechanism moves away from the second end of the end effector along the axial direction, the cutting blade moves toward the target tissue and the first slope slides toward the target tissue relative to the second slope;

an included angle between the second slope and a direction which is from the second slope to the second end of the end effector along the axial direction, is an obtuse angle.

12. The surgical stapler according to claim 11, wherein the main body portion of the cutting driver mechanism comprises:
a hollow region, running through the force applying face so that the force applying face has the via hole, wherein the second connection structure is in the hollow region, and the second end of the blade ejection driver mechanism passes through the via hole and enters the hollow region to be connected with the second connection structure.

13. The surgical stapler according to claim 12, wherein the second connection structure comprises:
an elastic connection piece, protruding from an inner wall of the hollow region that faces the second end of the blade ejection driver mechanism, wherein the second end of the blade ejection driver mechanism has a nestification hole;
the elastic connection piece comprises:
an elastic connection rod, protruding from the inner wall of the hollow region that faces the second end of the blade ejection driver mechanism and extends along the axial direction; and
an end protrusion, on an end of the elastic connection rod away from the inner wall and protruding from the elastic connection rod along a second direction perpendicular to the axial direction; and
the end protrusion is nested in the nestification hole so that the second end of the blade ejection driver mechanism is connected with the elastic connection piece;
an end face of the end protrusion that protrudes from the elastic connection rod is an arc-shaped face, and the blade ejection driver mechanism and the elastic connection piece are configured that when the blade ejection driver mechanism moves away from the second end of the end effector along the axial direction under the action of the blade ejection driver mechanism to reach the end protrusion, the second end of the blade ejection driver mechanism abuts against the arc-shaped face to make the elastic connection rod elastically deformed in the second direction, and then when the blade ejection driver mechanism continues to move away from the second end of the end effector along the axial direction under the action of the blade ejection driving force so that the nestification hole is opposite to the end protrusion, under action of an elastic restoring force of the elastic connection rod, the end protrusion moves along the second direction toward the nestification hole and is nested into the nestification hole so that the cutting driver mechanism is connected with the blade-carrying member.

14. The surgical stapler according to claim 12, wherein the second connection structure comprises:
an elastic connection piece, protruding from an inner wall of the hollow region that faces the second end of the blade ejection driver mechanism, wherein the elastic connection piece has a nestification hole;
the second end of the blade ejection driver mechanism has an end protrusion, the end protrusion protrudes from the second end of the blade ejection driver mechanism along a second direction perpendicular to the axial direction; and
the end protrusion is nested in the nestification hole so that the second end of the blade ejection driver mechanism is connected with the elastic connection piece;
the end face of the end protrusion that protrudes from the second end of the blade ejection driver mechanism is an arc-shaped face, and the blade ejection driver mechanism and the elastic connection piece are configured such that: when the blade ejection driver mechanism moves, under action of the blade ejection driving force, away from the second end of the end effector so that the elastic connection piece reaches the end protrusion, the elastic connection piece abuts against the arc-shaped face to make the elastic connection piece elastically deformed in the second direction, and when the blade ejection driver mechanism continues to move, under action of the blade ejection driving force, away from the second end of the end effector along the axial direction so that the nestification hole is opposite to the end protrusion, the elastic connection piece moves, under action of an elastic restoring force of the elastic connection rod, toward the nestification hole along the second direction, so that the end protrusion is nested into the nestification hole to enable the cutting driver mechanism to be connected with the blade-carrying member.

15. The surgical stapler according to any one of claim 9, wherein the blade-carrying member further comprises a first connection structure, and the main body portion of the cutting driver mechanism comprises a second connection structure;
   at least in the surgical fastener pushing stage, the first connection structure is connected with the second connection structure so that cutting driver mechanism is connected with the blade-carrying member;
   the first connection structure comprises a first connection end close to the cutting driver mechanism, and the second connection structure comprises a second connection end close to the first connection structure;
   before the surgical fastener pushing stage, the cutting driver mechanism is not connected with the blade-carrying member; and
   in the surgical fastener pushing stage, as driven by the first driver mechanism, the cutting driver mechanism moves toward the blade-carrying member so that the first connection end is connected with the second connection end;
   the main body portion of the cutting driver mechanism further comprises a force applying face facing the blade-carrying member, and the blade-carrying member comprises a force bearing face facing the main body portion;
   in the surgical fastener pushing stage, the cutting driver mechanism moves toward the blade-carrying member so that the force applying face is in contact with the force bearing face, the first connection end is connected with the second connection end, and the cutting driver mechanism applies a second driving force to the force bearing face through the force applying face, and applies a third driving force to the first connection structure through the second connection structure to drive the blade-carrying member to move.

16. The surgical stapler according to claim 15, wherein the main body portion of the cutting driver mechanism comprises:
   a hollow region, running through the force applying face so that the force applying face has the via hole, wherein the second connection structure is in the hollow region, and the first connection end passes through the via hole and enters the hollow region to be connected with the second connection end of the second connection structure.

17. The surgical stapler according to claim 16, wherein the second connection structure comprises:
   an elastic connection piece, protruding from the inner wall of the hollow region that faces the first connection end, wherein an end of the elastic connection piece away from the inner wall is the second connection end, and the second connection end has a nestification hole;
   the elastic connection piece comprises:
   an elastic connection rod, protruding from the inner wall of the hollow region that faces the first connection end and extends along the axial direction; and
   an end protrusion which is at one end of the elastic connection rod away from the inner wall and protrudes from the elastic connection rod in a second direction perpendicular to the axial direction;
   the end protrusion is nested in the nestification hole so that the second end of the blade ejection driver mechanism is connected with the elastic connection piece;
   the end face of the end protrusion that protrudes from the elastic connection rod is an arc-shaped face, and the cutting driver mechanism and the elastic connection piece are configured such that: when the cutting driver mechanism moves, as driven by the first driver mechanism, along the axial direction toward the second end of the end effector to reach the first connection end, the first connection end abuts against the arc-shaped face to make the elastic connection rod elastically deformed in the second direction; and when the cutting driver mechanism, as driven by the first driver mechanism, continues to move along the axial direction toward the second end of the end effector so that the nestification hole is opposite to the end protrusion, the end protrusion moves, under the action of the elastic restoring force of the elastic connection rod, toward the nestification hole along the second direction so that the elastic connection rod is nested in the nestification hole, so that the first connection end is connected with the second connection end.

18. The surgical stapler according to claim 16, wherein the second connection structure comprises:
   an elastic connection piece, protruding from the inner wall of the hollow region that faces the first connection end, wherein an end of the elastic connection piece away from the inner wall is the second connection end, and the second connection end has a nestification hole;
   the elastic connection piece has an end protrusion, the end protrusion protrudes from the second end of the blade ejection driver mechanism in a second direction perpendicular to the axial direction; and
   the end protrusion is nested in the nestification hole so that the second end of the blade ejection driver mechanism is connected with the elastic connection piece; the fastener-cartridge bracket comprises:
   a resistance face, facing the blade ejection driver mechanism, wherein the blade ejection driver mechanism is configured to hit the resistance face when the cutting device reaches the second end of the end effector as driven by the cutting driver mechanism, so that the resistance face applies a blade ejection driving force on the blade ejection driver mechanism;
   the end face of the end protrusion that protrudes from the second end of the blade ejection driver mechanism is an arc-shaped face, and the blade ejection driver mechanism and the elastic connection piece are configured such that: when the blade ejection driver mechanism moves, under action of the blade ejection driving force, away from the second end of the end effector so that the elastic connection piece reaches the end protrusion, the elastic connection piece abuts against the arc-shaped face to make the elastic connection piece elastically deformed in the second direction, and when the blade ejection driver mechanism continues to move, under the action of the blade ejection driving force, away from the second end of the end effector along the axial direction so that the nestification hole is opposite to the end protrusion, the elastic connection piece moves, under action of an elastic restoring force of the elastic connection rod, toward the nestification hole along the second direction, so that the end protrusion is nested into the nestification hole to make the cutting driver mechanism connected with the blade-carrying member.

* * * * *